United States Patent
Hölder et al.

(10) Patent No.: US 7,309,701 B2
(45) Date of Patent: *Dec. 18, 2007

(54) PYRIDAZINONE DERIVATIVES AS PHARMACEUTICALS AND PHARMACEUTICAL COMPOSITIONS CONTAINING THEM

(75) Inventors: Swen Hölder, Frankfurt (DE); Thorsten Naumann, Hirzenhain (DE); Karl Schönafinger, Alzenau (DE); David William Will, Kriftel (DE); Hans Matter, Langenselbold (DE); Günther Müller, Sulzbach am Taunus (DE); Dominique Le Suisse, Montreuil (FR); Bernard Baudoin, Chaville (FR); Thomas Rooney, Orsay (FR); Franck Halley, Sevres (FR); Gilles Tiraboschi, Chevilly Larue (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 93 days.

This patent is subject to a terminal disclaimer.

(21) Appl. No.: 10/715,358

(22) Filed: Nov. 19, 2003

(65) Prior Publication Data

US 2004/0176377 A1    Sep. 9, 2004

Related U.S. Application Data

(60) Provisional application No. 60/438,336, filed on Jan. 7, 2003.

(30) Foreign Application Priority Data

Nov. 19, 2002    (FR) ................... 02 14443

(51) Int. Cl.
*C07D 413/12* (2006.01)
*C07D 403/12* (2006.01)
*C07D 237/04* (2006.01)
*A61K 31/501* (2006.01)
*A61K 31/50* (2006.01)

(52) U.S. Cl. ............... 514/236.5; 514/252.02; 514/252.03; 514/252.04; 514/252.05; 514/252.06; 544/114; 544/238; 544/239

(58) Field of Classification Search ........... 544/114, 544/238, 239; 514/236.5, 252.02, 252.03, 514/252.04, 252.05, 252.06
See application file for complete search history.

(56) References Cited

U.S. PATENT DOCUMENTS

| | | | |
|---|---|---|---|
| 4,353,905 A | 10/1982 | Sircar et al. | |
| 4,734,415 A | 3/1988 | Sircar et al. | |
| 5,418,233 A | 5/1995 | Linz et al. | |

FOREIGN PATENT DOCUMENTS

| | | |
|---|---|---|
| EP | 0 075 436 B1 | 3/1983 |
| EP | 1 061 077 A1 | 12/2000 |
| EP | 1 319 659 A1 | 6/2003 |
| JP | 9-216883 | 8/1997 |
| WO | WO 9944995 A1 * | 9/1999 |
| WO | WO 02/22587 A1 | 3/2002 |
| WO | WO 02/50065 A2 | 6/2002 |
| WO | WO 03/035065 A1 | 1/2003 |
| WO | WO 03/059891 A1 | 7/2003 |

OTHER PUBLICATIONS

Chalmers (TiPS vol. 17, pp. 166-172 Apr. 1996).*
S. Nikoulina et al., "Inhibition of Glycogen Synthase Kinase 3 Improves Insulin Action and Glucose Metabolism in Human Skeletal Muscle," *Diabetes*, Vo. 51, pp. 2190-2198, Jul. 2002.
E. Henriksen et al., "Modulation of Muscle Insulin Resistance by Selective Inhibition of GSIK-3 in Zucker Diabetic Fatty Rats," *Am. J. Physiol. Endocrinol. Metab.*, vol. 284, pp. 892-900, 2003.
An English translation of JP 9-216883, (Aug. 19, 1997).
An English language Patent Abstract of Japan of JP 9-216883, (Aug. 19, 1997).

* cited by examiner

*Primary Examiner*—Kahsay Habte
(74) *Attorney, Agent, or Firm*—Finnegan, Henderson, Farabow, Garrett & Dunner, L.L.P.

(57) ABSTRACT

The present invention relates to novel pyridazinone derivatives of the general formula (I)

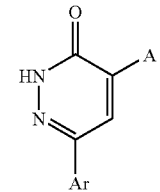

wherein
A is A1 or A2;

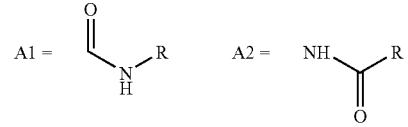

R is unsubstituted or at least monosubstituted $C_1$-$C_{10}$-alkyl, aryl, aryl-($C_1$-$C_{10}$-alkyl)-, heteroaryl, heteroaryl-($C_1$-$C_{10}$-alkyl)-, heterocyclyl, heterocyclyl-($C_1$-$C_{10}$-alkyl)-, $C_3$-$C_{10}$-cycloalkyl, polycycloalkyl, $C_2$-$C_{10}$-alkenyl or $C_2$-$C_{10}$-alkinyl and
Ar is unsubstituted or at least monosubstituted aryl or heteroaryl.

4 Claims, No Drawings

PYRIDAZINONE DERIVATIVES AS PHARMACEUTICALS AND PHARMACEUTICAL COMPOSITIONS CONTAINING THEM

This application claims benefit of U.S. Provisional Application No. 60/438,336, filed Jan. 7, 2003, which is incorporated herein by reference.

The present invention relates to compounds according to the general formula (I), with the definitions of the substituents A and Ar given below in the text, as well as their physiologically acceptable salts, methods for producing these compounds and their use as pharmaceuticals.

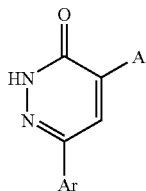

(I)

These compounds are kinase inhibitors, in particular inhibitors of the kinase GSK-3β (glycogen synthase kinase-3β).

It is known from literature that in the case of metabolic diseases such as diabetes or neurodegenerative diseases such as Alzheimer's disease, there is a connection between the therapy of said diseases and the inhibition of GSK-3β or the phosphorylation of the tau-protein (S. E. Nikoulina, Diabetes, vol. 51, pp. 2190-2198, 2002; Henrikson, Am. J. Physiol., vol. 284, pp. E892-900, 2003). Many compounds or pharmaceuticals, respectively, are already known to be employed for the treatment of said diseases, which compounds interfere at different places of the biochemical processes causing the respective disease. However, there are no compounds known until now, which effect inhibition of GSK-3β.

Pyridazinone derivatives are well known pharmaceuticals, but it has not been reported so far that pyridazinone derivatives can be employed for the inhibition of GSK-3β or tau-phosporylation, respectively. Pyridazinone derivatives described in literature differ from those of the present invention due to a different substitution pattern and different indications.

WO 03/059891 discloses pyridazinone derivatives that are useful for treating diseases and conditions caused or exacerbated by unregulated p38 MAP Kinase activity and/or TNF activity. The compounds described therein can be used, for example, for the treatment of inflammatory conditions, diabetes, Alzheimer's disease or cancer. They differ from the compounds of the present invention in the substitution of the pyridazinone cycle, since the nitrogen at position 2 of the cycle is mostly substituted with alky, aryl or heteroaryl and at position 4 of the cycle there is no amido group defined as substituent (equals substituent A of the compounds of the present invention).

The documents EP-A 075 436, U.S. Pat. Nos. 4,734,415 and 4,353,905 describe pyridazinone derivatives as antihypertensive agents and as agents which increase cardiac contractibility. These pyridazinone derivatives have a phenyl residue at position 6 of the pyridazinone cycle, said phenyl residue is additionally substituted with a heterocycle containing at least one nitrogen atom. Whereas the pyridazinone derivatives described in the documents EP-A 075 436 and U.S. Pat. No. 4,353,905 do not have a substituent at position 4 of the pyridazinone cycle, those disclosed in U.S. Pat. No. 4,734,415 may have an amido group substituted with lower alkyl at this position. Compounds as such, explicitly disclosed by U.S. Pat. No. 4,734,415, are not a subject of the present invention.

Thus, there exists a strong need for compounds having an inhibitory effect for GSK-3β and/or the phosphorylation of the tau-protein. The object of the present invention is to provide compounds showing this ability.

This object is attained by pyridazinone derivatives according to the following formula (I)

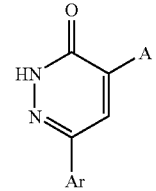

(I)

wherein A represents A1 or A2

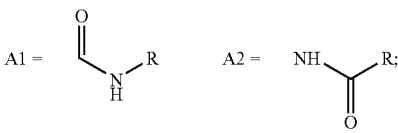

R is unsubstituted or at least monosubstituted $C_1$-$C_{10}$-alkyl, aryl, aryl-($C_1$-$C_{10}$-alkyl)-, heteroaryl, heteroaryl-($C_1$-$C_{10}$-alkyl)-, heterocyclyl, heterocyclyl-($C_1$-$C_{10}$-alkyl)-, $C_3$-$C_{10}$-cycloalkyl, polycycloalkyl, $C_2$-$C_{10}$-alkenyl or $C_2$-$C_{10}$-alkinyl, where the substituents are selected from halogen, —CN, $C_1$-$C_{10}$-alkyl, —NO$_2$, —OR1, —C(O)OR1, —O—C(O)R1, —NR1R2, —NHC(O)R1, —C(O)NR1R2, —SR1, —S(O)R1, —SO$_2$R1, —NHSO$_2$R1, —SO$_2$NR1R2, —C(S)NR1R2, —NHC(S)R1, —O—SO$_2$R1, —SO$_2$—O—R1, oxo, —C(O)R1, —C(NH)NH$_2$, heterocyclyl, $C_3$-$C_{10}$-cycloalkyl, aryl-($C_1$-$C_6$-alkyl)-, aryl, heteroaryl, trifluoromethyl, trifluoromethylsulfanyl and trifluoromethoxy, and aryl, heterocyclyl and heteroaryl may in turn be at least monosubstituted with $C_1$-$C_6$-alkyl, $C_1$-$C_6$-alkoxy, halogen, trifluoromethyl, trifluoromethoxy or OH;

Ar is unsubstituted or at least monosubstituted aryl or heteroaryl;

where the substituents are selected from halogen, —CN, NO$_2$, $C_1$-$C_{10}$-alkyl, —OR1, —C(O)OR1, —O—C(O)R1, —NR1R2, —NHC(O)R1, —C(O)NR1R2, —NHC(S)R1, —C(S)NR1R2, —SR1, —S(O)R1, —SO$_2$R1, —NHSO$_2$R1, —SO$_2$NR1R2, —O—SO$_2$R1, —SO$_2$—O—R1, aryl, heteroaryl, aryl-($C_1$-$C_6$-alkyl)-,formyl, trifluoromethyl and trifluoromethoxy, and aryl and heteroaryl may in turn be at least monosubstituted with $C_1$-$C_6$-alkyl, $C_1$-$C_6$-alkoxy, halogen, trifluoromethyl, trifluoromethoxy or OH;

R1 and R2, independently from each other, are hydrogen;

unsubstituted or at least monosubstituted $C_1$-$C_{10}$-alkyl, $C_3$-$C_{10}$-cycloalkyl, aryl, aryl-($C_1$-$C_{10}$-alkyl)-, $C_2$-$C_{10}$-alkenyl, $C_2$-$C_{10}$-alkinyl, heterocyclyl, heterocyclyl-($C_1$-$C_{10}$- alkyl)- or heteroaryl, where the substituents are selected from halogen, $C_1$-$C_6$-alkyl, $C_1$-$C_6$-alkoxy, CN, $NO_2$, $NH_2$, ($C_1$-$C_6$-alkyl)amino-, di($C_1$-$C_6$-alkyl)amino-, OH, COOH, —COO—($C_1$-$C_6$-alkyl), —$CONH_2$, formyl, trifluoromethyl and trifluoromethoxy;

heteroaryl is a 5 to 10-membered, aromatic, mono- or bicyclic heterocycle containing one or more heteroatoms selected from N, O and S;

aryl is phenyl, indanyl, indenyl or naphthyl;

heterocyclyl is a 5 to 10-membered, aliphatic, mono- or bicyclic heterocycle containing one or more heteroatoms selected from N, O and S;

with the proviso that A is not —C(O)NH($C_1$-$C_6$-alkyl), in case Ar is phenyl which is at least monosubstituted with heterocyclyl or heteroaryl containing nitrogen.

If in the compounds of formula (I), groups, fragments, residues or substituents such as aryl, heteroaryl, alkyl etc., may be present several times, they all independently from each other have the meanings indicated and may hence, in each individual case, be identical with or different from each other. The following comments apply to (for example) aryl as well as to any other residue independently from its classification as aryl group, -substituent, -fragment or -residue. One example is the di($C_1$-$C_{10}$-alkyl)amino group in which the alkyl substituents may be identical or different (for instance 2×ethyl or 1×propyl and 1×heptyl).

If in the above-mentioned definitions of compounds according to formula (I) a substituent, for example, aryl, may be unsubstituted or at least mono-substituted with a group of further substituents, for example, $C_1$-$C_6$-alkyl, $C_1$-$C_6$-alkoxy, halogen etc., it applies in such cases, where there is a poly-substitution of aryl, that the selection from the group of further substituents is independently from each other. Thus, all combinations of further substituents are comprised in the case of, for example, a double-substitution of aryl. Therefore, aryl may be substituted twice with ethyl, aryl may be mono-substituted with methyl or ethoxy, respectively, aryl may be mono-substituted with ethyl or fluoro, respectively, aryl may be substituted twice with methoxy, etc.

Alkyl, alkenyl and alkynyl residues may be linear or branched. This also applies when they are part of other groups, for example, in alkoxy groups ($C_1$-$C_{10}$-alkyl-O—), alkoxycarbonyl groups or amino groups, or when they are substituted.

Examples of alkyl groups are: methyl, ethyl, propyl, butyl, pentyl, hexyl, heptyl, octyl, nonyl, and decyl. This comprises both the n-isomers of these residues and isopropyl, isobutyl, isopentyl, sec-butyl, tert-butyl, neopentyl, 3,3-dimethylbutyl etc. Furthermore, unless stated otherwise, the term alkyl here also includes unsubstituted alkyl residues as well as alkyl residues which are substituted by one or more, for example, one, two, three or four, identical or different residues, for example aryl, heteroaryl, alkoxy or halogen. The substituents may be present in any desired position of the alkyl group.

Examples of cycloalkyl residues are: cyclopropyl, cyclobutyl, cyclopentyl, cyclohexyl, cycloheptyl and cyclooctyl. All cycloalkyl groups may be unsubstituted or optionally substituted by one or more further residues, as exemplified above in the case of the alkyl groups.

Examples of alkenyl and alkynyl groups are the vinyl residue, the 1-propenyl residue, the 2-propenyl residue (allyl residue), the 2-butenyl residue, the 2-methyl-2-propenyl residue, the 3-methyl-2-butenyl residue, the ethynyl residue, the 2-propynyl residue (propargyl residue), the 2-butynyl residue or the 3-butynyl residue. The term alkenyl here also expressly includes cycloalkenyl residues and cycloalkenyl-alkyl-residues (alkyl substituted by cycloalkenyl) containing at least three carbon atoms. Examples of cycloalkenyl residues are cyclopentenyl, cyclohexenyl, cycloheptenyl and cyclooctenyl.

The alkenyl residues may have 1 to 3 conjugated or unconjugated double bonds in a straight or branched chain; the same applies to alkynyl residues in respect of triple bonds. The alkenyl and alkinyl residues may be unsubstituted or optionally substituted by one or more further residues, as exemplified above in the case of the alkyl groups.

Examples of polycycloalkyl residues are: adamantyl, quinuclidinyl, bornanyl, norbornanyl, bornenyl and norbornenyl.

If not stated otherwise, the above-mentioned aryl, heteroaryl and heterocyclic residues may be unsubstituted or may carry one or more, for example, one, two, three or four of the substituents indicated in the above definition, which substituents may be in any desired position. In monosubstituted phenyl residues, for example, the substituent may be in the 2-position, the 3-position or the 4-position, in disubstituted phenyl residues the substituents may be in 2,3-position, 2,4-position, 2,5-position, 2,6-position, 3,4-position or 3,5-position. In trisubstituted phenyl residues the substituents may be in 2,3,4-position, 2,3,5-position, 2,3,6-position, 2,4,5-position, 2,4,6-position or 3,4,5-position. In fourfold substituted phenyl residues, the substituents may be in the 2,3,4,5-position, the 2,3,4,6-position, or the 2, 3,5,6-position.

The above definitions as well as the following definitions relating to monovalent residues equally apply to the divalent residues phenylene, naphthylene and heteroarylene. Those divalent residues (fragments) may be attached to the adjacent groups by any ring carbon atom. In the case of a phenylene residue, these may be in 1,2-position (ortho-phenylene), 1,3-position (meta-phenylene) or 1,4-position (para-phenylene). In the case of 5-membered ring aromatics containing one heteroatom such as, for example, thiophene or furan, the two free bonds may be in 2,3-position, 2,4-position, 2,5-position or 3,4-position. A divalent residue derived from pyridine may be a 2,3-, 2,4-, 2,5-, 2,6-, 3,4- or 3,5-pyridinediyl residue. In the case of unsymmetrical divalent residues the present invention includes all positional isomers, i.e., in the case of a 2,3-pyridinediyl residue, for example, it includes the compound in which the one adjacent group is present in the 2-position and the other adjacent group is present in the 3-position as well as the compound in which the one adjacent group is present in the 3-position and the other adjacent group is present in the 2-position.

Unless stated otherwise, heteroaryl residues, heteroarylene residues, heterocyclyl residues, heterocyclylen residues and rings which are formed by two groups bonded to a nitrogen are preferably derived from completely saturated, partially saturated or completely unsaturated heterocycles (i.e., heteroalkanes, heteroalkanes, heteroaromatics), which contain one, two, three or four heteroatoms, which may be identical or different; more preferably they are derived from heterocycles which contain one, two, or three, in particular one or two, heteroatoms, which may be identical or different. Unless stated otherwise, the heterocycles may be monocyclic or polycyclic, for example monocyclic, bicyclic or tricyclic. Preferably they are monocyclic or bicyclic. The rings may be 5-membered rings, 6-membered rings or 7-membered rings. Examples of monocyclic and bicyclic heterocyclic systems from which residues occuring in the compounds of the formula (I) may be derived, are pyrrole, furan, thiophene, imidazole, pyrazole, 1,2,3-triazole, 1,2,4-triazole, 1,3-dioxole, 1,3-oxazole (=oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzimidazole, benzodioxol, quinoline, isoquinoline, quinazoline, quinoxaline, phthalazine, thienothiophenes, 1,8-naphthyridine and other naphthyridines, pteridin, or phenothiazine, each of them in saturated form (perhydro form) or in partially unsaturated form (for example in the dihydro form or the tetrahydro form) or in maximally unsaturated form, in case the respective forms are known and stable. The term "aryl" and the term "heteroaryl" as used herein comprise bicyclic residues in which both cycles are aromatic as well as bicyclic residues in which only one cycle is aromatic. Suitable aliphatic heterocycles include, for example, the saturated heterocycles pyrrolidine, piperidine, piperazine, imidazolidine, pyrazolidine, isothiazolidine, thiazolidine, isoxazolidine, oxazolidine, tetrahydrofuran, dioxolane, 2-oxo-azepane, morpholine and thiomorpholine as well as the partially unsaturated heterocycles isochromamyl, chromamyl, 1,2,3,4-tetrahydroisochinolyl and 1,2,3,4-tetrahydrochinolyl. The degree of saturation of heterocyclic groups is indicated in their individual definitions.

Substituents which may be derived from these heterocycles may be attached via any suitable carbon atom. Residues derived from nitrogen heterocycles may carry a hydrogen atom or a substituent on a ring nitrogen atom, and examples include pyrrole, imidazole, pyrrolidine, morpholine, piperazine residues, etc. Those nitrogen heterocyclic residues may also be attached via a ring nitrogen atom, in particular if the respective heterocyclic residue is bonded to a carbon atom. For example, a thienyl residue may be present as 2-thienyl or 3-thienyl, a piperidinyl residue as 1-piperidinyl (=piperidino), 2-piperidinyl, 3-piperidinyl or 4-piperidinyl. Suitable nitrogen heterocycles may also be present as N-oxides or as quarternary salts containing a counterion which is derived from a physiologically acceptable acid. Pyridyl residues, for example, may be present as pyridine-N-oxides.

Arylalkyl means an alkyl residue, which in turn is substituted by an aryl residue. Heteroarylalkyl means an alkyl residue, which in turn is substituted by a heteroaryl residue. Heterocyclylalkyl means an alkyl residue, which in turn is substituted by a heterocyclyl residue. For the definitions and possible substitutions of alkyl, heteroaryl, heterocyclyl and aryl it is referred to the above-mentioned definitions.

Halogen is fluorine, chlorine, bromine or iodine, preferably fluorine, chlorine or bromine, more preferably fluorine or chlorine.

The present invention includes all stereoisomeric forms of the compounds of the formula (I). Centers of asymmetry that are present in the compounds of formula (I) all independently of one another have S configuration or R configuration. The invention includes all possible enantiomers and diastereomers and mixtures of two or more stereoisomers, for example mixtures of enantiomers and/or diastereomers, in all ratios. Thus, compounds according to the present invention which may exist as enantiomers may be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are an object of the present invention. The preparation of individual stereoisomers may be carried out, if desired, by separation of a mixture by customary methods, for example by chromatography or crystallization, by the use of stereochemically uniform starting materials for the synthesis or by stereoselective synthesis. Optionally, a derivatization may be carried out before a separation of stereoisomers. The separation of a mixture of stereoisomers may be carried out at the stage of the compounds of the formula (I) or at the stage of an intermediate during the synthesis. The present invention also includes all tautomeric forms of the compounds of formula (I), in particular ketoenol tautomerism, i.e. the respective compounds may be present either in their keto form or in their enol form or in mixtures thereof in all ratios.

In case the compounds according to formula (I) contain one or more acidic or basic groups, the invention also comprises their corresponding physiologically or toxicologically acceptable salts.

Physiologically acceptable salts are particularly suitable for medical applications, due to their greater solubility in water compared with the starting or base compounds. Said salts must have a physiologically acceptable anion or cation. Suitable physiologically acceptable acid addition salts of the compounds of the invention are salts of inorganic acids such as hydrochloric acid, hydrobromic acid, phosphoric acid, metaphosphoric acid, nitric acid, sulfonic acid and sulfuric acid and also of organic acids such as, for example, acetic acid, theophyllinacetic acid, methylene-bis-b-oxynaphthoic acid, benzenesulfonic acid, benzoic acid, citric acid, ethanesulfonic acid, salicylic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid. Suitable pharmaceutically acceptable basic salts are ammonium salts, alkali metal salts (such as sodium salts and potassium salts) and alkaline earth metal salts (such as magnesium salts and calcium salts).

Salts having a pharmaceutically unacceptable anion are likewise included within the scope of the present invention as useful intermediates for preparing or purifying pharmaceutically acceptable salts and/or for use in nontherapeutic applications, for example, in-vitro applications.

If the compounds of the formula (I) simultaneously contain acidic and basic groups in the molecule, the invention also includes, in addition to the salt forms mentioned, inner salts or betaines (zwitterions).

The respective salts according to the formula (I) may be obtained by customary methods which are known to the person skilled in the art, for example, by contacting these compounds of the formula (I) with an organic or inorganic acid or base in a solvent or dispersant, or by anion exchange or cation exchange with other salts.

The present invention furthermore includes all solvates of compounds of the formula (I), for example hydrates or adducts with alcohols, active metabolites of the compounds of the formula (I), and also derivatives, which contain physiologically tolerable and cleavable groups, for example esters or amides.

The term "physiologically functional derivative" used herein relates to any physiologically acceptable derivative of an inventive compound of the formula (I), for example, an ester which on administration to a mammal, for example humans, is capable of forming (directly or indirectly) a compound of the formula (I) or an active metabolite thereof.

The physiologically functional derivatives also include prodrugs of the compounds of the invention. Such prodrugs may be metabolized in vivo to a compound of the invention. These prodrugs may or may not be active themselves and are also an object of the present invention.

The compounds of the invention may also be present in various polymorphous forms, for example as amorphous and crystalline polymorphous forms. All polymorphous forms of the compounds of the invention are included within the scope of the invention and are another aspect of the invention.

Compounds of formula (I) are preferred, wherein

A is A1;

R is unsubstituted or at least monosubstituted $C_1$-$C_{10}$-alkyl, aryl, aryl-($C_1$-$C_{10}$-alkyl)-, heterocyclyl, heterocyclyl-($C_1$-$C_{10}$-alkyl)-, $C_3$-$C_{10}$-cycloalkyl, polycycloalkyl, $C_2$-$C_{10}$-alkenyl or $C_2$-$C_{10}$-alkinyl, where the substituents are selected from halogen, —CN, $C_1$-$C_{10}$-alkyl, —NO$_2$, —OR1, —C(O)OR1, —O—C(O)R1, —NR1R2, —NHC(O)R1, —C(O)NR1R2, —SR1, —S(O)R1, —SO$_2$R1, —NHSO$_2$R1, —SO$_2$NR1R2, —C(S)NR1R2, —NHC(S)R1, —O—SO$_2$R1, —SO$_2$—O—R1 oxo, —C(O)R1, —C(NH)NH$_2$, heterocyclyl, $C_3$-$C_{10}$-cycloalkyl, aryl-($C_1$-$C_6$-alkyl)-, aryl, heteroaryl, trifluoromethyl, trifluioromethylsulfanyl and trifluoromethoxy, and aryl, heterocyclyl and heteroaryl may in turn be at least monosubstituted with $C_1$-$C_6$-alkyl, $C_1$-$C_6$-alkoxy, halogen, trifluoromethyl, trifluoromethoxy or OH;

R1 and R2, independently from each other, are hydrogen;

unsubstituted or at least monosubstituted $C_1$-$C_{10}$-alkyl, $C_3$-$C_{10}$-cycloalkyl, aryl, aryl-($C_1$-$C_{10}$-alkyl)-, $C_2$-$C_{10}$-alkenyl, $C_2$-$C_{10}$-alkinyl, heterocyclyl, heterocyclyl-($C_1$-$C_{10}$-alkyl)- or heteroaryl, where the substituents are selected from halogen, $C_1$-$C_6$-alkyl, $C_1$-$C_6$-alkoxy, CN, NO$_2$, NH$_2$, ($C_1$-$C_6$-alkyl) amino-, di($C_1$-$C_6$-alkyl)amino-, OH, COOH, —COO—($C_1$-$C_6$-alkyl), —CONH$_2$, formyl, trifluoromethyl and trifluoromethoxy;

heteroaryl is a 5 to 10-membered, aromatic, mono- or bicyclic heterocycle containing one or more heteroatoms selected from N, O and S;

aryl is phenyl, indanyl, indenyl or naphthyl; and heterocyclyl is a 5 to 10-membered, aliphatic, mono- or bicyclic heterocycle, containing one or more heteroatoms selected from N, O and S.

In another embodiment, compounds of formula (I) are preferred, wherein

R is unsubstituted or at least monosubstituted $C_1$-$C_{10}$-alkyl, aryl, aryl-($C_1$-$C_{10}$-alkyl)-, heterocyclyl, heterocyclyl-($C_1$-$C_{10}$-alkyl)-, $C_3$-$C_{10}$-cycloalkyl, heteroaryl or heteroaryl-($C_1$-$C_{10}$-alkyl)-, where the substituents are selected from halogen, —CN, $C_1$-$C_{10}$-alkyl, —NO$_2$, —OR1, —C(O)OR1, —O—C(O)R1, —NR1R2, —NHC(O)R1, —C(O)NR1R2, —SR1, —S(O)R1, —SO$_2$R1, —NHSO$_2$R1, —SO$_2$NR1R2, —C(S)NR1R2, —NHC(S)R1, —O—SO$_2$R1, —SO$_2$—O—R1, oxo, —C(O)R1, —C(NH)NH$_2$, heterocyclyl, $C_3$-$C_{10}$-cycloalkyl, aryl-($C_1$-$C_6$-alkyl)-, aryl, heteroaryl, trifluoromethyl, trifluoromethylsulfanyl and trifluoromethoxy, and aryl, heterocyclyl and heteroaryl may in turn be at least monosubstituted with $C_1$-$C_6$-alkyl, $C_1$-$C_6$-alkoxy, halogen, trifluoromethyl, trifluoroethoxy or OH;

R1 and R2, independently from each other, are hydrogen;

unsubstituted or at least monosubstituted $C_1$-$C_{10}$-alkyl, $C_3$-$C_{10}$-cycloalkyl, aryl, aryl-($C_1$-$C_{10}$-alkyl)-, $C_2$-$C_{10}$-alkenyl, $C_2$-$C_{10}$-alkinyl, heterocyclyl, heterocyclyl-($C_1$-$C_{10}$-alkyl)- or heteroaryl, where the substituents are selected from halogen, $C_1$-$C_6$-alkyl, $C_1$-$C_6$-alkoxy, CN, NO$_2$, NH$_2$, ($C_1$-$C_6$-alkyl)amino-, di($C_1$-$C_6$-alkyl)amino-, OH, COOH, —COO—($C_1$-$C_6$-alkyl), —CONH$_2$, formyl, trifluoromethyl and trifluoromethoxy;

heteroaryl is a 5 to 10-membered, aromatic, mono- or bicyclic heterocycle containing one or more heteroatoms selected from N, O and S;

aryl is phenyl, indanyl, indenyl or naphthyl; and heterocyclyl is a 5 to 10-membered, aliphatic, mono- or bicyclic heterocycle, containing one or more heteroatoms selected from N, O and S.

In another embodiment, compounds of formula (I) are preferred, wherein

Ar is unsubstituted or at least monosubstituted phenyl, pyridinyl, pyrimidinyl, pyrazolyl, thiophenyl, isoxazolyl, benzo[b]thiophenyl, benzodioxolyl or thiazolo[3,2-b][1,2,4]-thiazolyl, where the substituents are selected from halogen, —CN, NO$_2$, $C_1$-$C_{10}$-alkyl, —OR1, —C(O)OR1, —O—C(O)R1, —NR1R2, —NHC(O)R1, —C(O)NR1R2, —NHC(S)R1, —C(S)NR1R2, —SR1, —S(O)R1, —SO$_2$R1, —NHSO$_2$R1, —SO$_2$NR1R2, —O—SO$_2$R1, —SO$_2$—O—R1, aryl, heteroaryl, aryl-($C_1$-$C_6$-alkyl)-, formyl, trifluoromethyl and trifluoromethoxy, and aryl and heteroaryl may in turn be at least monosubstituted with $C_1$-$C_6$-alkyl, $C_1$-$C_6$-alkoxy, halogen, trifluoromethyl, trifluoromethoxy or OH;

R1 and R2, independently from each other, are hydrogen;

unsubstituted or at least monosubstituted $C_1$-$C_{10}$-alkyl, $C_3$-$C_{10}$-cycloalkyl, aryl, aryl-($C_1$-$C_{10}$-alkyl)-, $C_2$-$C_{10}$-alkenyl, $C_2$-$C_{10}$-alkinyl, heterocyclyl, heterocyclyl-($C_1$-$C_{10}$-alkyl)- or heteroaryl, where the substituents are selected from halogen, $C_1$-$C_6$-alkyl, $C_1$-$C_6$-alkoxy, CN, NO$_2$, NH$_2$, ($C_1$-$C_6$-alkyl) amino-, di($C_1$-$C_6$-alkyl)amino-, OH, COOH, —COO—($C_1$-$C_6$-alkyl), —CONH$_2$, formyl, trifluoromethyl and trifluoromethoxy;

heteroaryl is a 5 to 10-membered aromatic, mono- or bicyclic heterocycle, containing one or more heteroatoms selected from N, O and S;

aryl is phenyl, indanyl, indenyl or naphthyl; and heterocyclyl is a 5 to 10-membered aliphatic, mono- or bicyclic heterocycle, containing one or more heteroatoms selected from N, O and S.

Compounds of formula (I) are more preferred, wherein

A is A1;

R is unsubstituted or at least monosubstituted $C_1$-$C_{10}$-alkyl, aryl, aryl-($C_1$-$C_{10}$-alkyl)-, heterocyclyl, heterocyclyl-($C_1$-$C_{10}$-alkyl)-, $C_3$-$C_{10}$-cycloalkyl, heteroaryl or heteroaryl-($C_1$-$C_{10}$-alkyl)-, where the substituents are selected from halogen, $C_1$-$C_{10}$-alkyl, —OR1, —C(O)OR1, —NR1R2, —C(O)NR1R2, —SR1, —SO$_2$R1, —SO$_2$NR1R2, oxo, —C(O)R1, —C(NH)NH$_2$, heterocyclyl, $C_3$-$C_{10}$-cycloalkyl, aryl-($C_1$-$C_6$-alkyl)-, aryl, trifluoromethyl and trifluoromethoxy, and aryl, heterocyclyl and heteroaryl may in turn be at least monosubtituted with $C_1$-$C_6$-alkyl, $C_1$-$C_6$-alkoxy, halogen, trifluoromethyl, trifluoromethoxy or OH;

Ar is unsubstituted or at least monosubstituted phenyl, pyridinyl, pyrimidinyl, pyrazolyl, thiophenyl, isoxazolyl, benzo[b]thiophenyl, benzodioxolyl or thiazolo[3,2-b][1,2,4]-thiazolyl, where the substituents are selected from halogen, $C_1$-$C_{10}$-alkyl, —OR1, —C(O)OR1, —NR1R2, —C(O)NR1R2, aryl, heteroaryl, aryl-($C_1$-$C_6$-alkyl)-, trifluoromethyl and trifluoromethoxy, and aryl and heteroaryl may in turn be at least monosubsituted with $C_1$-$C_6$-alkyl, $C_1$-$C_6$-alkoxy, halogen, trifluoromethyl or OH;

R1 and R2, independently from each other, are hydrogen;

unsubstituted or at least monosubstituted $C_1$-$C_{10}$-alkyl, $C_3$-$C_{10}$-cycloalkyl, aryl, aryl-($C_1$-$C_{10}$-alkyl)-, heterocyclyl, heterocyclyl-($C_1$-$C_{10}$-alkyl)- or heteroaryl, where the substituents are selected from halogen, $C_1$-$C_6$-alkyl, $C_1$-$C_6$-alkoxy, $NH_2$, ($C_1$-$C_6$-alkyl)amino-, di($C_1$-$C_6$-alkyl)amino-, OH, trifluoromethyl and trifluoromethoxy;

heteroaryl is a 5 to 10-membered, aromatic, mono- or bicyclic heterocycle containing one or more heteroatoms selected from N, O and S; heteroaryl is preferably imidazolyl, thiophenyl, furanyl, isoxazolyl, pyridinyl, pyrimidinyl, 1,2,3,4-tetrahydrochinolinyl, benzoimidazolyl, indolyl or benzodioxolyl;

aryl is phenyl, indanyl, indenyl or naphthyl; aryl is preferably phenyl or naphthyl; and heterocyclyl is a 5 to 10-membered, aliphatic, mono- or bicyclic heterocycle containing one or more heteroatoms selected from N, O and S; heterocyclyl is preferably 2-oxo-azepanyl, tetrahydrofuranyl, 1,3-dioxolanyl, morpholinyl, piperazinyl or piperidinyl.

Compounds of formula (I) are even more preferred, wherein

A is A1;

R is unsubstituted or at least monosubstituted $C_1$-$C_{10}$-alkyl, aryl, aryl-($C_1$-$C_{10}$-alkyl)-, heterocyclyl, heterocyclyl-($C_1$-$C_{10}$-alkyl)-, $C_3$-$C_{10}$-cycloalkyl, heteroaryl or heteroaryl-($C_1$-$C_{10}$-alkyl)-, where the substituents are selected from halogen, $C_1$-$C_{10}$-alkyl, —OR1, —C(O)OR1, —NR1R2, —C(O)NR1R2, —SR1, —$SO_2$R1, —$SO_2$NR1R2, oxo, —C(O)R1, —C(NH)$NH_2$, heterocyclyl, $C_3$-$C_{10}$-cycloalkyl, aryl-($C_1$-$C_6$-alkyl)-, aryl, trifluoromethyl and trifluoromethoxy, and aryl, heterocyclyl and heteroaryl may in turn be at least monosubsituted with $C_1$-$C_6$-alkyl, $C_1$-$C_6$-alkoxy, halogen, trifluoromethyl, trifluoromethoxy or OH;

Ar is unsubstituted or at least monosubstituted phenyl, pyridinyl or pyrimidinyl, where the substituents are selected from halogen, $C_1$-$C_{10}$-alkyl, —OR1, —C(O)OR1, —NR1R2, —C(O)NR1R2, aryl, heteroaryl, aryl-($C_1$-$C_6$-alkyl)-, trifluoromethyl and trifluoromethoxy, and aryl and heteroaryl may in turn be at least monosubsituted with $C_1$-$C_6$-alkyl, $C_1$-$C_6$-alkoxy, halogen, trifluoromethyl or OH;

R1 and R2, independently from each other, are hydrogen;

unsubstituted or at least monosubstituted $C_1$-$C_{10}$-alkyl, $C_3$-$C_{10}$-cycloalkyl, aryl, aryl-($C_1$-$C_{10}$-alkyl)-, heterocyclyl, heterocyclyl-($C_1$-$C_{10}$-alkyl)- or heteroaryl, where the substituents are selected from halogen, $C_1$-$C_6$-alkyl, $C_1$-$C_6$-alkoxy, $NH_2$, ($C_1$-$C_6$-alkyl)amino-, di($C_1$-$C_6$-alkyl)amino-, OH, trifluoromethyl and trifluoromethoxy;

heteroaryl is a 5 to 10-membered, aromatic, mono- or bicyclic heterocycle containing one or more heteroatoms selected from N, O and S; heteroaryl is preferably imidazolyl, thiophenyl, furanyl, isoxazolyl, pyridinyl, pyrimidinyl, 1,2,3,4-tetrahydrochinolinyl, benzoimidazolyl, indolyl or benzodioxolyl;

aryl is phenyl, indanyl, indenyl or naphthyl; aryl is preferably phenyl or naphthyl; and heterocyclyl is a 5 to 10-membered, aliphatic, mono- or bicyclic heterocycle containing one or more heteroatoms selected from N, O and S; heterocyclyl is preferably 2-oxo-azepanyl, tetrahydrofuranyl, 1,3-dioxolanyl, morpholinyl, piperazinyl or piperidinyl.

Compounds of formula (I) are even much more preferred, wherein

A is A1;

R is unsubstituted or at least monosubstituted aryl-($C_1$-$C_6$-alkyl)- or heteroaryl-($C_1$-$C_6$-alkyl)-, where the substituents are selected from halogen, $C_1$-$C_6$-alkyl, —OH, —O-aryl, $C_1$-$C_6$-alkoxy, —O—($C_1$-$C_6$-alkylen)-N($C_1$-$C_6$-alkyl)$_2$, —C(O)OH, —C(O)O—($C_1$-$C_6$-alkyl), —$NH_2$, —N($C_1$-$C_6$-alkyl)$_2$, —NH($C_1$-$C_6$-alkyl), —NH($C_1$-$C_{10}$-cycloalkyl), —C(O)$NH_2$, —C(O)NH-heteroaryl, —C(O)NH—($C_1$-$C_6$-alkyl), —$SO_2$($C_1$-$C_6$-alkyl), —$SO_2NH_2$, —C(O)-heterocyclyl, —C(NH)$NH_2$, heterocyclyl, aryl-($C_1$-$C_6$-alkyl)-, aryl, trifluoromethyl, and trifluoromethoxy, and aryl, heterocyclyl and heteroaryl may in turn be at least monosubstituted with $C_1$-$C_3$-alkyl, $C_1$-$C_3$-alkoxy, fluorine, chlorine, bromine, trifluoromethyl, trifluoromethoxy or OH;

heteroaryl is imidazolyl, thiophenyl, furanyl, isoxazolyl, pyridinyl, pyrimidinyl, benzoimidazolyl, indolyl or benzodioxolyl;

aryl is phenyl or naphthyl; and heterocyclyl is morpholinyl, piperazinyl or piperidinyl.

In another embodiment, compounds of formula (I) are even much more preferred, wherein A is A1;

Ar is unsubstituted or at least monosubstituted phenyl, pyridin-4-yl or pyrimidin-4-yl, where the substituents are selected from halogen, $C_1$-$C_6$-alkyl, —OH, $C_1$-$C_6$-alkoxy, —C(O)OH, —C(O)O—($C_1$-$C_6$-alkyl), —$NH_2$, —N($C_1$-$C_6$-alkyl)$_2$, —NH($C_1$-$C_6$-alkyl), —NH($C_1$-$C_{10}$-cycloalkyl), —NH(heterocyclyl-($C_1$-$C_6$-alkyl-)), —NH(aryl-($C_1$-$C_6$-alkyl-)), —C(O)$NH_2$, —C(O)NH—($C_1$-$C_6$-alkyl), aryl, and heteroaryl, and aryl, heterocyclyl and heteroaryl may in turn be at least monosubstituted $C_1$-$C_3$-alkyl, $C_1$-$C_3$-alkoxy, fluorine, chlorine, bromine, trifluoromethyl, trifluoromethoxy or OH;

heteroaryl is pyridinyl or pyrimidinyl;

aryl is phenyl or naphthyl; and heterocyclyl is morpholinyl, piperazinyl or piperidinyl.

Compounds of formula (I) are particularly preferred, wherein

A is A1;

R is unsubstituted or at least monosubstituted benzyl, phenylethyl-, phenylpropyl-, pyridinylmethyl-, pyridinylethyl- or pyridinylpropyl-, where the substituents are selected from chlorine, bromine, fluorine, trifluoromethyl and carboxy;

Ar is unsubstituted or at least monosubstituted pyridin-4-yl, pyrimidin-4-yl or phenyl, where the substituents are selected from methylamino-, ethylamino-, propylamino-, butylamino-, hydroxy, methoxy, ethoxy, methyl, ethyl, propyl, (phenylethyl)amino-, benzylamino- and (morpholinylethyl)amino-.

Compounds of formula (I) are exceptionally preferred, which are chosen from 6-(2-butylamino-pyrimidin-4-yl)-3-oxo-2,3-dihydro-pyridazine-4-carboxylic acid (3-pyridin-3-yl-propyl)-amide, 6-(4-hydroxy-3-methoxy-phenyl)-3-oxo-2,3-dihydro-pyridazine-4-carboxylic acid (3-pyridin-3-yl-propyl)-amide, 6-(4-hydroxy-3,5-dimethyl-phenyl)-3-oxo-2,3-dihydro-pyridazine-4-carboxylic acid (3-pyridin-3-yl-propyl)-amide, 6-(4-hydroxy-phenyl)-3-oxo-2,3-dihydro-pyridazine-4-carboxylic acid (3-pyridin-3-yl-propyl)-amide, 6-(2-ethylamino-pyrimidin-4-yl)-3-oxo-2,3-dihydro-pyridazine-4-carboxylic acid 4-chloro-benzylamide, 6-(3-chloro-4-hydroxy-phenyl)-3-oxo-2,3-dihydro-pyridazine-4-carboxylic acid 4-chloro-benzylamide, 6-(4-hydroxy-3,5-dimethyl-phenyl)-3-oxo-2,3-dihydro-pyridazine-4-carboxylic acid 4-chloro-benzylamide, 4-({[6-(4-hydroxy-3,5-dimethyl-phenyl)-3-oxo-2,3-dihydro-pyridazine-4-carbonyl ]-amino}-methyl)-benzoic acid, 4-({[6-(4-hydroxy-3-methoxy-phenyl)-3-oxo-2,3-dihydro-pyridazine-4-carbonyl ]-amino}-methyl)-benzoic acid, 6-(2-butylamino-pyrimidin-4-yl)-3-oxo-2,3-dihydro-pyridazine-4-carboxylic acid (pyridin-3-yl-methyl)-amide, 6-(3-fluoro-4-hydroxy-phenyl)-3-oxo-2,3-dihydro-pyridazine-4-carboxylic acid 4-chloro-benzylamide, 6-(4-hydroxy-3-methyl-phenyl)-3-oxo-2,3-dihydro-pyridazine-4-carboxylic acid 4-chloro-benzylamide, 6-[2-(2-morpholin-4-yl-ethylamino)-pyrimidin-4-yl]-3-oxo-2,3-dihydro-pyridazine-4-carboxylic acid 4-chloro-benzylamide, 6-(4-hydroxy-3-methoxy-phenyl)-3-oxo-2,3-dihydro-pyridazine-4-carboxylic acid 4-chloro-benzylamide, 6-(2-methylamino-pyrimidin-4-yl)-3-oxo-2,3-dihydro-pyridazine-4-carboxylic acid 4-chloro-benzylamide, R-3-oxo-6-[2-(1-phenyl-ethylamino)-pyrimidin-4-yl]-2,3-dihydro-pyridazine-4-carboxylic acid (3-phenyl-propyl)-amide, 6-(4-hydroxy-phenyl)-3-oxo-2,3-dihydro-pyridazine-4-carboxylic acid 4-chloro-benzylamide, 3-oxo-6-pyridin-4-yl-N-[4-(trifluoromethyl)benzyl]-2,3-dihydropyridazine-4-carboxamide, 3-oxo-6-pyridin-4-yl-2,3-dihydro-pyridazine-4-carboxylic acid 4-bromo-benzylamide, 3-oxo-6-pyridin-4-yl-N-(pyridin-3-ylmethyl)-2,3-dihydro-pyridazine-4-carboxamide, N-(2,4-dichlorobenzyl)-3-oxo-6-pyridin-4-yl-2,3-dihydro-pyridazine-4-carboxamide, 3-oxo-6-pyridin-4-yl-2,3-dihydro-pyridazine-4-carboxylic acid 4-chloro-2-fluoro-benzylamide, and N-(4-chlorobenzyl)-3-oxo-6-pyridin-4-yl-2,3-dihydropyridazine-4-carboxamide.

It is explicitly indicated once more that also in case of the preferred, more preferred, even more preferred, even much more preferred, particularly preferred and exceptionally preferred compounds according to formula (I) the above-mentioned explanations also apply in respect of the salts, stereoisomers, prodrugs, N-oxides etc.; in particular, the respective physiologically acceptable salts are included.

The derivatives of formula (I) for which A=A1=CONHR may be obtained from compounds according to formula (II), where X is a functional group, preferably —OH, $C_1$-$C_{10}$-alkoxy, chloro or —O—C(O)—($C_1$-$C_{10}$-alkyl). The conversion with the amine (III) may be carried out using an inert solvent at 0 to 150° C.

In case X is OH, the compounds of formula (I) may be obtained by acylation of the amine derivatives, either using an acid chloride to be added beforehand or by reaction in the presence of an activating agent.

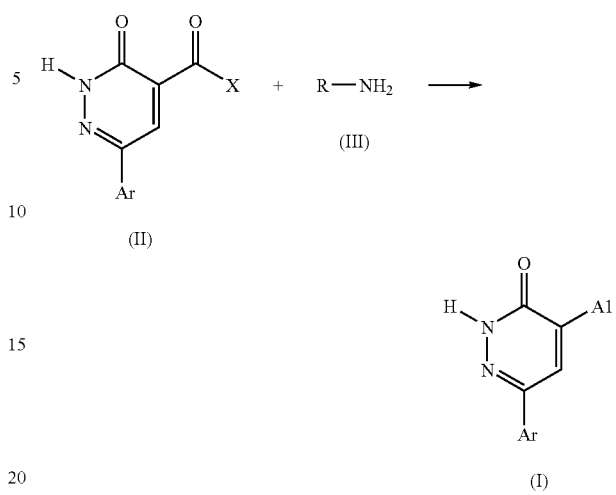

The reaction may be carried out by forming an acid chloride according to any methods known to persons skilled in the art or more precisely by the action of oxalyl chloride in toluene, dichloromethane (R. D. MILLER, J. Org. Chem, 56, (4) 1453, (1991)) which, thus formed, will react with the amine (III) in the presence of a base such as pyridine, triethylamine, diisopropylethylamine; the reaction can start at 0° C. and when the addition of the acid chloride is complete, the medium is kept stirred at room temperature (G. DAIDONE, Heterocycles, 43, (11), 2385-96, (1996)) or it is heated if necessary.

The reaction may also be carried out in the presence of an activating agent of the carbodiimide type alone (DCC, EDAC) (M. C. DESAI, Tetrahedron Lett., 34, 7685, (1993)) or in the presence of hydroxybenzotriazole and dimethylaminopyridine (J. P. GAMET, Tetrahedron, 40, 1995, (1984), K. BARLOS, J. Org. Chem., 50, 696, (1985)) or according to well known methods of coupling in peptide chemistry (M. BODANSZKY, Principles of Peptide Synthesis; Springer-Verlag, New York, N.Y., pages 9-58, (1984)) or of forming the amide bond.

The derivatives of formula (II) are obtained by the method described in patent FR 2481284 and by Y. Shojiro. Chem. Pharm. Bull., 19 (11) p. 2354. It is necessary to protect the reactive functional groups. The protecting groups are introduced according to any methods known to persons skilled in the art and in particular those described by T. W. GREENE, Protective Groups in Organic Synthesis, J. Wiley-Interscience Publication (1991). For the phenols, there will be preferably chosen more particularly a benzyl group introduced in the presence of an inorganic base such as sodium carbonate at the reflux temperature of acetone and of acetonitrile (A. R Mac Kenzie, Tetrahedron, 42, 3259, (1986)), which may then be removed by catalytic hydrogenation or more particularly using trifluoroacetic acid under reflux, described in patent WO 9727846.

The products of general formula (III) may be obtained commercially or by functionalization and protection of the reactive functional groups of commercially available products according to the methods described by Larock, Comprehensive Organic Transformations, VCH, New York, 1999. The nitrile functional groups are reduced with hydrogen in the presence of catalysts, $BH_3$ or more precisely lithium aluminum hydride in solvents such as dioxane or THF (T. M. Koening, Tetrahedron Letters, 35, 1339, (1994)). The phenol functional groups are protected with trimethylsilylethoxymethyl by reacting the starting compound with trimethylsilylethoxymethyl chloride in the presence of sodium hydride in a solvent such as dimethylformamide at room temperature (J. P. WHITTEN, J. Org. Chem., 51, 1891, (1986); M. P. EDWARDS, Tetrahedron, 42, 3723, (1986)). The deprotection is carried out according to methods known to persons skilled in the art and described by T. W. GREENE, Protective Groups in Organic Synthesis, J. Wiley-Interscience Publication (1991).

The derivatives of formula (I) for which the protecting group is trimethylsilylethoxymethyl can be deprotected by reaction with tetrabutylammonium fluoride under reflux in solvents such as tetrahydrofuran, dioxane. (J. P. WHITTEN, J. Org. Chem., 51, 1891, (1986); B. H. LIPSHUTZ, Tetrahedron Lett., 4095, (1986)).

The derivatives of formula (I) for which the protecting group is an ester can be saponified according to any methods known to persons skilled in the art and in particular by the action of sodium hydroxide on the reflux (L. Anzalone, J. Org. Chem., 50, 2128, (1985)).

For the derivatives in formula (I) for which A=A2=NHCOR, it is necessary to subject the derivatives of formula (II) to a rearrangement according to the methods described by Larock, Comprehensive Organic Transformations, VCH, New York, 1999 or more particularly by B. Singh, HETEROCYCLES, 31, (12), 2163, (1990).

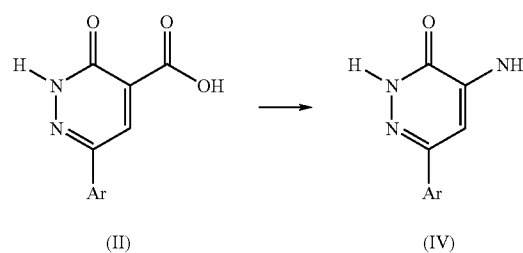

(II)  (IV)

The derivatives of formula (I) may be obtained according to route a) by acylating the derivatives of formula (IV) either using an acid chloride, or according to the route b) by acylating the derivatives of formula (IV) or using an anhydride, or according to the route c) by the reaction of an acid in the presence of an activating agent.

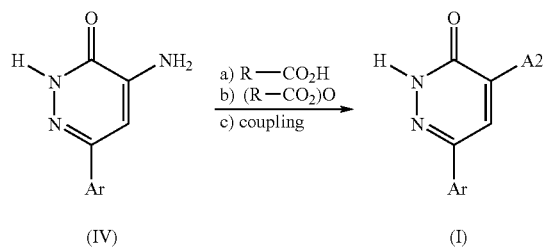

(IV)  (I)

By the route (a) the reaction is carried out in the presence of a base such as pyridine, triethylamine, diisopropylethylamine; the reaction may start at 0° C., and when the addition of the acid chloride is complete, the medium is kept stirred at room temperature (G. DAIDONE, Heterocycles, 43, (11), 2385-96, (1996)) or it is heated if necessary.

By the route (b) the reaction is carried out at the reflux temperature of an inert solvent such as xylene or tetrahydrofuran (F. ALBERICIO, Synth. Commun., 31, (2), 225-32, (2001)) or dichloromethane (G. PROCTER, Tetrahedron, 51, (47), 12837-842, (1995)) or in the anhydride itself.

By the route (c) the reaction is carried out in the presence of an activating agent of the carbodiimide type alone (DCC, EDAC) (M. C. DESAI, Tetrahedron Lett., 34, 7685, (1993)) or in the presence of hydroxybenzotriazole and dimethylaminopyridine (J. P. GAMET, Tetrahedron, 40, 1995, (1984), K. BARLOS, J. Org. Chem., 50, 696, (1985)) or according to well known methods of coupling in peptide chemistry (M. BODANSZKY, Principles of Peptide Synthesis; Springer-Verlag, New York, N.Y., pages 9-58, (1984)) or of forming the amide bond.

Furthermore, compounds according to general formula (I) can be prepared by palladium catalyzed coupling according to a reaction of Suzuki (I. Parrot et al., Synthesis; 7; 1163-1168, (1999)). A compound of formula (IV), where Y1 is halogen, $B(OH)_2$ or $Sn(C_1-C_{10}$-alkyl) and Y2 is H or a protecting group, is hereby converted with a compound of formula (V).

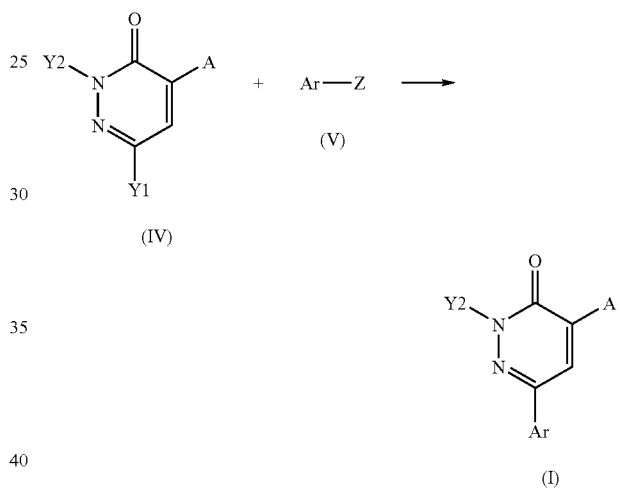

Z may be, for example, $B(OH)_2$, $B(C_1-C_{10}$-alkyl)$_2$, $Sn(C_1-C_{10}$-alkyl)$_3$, $Zn(C_1-C_{10}$-alkyl) or halogen. In case Y2 is a protecting group, said group is removed after the reaction of (IV) and (V) using methods known by a person skilled in the art. All protecting groups known by a person skilled in the art can be used as protecting groups, preferably trimethylsilylethoxymethyl-. For performing the palladium catalyzed coupling all palladium complexes known by a person skilled in the art can be employed, preferably Pd(t-riphenylphosphine)$_4$ (Pd-tetrakis-catalyst) is employed, which is preferably obtained in situ from palladium acetate.

The compounds of formula (I) are isolated and may be purified by known methods, for example by crystallization, chromatography or extraction.

A subject of the present invention is also the use of compounds according to the general formula (I) as pharmaceuticals or medicaments, respectively. With respect to the definition of the substituents A and Ar (as well as all further substituents defined by the before-mentioned substituents), the same explanations apply as laid out above in the context with the compounds as such.

The use of compounds according to the general formula (I) as a pharmaceutical, where the compounds have the above-mentioned preferred, more preferred, even more preferred, even much more preferred, in particular preferred or exceptionally preferred meaning, are also subject of the present invention.

The compounds of general formula (I) are kinase inhibitors and can therefore be employed for the treatment of diseases, which may result from an abnormal activity of kinases. As abnormal kinase activity, there may be mentioned, for example, that of PI3K, AkT, GSK-3β and the like.

In particular, compounds according to the present invention can be used for the inhibition of the kinase GSK-3β. This effect is particularly relevant for the treatment of metabolic diseases such as type II diabetes or neurodegenerative diseases such as Alzheimer's disease.

Furthermore, compounds according to the general formula (I) have an inhibitory effect in respect of the phosphorylation of the tau-protein. This effect is particularly relevant for the treatment of neurodegenerative diseases such as Alzheimer's disease.

Examples of diseases, which can be treated with the compounds according to the present invention, include: neurodegenerative diseases, strokes, cranial and spinal traumas and peripheral neuropathies, obesity, metabolic diseases, type II diabetes, essential hypertension, atherosclerotic cardiovascular diseases, polycystic ovary syndrome, syndrome X, immunodeficiency or cancer. Neurodegenerative diseases are preferably: Alzheimer's disease, Parkinson's disease, frontoparietal dementia, corticobasal degeneration and Pick's disease.

Compounds according to the present invention are preferably employed for the treatment of metabolic diseases, in particular of type II diabetes.

In another embodiment of the present invention, the compounds according to the general formula (I) are preferably employed for the treatment of neurodegenerative diseases, in particular of Alzheimer's disease.

In the above-mentioned explanation, the treatment also includes prophylaxis, therapy or curing of the above-mentioned diseases.

All references to "compound(s) according to formula (I)" refer hereinbelow to a compound/compounds of the formula (I) as described above and also to their salts, solvates and physiologically functional derivatives as described herein.

The compounds of the formula (I) can be administered to animals, preferably to mammals, and in particular to humans. The compounds of the formula (I) can be administered as pharmaceuticals by themselves, in mixtures with one another or in mixtures with other pharmaceuticals or in the form of pharmaceutical preparations. Further subjects of the present invention therefore also are the use of the compounds of the formula (I) for preparing one or more medicaments for prophylaxis and/or treatment of the before-mentioned diseases, pharmaceutical preparations (or pharmaceutical compositions) comprising an effective dose of at least one compound of the formula (I) as well as pharmaceutical preparations comprising an effective dose of at least one compound of the formula (I) for prophylaxis and/or treatment of the before-mentioned diseases.

The amount of a compound according to formula (I) which is required in order to attain the desired biological effect depends on a number of factors, for example the specific compound selected, the intended use, the type of administration and the clinical state of the patient. In general, the daily dose is in the range from 0.3 mg to 100 mg (typically from 3 mg to 50 mg) per day per kilogram of body weight, for example 3-10 mg/kg/day. An intravenous dose can be, for example, in the range from 0.3 mg to 1.0 mg/kg and can be administered in a suitable manner as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampoules for injections can contain, for example, from 1 mg to 100 mg, and orally administerable individual dose formulations such as, for example, tablets or capsules can contain, for example, from 1.0 to 1000 mg, typically from 10 to 600 mg. In the case of pharmaceutically acceptable salts, the above-mentioned masses relate to the mass of the free compound on which the salt is based. The compound used for the prophylaxis or therapy of the abovementioned conditions may be the compounds according to formula (I) themselves, but they are preferably present in the form of a pharmaceutical composition together with an acceptable carrier. The carrier must be naturally acceptable, in the sense that it is compatible with the other ingredients of said composition and is not harmful to the patient's health. The carrier may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions of the invention may be prepared according to any of the known pharmaceutical methods which essentially comprise mixing the ingredients with pharmacologically acceptable carriers and/or excipients.

Besides at least one compound according to formula (I) as well as one or more carriers, the pharmaceutical preparations can also contain additives. As additives can be employed, for example: fillers, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The pharmaceutical compositions of the invention may be in form of a pill, tablet, lozenge, coated tablet, granule, capsule, hard or soft gelatin capsule, aqueous solution, alcoholic solution, oily solution, syrup, emulsion suspension pastille suppository, solution for injection or infusion, ointment, tincture, cream, lotion, powder, spray, transdermal therapeutic systems, nasal spray, aerosol mixture, microcapsule, implant, rod or plaster.

Pharmaceutical compositions of the invention are those which are suitable for oral, rectal, topical, peroral (e.g. sublingual) and parenteral (e.g. subcutaneous, intramuscular, intradermal or intravenous) administration, although the most suitable manner of administration depends in each individual case on the nature and severity of the condition to be treated and on the nature of the compound according to formula (I) used in each case. Sugar-coated formulations and sugar-coated delayed-release formulations, too, are included within the scope of the invention. Preference is given to acid-resistant and enteric formulations. Suitable enteric coatings include cellulose acetate phthalate, polyvinyl acetate phthalate, hydroxypropyl-methylcellulose phthalate and anionic polymers of methacrylic acid and methyl methacrylate.

Suitable pharmaceutical compounds for oral administration may be present in separate units as, for example, capsules, cachets, lozenges or tablets, which in each case contain a particular amount of the compound according to formula (I); as powders (gelatin capsules or cachets) or granules; as solution or suspension in an aqueous or non-aqueous liquid; or as an oil-in-water or water-in-oil emulsion. As already mentioned, said compositions can be prepared according to any suitable pharmaceutical method which includes a step in which the active compound and the carrier (which may comprise one or more additional components) are contacted. In general, the compositions are prepared by uniform and homogeneous mixing of the active compound with a liquid and/or finely dispersed solid carrier, after which the product is shaped, if necessary. Thus a tablet, for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine. As diluents can be used, for example, starch, cellulose, saccharose, lactose or silica. The pharmaceutical compositions of the invention may also comprise substances other than diluents, for example one or more lubricants such as magnesium stearate or talc, a coloring, a coating (sugar-coated tablets) or a varnish.

Pharmaceutical compositions which are suitable for per-oral (sublingual) administration include lozenges which contain a compound according to formula (I) with a flavoring, usually sucrose and gum arabic or tragacanth, and pastilles which comprise the compound in an inert base such as gelatin and glycerol or sucrose and gum arabic.

Suitable pharmaceutical compositions for parenteral administration preferably comprise sterile aqueous preparations of a compound according to formula (I) which are preferably isotonic with the blood of the intended recipient. These preparations are preferably administered intravenously, although they may also be administered subcutaneously, intramuscularly or intradermally as an injection. Said preparations may preferably be prepared by mixing the compound with water and rendering the obtained solution sterile and isotonic with the blood. Injectable compositions of the invention generally contain from 0.1 to 5% by weight of the active compound.

These sterile compositions for parenteral administration may be preferably solutions which are aqueous or non aqueous, suspensions or emulsions. As solvent or vehicle, there may be used water, propylene glycol, polyethylene glycol, vegetable oils, in particular olive oil, organic esters for injection, for example, ethyl oleate or other suitable organic solvents. These compositions may also contain adjuvants, in particular wetting, isotonizing, emulsifying, dispersing and stabilizing mediums. The sterilization may be carried out in several ways, for example by an aseptic filtration, by incorporating sterilizing agents into the composition, by irradiation or by heating. They may also be prepared in the form of sterile solid compositions which may be dissolved at the time of use in sterile water or in any other sterile medium for injection.

Suitable pharmaceutical compositions for rectal administration are preferably present as individual dose suppositories. These may be prepared by mixing a compound according to formula (I) with one or more conventional solid carriers, for example cocoa butter, and shaping the resulting mixture.

Suitable pharmaceutical compositions for topical application to the skin are preferably present as ointment, cream, lotion, paste, spray, aerosol or oil. Carriers which may be used are petroleum jelly, lanolin, polyethylene glycols, alcohols and combinations of two or more of these substances. In general, the active compound is present at a concentration of from 0.1 to 15%, for example from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from approx. 1% to 35%, preferably approx. 3% to 15%. A particular possibility is the release of the active compound by electrotransport or iontophoresis, as described, for example, in Pharmaceutical Research, 2(6): 318 (1986).

The following examples illustrate compositions according to the invention:

EXAMPLE A

Gelatin capsules containing a dose of 50 mg of active product and having the following composition were prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing a dose of 50 mg of active product and having the following composition were prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |

Mixture of hydroxymethylcellulose, glycerin, titanium oxide (72-3.5-24.5) qs 1 finished film-coated tablet of 245 mg.

EXAMPLE C

A solution for injection containing 10 mg of active product and having the following composition was prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol at 95% | 0.4 ml |
| Sodium hydroxide | 24 mg |

-continued

| Propylene glycol | 1.6 ml |
| Water | qs 4 ml |

Another subject of the present invention is the combination of compounds of the formula (I) with other pharmaceutically active substances not covered by formula (I).

The compounds of the formula (I) are distinguished by beneficial actions on the metabolism of lipids, and they are particularly suitable for weight reduction and, after weight reduction, for maintaining a reduced weight in mammals and as anorectic agents. The compounds are distinguished by their low toxicity and their few side effects.

The compounds may be employed alone or in combination with other weight-reducing or anorectic active compounds. Further anorectic active compounds of this kind are mentioned, for example, in the Rote Liste, Chapter 01 under weight-reducing agents/appetite suppressants, and may also include those active compounds which increase the energy turnover of the organism and thus lead to weight reduction or else those which influence the general metabolism of said organism such that increased calorie intake does not cause an enlargement of the fat depots and a normal calorie intake causes a reduction in the fat depots of said organism. The compounds are suitable for the prophylaxis and, in particular, for the treatment of problems of excess weight or obesity.

The compounds of formula (I) have a beneficial effect on the glucose metabolism, they particularly lower the blood-sugar level and can be used for treatment of type I and type II diabetes. The compounds can therefore be used alone or in combination with other blood-sugar lowering active compounds (antidiabetics). In a further aspect of the invention, the compounds of the formula I may be administered in combination with one or more further pharmacologically active substances which may be selected, for example, from antidiabetics, antiadipose agents, blood-pressure-lowering active compounds, lipid reducers and active compounds for the treatment and/or prevention of complications caused by diabetes or associated with diabetes.

Suitable antidiabetics include insulins, amylin, GLP-1 and GLP-2 derivatives such as those disclosed by Novo Nordisk A/S in WO 98/08871 and also oral hypoglycemic active compounds.

Said oral hypoglycemic active compounds preferably include sulfonyl ureas, biguanidines, meglitinides, oxadiazolidinediones, thiazolidinediones, glucosidase inhibitors, glucagon receptor antagonists, GLP-1 agonists, potassium channel openers such as, for example, those disclosed by Novo Nordisk A/S in WO 97/26265 and WO 99/03861, insulin sensitizers, activators of insulin receptor kinase, inhibitors of liver enzymes involved in the stimulation of gluconeogenesis and/or glycogenolysis, for example, glycogen phosphorase inhibitors, modulators of glucose uptake and glucose elimination, lipid metabolism-modifying compounds such as antihyperlipidemic active compounds and antilipidemic active compounds, for example, HMGCoA-reductase inhibitors, inhibitors of cholesterol transport/cholesterol uptake, inhibitors of the reabsorption of bile acid or inhibitors of microsomal triglyceride transfer protein (MTP), compounds which reduce food intake, PPAR and RXR agonists and active compounds which act on the ATP-dependent potassium channel of beta cells.

In one embodiment of the present invention, the present compounds are administered in combination with insulin.

In another embodiment, the compounds of the invention are administered in combination with a sulfonylurea such as tolbutamide, glibenclamide, glimepiride, glipizide, gliquidone, glisoxepide, glibornuride or gliclazide. In another embodiment, the compounds of the present invention are administered in combination with a biguanidine such as metformin. In another embodiment, the compounds of the present invention are administered in combination with a meglitinide such as repaglinide. In yet another embodiment, the compounds of the present invention are administered in combination with a thiazolidinedione such as troglitazone, ciglitazone, pioglitazone, rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In another embodiment, the compounds of the present invention are administered in combination with an α-glucosidase inhibitor such as miglitol or acarbose.

In another embodiment, the compounds of the present invention are administered in combination with an active compound which acts on the ATP-dependent potassium channel of the beta cells, such as tolbutamide, glibenclamide, glimepiride, glipizide, gliclazide or repaglinide. In yet another embodiment, the compounds of the present invention are administered in combination with an antihyperlipidemic active compound or an antilipidemic active compound such as cholestyramine, colestipol, clofibrate, fenofibrate, gemfibrozil, lovastatin, pravastatin, simvastatin, atorvastatin, cerivastatin, fluvastatin, probucol, ezetimibe or dextrothyroxine.

In another embodiment, the compounds of the present invention are administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

Furthermore, the compounds of the invention may be administered in combination with one or more antiadipose agents or appetite-controlling active compounds.

Such active compounds may be selected from CART agonists, NPY antagonists, MC4 agonists, orexin antagonists, H3 agonists, TNF agonists, CRF agonists, CRF BP antagonists, urocortin agonists, β3 agonists, MSH (melanocyte-stimulating hormone) agonists, CCK agonists, serotonin re-uptake inhibitors, mixed serotonin and noradrenalin reuptake inhibitors, 5HT modulators, MAO inhibitors, bombesin agonists, galanin antagonists, growth hormone, growth-hormone-releasing compounds, TRH agonists, uncoupling protein 2 or 3 modulators, leptin agonists, dopamine agonists (bromocriptine, doprexin), lipase/amylase inhibitors, cannabinoid receptor 1 antagonists, modulators of acylation-stimulating protein (ASP), PPAR modulators, RXR modulators, hCNTF mimetics or TR-β agonists.

In one embodiment of the invention, the antiadipose agent is leptin or modified leptin. In another embodiment, the antiadipose agent is dexamphetamine or amphetamine. In another embodiment, the antiadipose agent is fenfluramine or dexfenfluramine. In yet another embodiment, the antiadipose agent is sibutramine or the mono- and bis-demethylated active metabolite of sibutramine. In another embodiment, the antiadipose agent is orlistate. In another embodiment, the antiadipose agent is mazindol, diethylpropione or phentermine.

Furthermore, the compounds of the present invention may be administered in combination with one or more antihypertensive active compounds. Examples of antihypertensive active compounds are betablockers such as alprenolol, atenol, timolol, pindolol, propanolol and metoprolol, ACE (angiotensin-converting enzyme) inhibitors such as benazepril, captopril, enalapril, fosinopril, lisinopril, quinapril and rampril, calcium channel blockers such as nifedipine, felodipine, nicardipine, isradipine, nimodipine, diltiazem and verapamil, and also alphablockers such as doxazosin, urapidil, prazosin and terazosin. Furthermore, reference may be made to Remington: The Science and Practice of Pharmacy, 19th edition, Gennaro, editor, Mack Publishing Co., Easton, Pa., 1995.

It is self-evident that every suitable combination of the compounds of the invention with one or more of the aforementioned compounds and optionally one or more other pharmacologically active substances is to be regarded as covered by the scope of protection of the present invention.

The following examples illustrate the invention without limitation.

EXAMPLE 1

N-(2,4-dichlorobenzyl)-3-oxo-6-phenyl-4-yl-2,3-dihydropyridazine-4-carboxamide

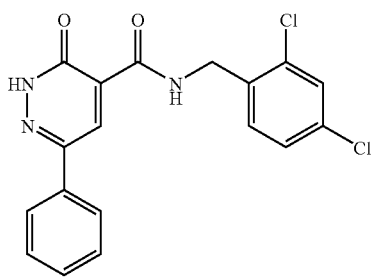

0.14 g of 1-hydroxybenzotriazole, 0.14 cm³ of 2,4-dichlorobenzylamine and 0.14 cm³ of triethylamine were added to 0.2 g of 3-oxo-6-phenyl-2,3-dihydro-pyridazine-4-carboxylic acid prepared as described by Y. Shojiro et al., Chem. Pharm. Bull; 19, (11), p. 2354, in 10 cm³ of dichloromethane. 0.2 g of 1-(3-dimethylaminopropyl)-3-ethylcarbodiimide hydrochloride was then added. The mixture was stirred for 48 hours at 19° C. 10 cm³ of distilled water were added. The organic phase was washed again with 3 times 10 cm³ of aqueous normal hydrochloric acid solution and then with 10 cm³ of saturated aqueous sodium chloride solution. The organic phase was then dried over magnesium sulfate. The mixture was filtered through a sinter funnel and then evaporated under reduced pressure (2 kPa; 45° C.). The residue was taken up with 10 cm³ of diisopropyl ether. The insoluble material was filtered off through a sinter funnel and then rinsed again with 10 cm³ of diisopropyl ether. After drying (10 kPa; 20° C.), 28 mg of N-(2,4-dichlorobenzyl)-3-oxo-6-phenyl-4-yl-2,3-dihydro-pyridazine-4-carboxamide were obtained in the form of a cream-colored solid melting at about 258° C.

¹H NMR spectrum (300 MHz, (CD₃)₂SO d6, δ in ppm): 4.64 (d, J=6 Hz: 2H); from 7.40 to 7.60 (mt: 5H); 7.66 (broad s: 1H); 7.92 (mt: 2H); 8.55 (s: 1H); 10.04 (broad t, J=6 Hz: 1H); from 13.80 to 14.15 (broad unresolved peak: 1H).

[M+1]-peak: 374

EXAMPLE 2

N-(2,4-dichlorobenzyl)-3-oxo-6-pyridin-4-yl-2,3-dihydropyridazine-4-carboxamide

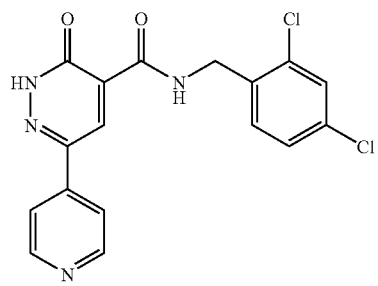

0.02 cm³ of dimethylformamide and then 0.12 cm³ of oxalyl chloride were added to 0.3 g of 3-oxo-6-(pyridin-4-yl)-2,3-dihydropyridazine-4-carboxylic acid prepared as described in patent FR 2 481 284, dissolved in 10 cm³ of dichloromethane. The reaction medium was stirred for 3 hours at 19° C. A further 0.12 cm³ of oxalyl chloride was then added and the mixture was stirred for a further one hour at 19° C. The reaction mixture was then poured onto a solution of 10 cm³ of dichloromethane containing 0.19 cm³ of triethylamine and 0.21 cm³ of 2,4-dichlorobenzylamine. The reaction medium was stirred for 12 hours at 19° C. and then filtered through a sinter funnel, rinsed with 10 cm³ of dichloromethane, 10 cm³ of distilled water and with 10 cm³ of aqueous normal hydrochloric acid solution. After drying (10 kPa; 20° C.), 0.25 g of N-(2,4-dichlorobenzyl)-3-oxo-6-pyridin-4-yl-2,3-dihydropyridazine-4-carboxamide was obtained in the form of a white solid melting at 233° C.

¹H NMR spectrum (300 MHz, (CD₃)₂SO d6, δ in ppm): 4.64 (d, J=6 Hz: 2H); 7.45 (mt: 2H); 7.66 (broad s: 1H); 7.91 (broad d, J=5 Hz: 2H); 8.62 (s: 1H); 8.73 (broad d, J=5 Hz: 2H); 9.95 (broad t, J=6 Hz: 1H); 14.25 (unresolved peak: 1H).

[M+1]-peak: 375,03

EXAMPLE 3

N-benzyl-3-oxo-6-pyridin-4-yl-2,3-dihydropyridazine-4-carboxamide

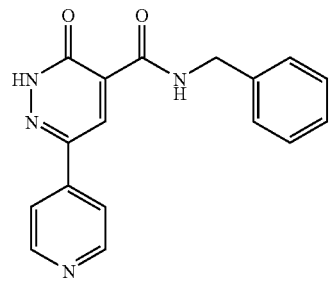

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm³ of dichloromethane, 0.02 cm³ of dimethylformamide, 0.12 cm³ of oxalyl chloride, 0.17 cm³ of benzylamine and 0.19 cm³ of triethylamine, 0.22 g of N-benzyl-3-oxo-6-pyridin-4-yl-2,3-dihydropyridazine-4-carboxamide was obtained in the form of a cream-colored solid melting at 258° C.

$^1$H NMR spectrum (300 MHz, (CD$_3$)$_2$SO d6, δ in ppm): 4.61 (d, J=6 Hz: 2H); from 7.25 to 7.45 (mt: 5H); 7.92 (broad d, J=6 Hz: 2H); 8.64(s: 1H); 8.73 (broad d, J=6 Hz: 2H); 9.93 (broad t, J=6 Hz: 1H).

[M+1]-peak: 307

EXAMPLE 4

N-(4-chlorobenzyl)-3-oxo-6-pyridin-4-yl-2,3-dihydropyridazine-4-carboxamide

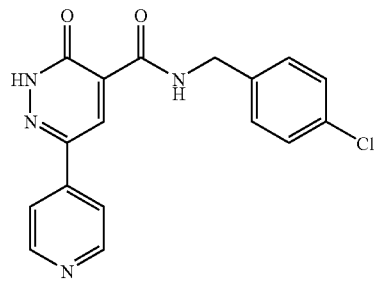

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm³ of dichloromethane, 0.02 cm³ of dimethylformamide, 0.12 cm³ of oxalyl chloride, 0.19 cm³ of 4-chlorobenzylamine and 0.19 cm³ of triethylamine, 0.2 g of N-(4-chlorobenzyl)-3-oxo-6-pyridin-4-yl-2,3-dihydropyridazine-4-carboxamide was obtained in the form of a cream-colored solid melting at 250° C.

$^1$H NMR spectrum (300 MHz, (CD$_3$)$_2$SO d6, δ in ppm): 4.60 (d, J=6 Hz: 2H); 7.41 (mt: 4H); 7.92 (broad d, J=6 Hz: 2H); 8.64 (s: 1H); 8.73 (broad d, J=6 Hz: 2H); 9.91 (broad t, J=6 Hz: 1H).

[M+1]-peak: 341

EXAMPLE 5

N-(2-chlorobenzyl)-3-oxo-6-pyridin-4-yl-2,3-dihydropyridazine-4-carboxamide

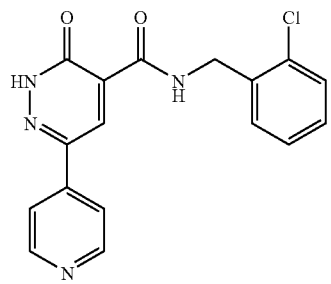

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm³ of dichloromethane, 0.02 cm³ of dimethylformamide, 0.12 cm³ of oxalyl chloride, 0.19 cm³ of 2-chlorobenzylamine and 0.19 cm³ of triethylamine, 0.25 g of N-(2-chlorobenzyl)-3-oxo-6-pyridin-4-yl-2,3-dihydropyridazine-4-carboxamide was obtained in the form of a white solid melting above 260° C.

$^1$H NMR spectrum (300 MHz, (CD$_3$)$_2$SO d6, δ in ppm): 4.67 (d, J=6 Hz: 2H); 7.35 (mt: 2H); from 7.40 to 7.55 (mt: 2H); 7.92 (broad d, J=6 Hz: 2H); 8.63 (s: 1H); 8.72 (broad d, J=6 Hz: 2H); 9.95 (broad t, J=6 Hz: 1H); 14.25 (s: 1H).

[M+1]-peak: 341

EXAMPLE 6

N-[2-(2,4-dichlorophenyl)ethyl]-3-oxo-6-pyridin-4-yl-2,3-dihydropyridazine-4-carboxamide

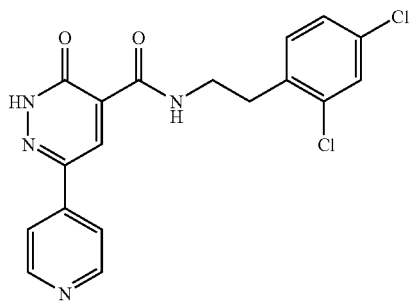

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm³ of dichloromethane, 0.02 cm³ of dimethylformamide, 0.12 cm³ of oxalyl chloride, 0.23 cm³ of 2,4-dichlorophenylethylamine and 0.19 cm³ of triethylamine, 0.23 g of N-[2-(2,4-dichlorophenyl)ethyl]-3-oxo-6-pyridin-4-yl-2,3-dihydropyridazine-4-carboxamide was obtained in the form of a cream-colored solid melting at 202° C.

$^1$H NMR spectrum (300 MHz, (CD$_3$)$_2$SO d6, δ in ppm): 3.00 (t, J=7 Hz: 2H); 3.63 (q, J=7 Hz: 2H); 7.38 (dd, J=8.5 and 2 Hz: 1H); 7.44 (d, J=8 Hz: 1H); 7.60 (d, J=2 Hz: 1H); 7.90 (d mt, J=6 Hz: 2H); 8.49 (s: 1H); 8.68 (d mt, J=6 Hz: 2H); 9.96 (unresolved peak: 1H); from 13.50 to 14.50 (very broad unresolved peak: 1H).

[M+1]-peak: 389

EXAMPLE 7

N-(2,4-dichlorophenyl)-3-oxo-6-pyridin-4-yl-2,3-dihydropyridazine-4-carboxamide

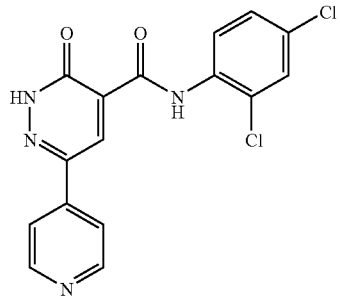

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm³ of dichloromethane, 0.02 cm³ of dimethylformamide, 0.12 cm³ of oxalyl chloride, 0.036 g of 2,4-dichloroaniline and 0.19 cm³ of triethylamine, 0.16 g of N-(2,4-dichlorophenyl)-3-oxo-6-pyridin-4-yl-2,3-dihydropyridazine-4-carboxamide was obtained in the form of a cream-colored solid melting above 260° C.

$^1$H NMR spectrum (400 MHz, (CD$_3$)$_2$SO d6 with addition of a few drops of CD$_3$COOD d4, δ in ppm): 7.52 (dd, J=8.5 and 2.5 Hz: 1H); 7.75 (d, J=2.5 Hz: 1H); 7.96 (d mt, J=6 Hz: 2H); 8.60 (d, J=8.5 Hz: 1H); 8.75 (broad d, J=6 Hz: 2H); 8.77 (s: 1H).

[M+1]-peak: 361

EXAMPLE 8

3-oxo-6-pyridin-4-yl-N-(pyridin-4-ylmethyl)-2,3-dihydropyridazine-4-carboxamide

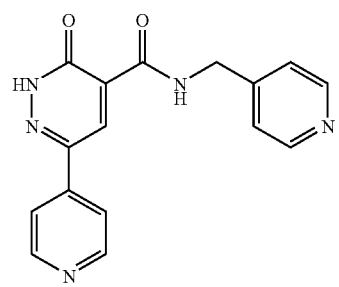

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm³ of dichloromethane, 0.02 cm³ of dimethylformamide, 0.12 cm³ of oxalyl chloride, 0.15 cm³ of 4-(aminomethyl)pyridine and 0.19 cm³ of triethylamine, 0.14 g of 3-oxo-6-pyridin-4-yl-N-(pyridin-4-ylmethyl)-2,3-dihydropyridazine-4-carboxamide was obtained in the form of a cream-colored solid melting at 254° C.

$^1$H NMR spectrum (300 MHz, (CD$_3$)$_2$SO d6, δ in ppm): 4.63 (d, J=6 Hz: 0.2H); 7.35 (broad d, J=6 Hz: 2H); 7.92 (d mt, J=6 Hz: 2H); 8.53 (broad d, J=6 Hz: 2H); 8.62 (s: 1H); 8.72 (broad d, J=6 Hz: 2H); 9.99 (t, J=6 Hz: 1H); 14.26 (unresolved peak: 1H).

[M+1]-peak: 308

EXAMPLE 9

3-oxo-6-pyridin-4-yl-N-[3-(trifluoromethyl)benzyl]-2,3-dihydropyridazine-4-carboxamide

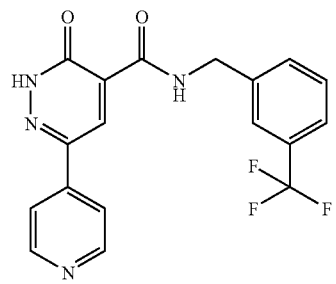

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm³ of dichloromethane, 0.02 cm³ of dimethylformamide, 0.12 cm³ of oxalyl chloride, 0.21 cm³ of 3-(trifluoromethyl)benzylamine and 0.19 cm³ of triethylamine, 0.22 g of 3-oxo-6-pyridin-4-yl-N-[3-(trifluoromethyl)benzyl]-2,3-dihydropyridazine-4-carboxamide was obtained in the form of a cream-colored solid melting at 224° C.

$^1$H NMR spectrum (300 MHz, (CD$_3$)$_2$SO d6, δ in ppm): 4.68 (d, J=6 Hz: 2H); from 7.55 to 7.75 (mt: 3H); 7.74 (broad s: 1H); 7.91 (d mt, J=6 Hz: 2H); 8.63 (s: 1H); 8.72 (d mt, J=6 Hz: 2H); 9.96 (broad t, J=6 Hz: 1H); 14.21 (unresolved peak: 1H).

[M+1]-peak: 375

EXAMPLE 10

3-oxo-6-pyridin-4-yl-N-[4-(trifluoromethyl)benzyl]-2,3-dihydropyridazine-4-carboxamide

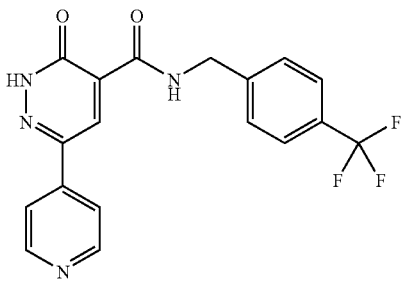

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm³ of dichloromethane, 0.02 cm³ of dimethylformamide, 0.12 cm³ of oxalyl chloride, 0.21 cm³ of 4-(trifluoromethyl)benzylamine and 0.19 cm³ of triethylamine, 0.22 g of 3-oxo-6-pyridin-4-yl-N-[4-(trifluoromethyl)benzyl]-2,3-dihydropyridazine-4-carboxamide was obtained in the form of a cream-colored solid melting at 227° C.

$^1$H-NMR spectrum (300 MHz, (CD$_3$)$_2$SO d6, δ in ppm): 4.69 (d, J=6 Hz: 2H); 7.59 (broad d, J=8 Hz: 2H); 7.73 (broad d, J=8 Hz: 2H); 7.91 (d mt, J=6 Hz: 2H); 8.62 (s: 1H); 8.72 (d mt, J=6 Hz: 2H); 10.04 (very broad t, J=6 Hz: 1H); 14.24 (unresolved peak: 1H).

[M+1]-peak: 375

EXAMPLE 11

N-(3,5-dichlorobenzyl)-3-oxo-6-pyridin-4-yl-2,3-dihydropyridazine-4-carboxamide

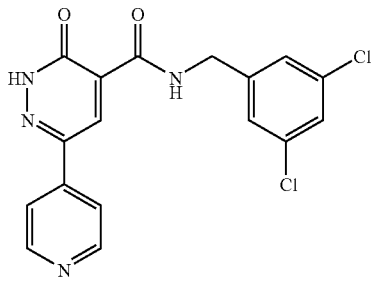

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm$^3$ of dichloromethane, 0.02 cm$^3$ of dimethylformamide, 0.12 cm$^3$ of oxalyl chloride, 0.19 cm$^3$ of 3,5-dichlorobenzylamine and 0.19 cm$^3$ of triethylamine, 0.025 g of N-(3,5-dichlorobenzyl)-3-oxo-6-pyridin-4-yl-2,3-dihydropyridazine-4-carboxamide was obtained in the form of a white solid melting above 260° C.

$^1$H NMR spectrum (300 MHz, (CD$_3$)$_2$SO d6, δ in ppm): 4.59 (d, J=6 Hz: 2H); 7.43 (mt: 2H); 7.51 (mt: 1H); 7.91 (d mt, J=6 Hz: 2H); 8.57 (s: 1H); 8.70 (d mt, J=6 Hz: 2H); 10.14 (unresolved peak: 1H); 14.18 (broad unresolved peak: 1H).

[M+1]-peak: 375

EXAMPLE 12

3-oxo-6-pyridin-4-yl-N-(n-butyl)-2,3-dihydropyridazine-4-carboxamide

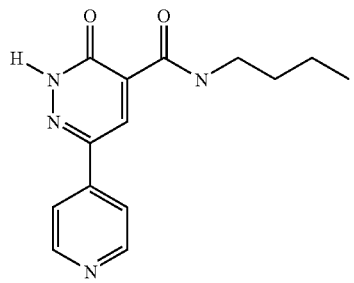

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-4-yl-2,3-dihydropyridazine-4-carboxylic acid, 10 cm$^3$ of dichloromethane, 0.02 cm$^3$ of dimethylformamide, 0.12 cm$^3$ of oxalyl chloride, 0.15 cm$^3$ of n-butylamine and 0.19 cm$^3$ of triethylamine, and after purification by chromatography on silica gel (particle size 40-63 μm, under an argon pressure of 150 kPa), eluting with a mixture of dichloromethane and methanol (97.5/2.5 by volume), 0.23 g of 3-oxo-6-pyridin-4-yl-N-(n-butyl)-2,3-dihydropyridazine-4-carboxamide was obtained in the form of a white solid melting at 209° C.

$^1$H NMR spectrum (300 MHz, (CD$_3$)$_2$SO d6, δ in ppm): 0.93 (t, J=7 Hz: 3H); 1.38 (mt: 2H); 1.55 (mt: 2H); 3.37 (mt: 2H); 7.90 (d mt, J=6 Hz: 2H); 8.60 (s: 1H); 8.72 (broad d, J=6 Hz: 2H); 9.50 (t, J=6 Hz: 1H); 14.20 (unresolved peak: 1H).

[M+1]-peak: 273

Example 13

Ethyl 3-[(3-oxo-6-pyridin-4-yl-2,3-dihydropyridazine-4-carbonyl)amino]propionate

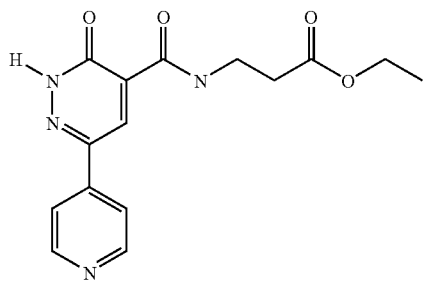

0.733 g of 1-hydroxybenzotriazole, 0.833 g of β-alanine ethyl ester hydrochloride, 0.96 cm$^3$ of N,N-diisopropylethylamine and 2.06 g of O-(7-azabenzotriazol-1-yl)-N,N,N',N'-tetramethyluronium hexafluorophosphate were successively added to 0.94 g of 3-oxo-6-pyridin-4-yl-2,3-dihydropyridazine-4-carboxylic acid dissolved in 100 cm$^3$ of N,N-dimethylformamide. The reaction medium was stirred for 12 hours at 19° C. The solvent was evaporated off under reduced pressure (2 kPa; 55° C.). The solid residue was triturated in 20 cm$^3$ of dichloromethane, suction-filtered and oven-dried under reduced pressure (10 kPa; 20° C.). After purification by chromatography on silica gel (particle size 40-63 μm, under an argon pressure of 150 kPa) eluting with dichloromethane, 0.45 g of ethyl 3-[(3-oxo-6-pyridin-4-yl-2,3-dihydropyridazine-4-carbonyl)amino]propionate was obtained in the form of a white solid melting at 180° C.

$^1$H NMR spectrum (300 MHz, (CD3)$_2$SO d6, δ in ppm): 1.22 (t, J=7 Hz: 3H); 2.63 (broad t, J=6.5 Hz: 2H); 3.62 (q, J=6.5 Hz: 2H); 4.12 (q, J=7 Hz: 2H); 7.92 (broad d, J=6 Hz: 2H); 8.61 (s: 1H); 8.73 (broad d, J=6 Hz: 2H); 9.69 (broad t, J=6.5 Hz: 1H).

[M+1]-peak: 317

EXAMPLE 14

3-oxo-6-pyridin-4-yl-N-(pyridin-3-ylmethyl)-2,3-dihydropyridazine-4-carboxamide

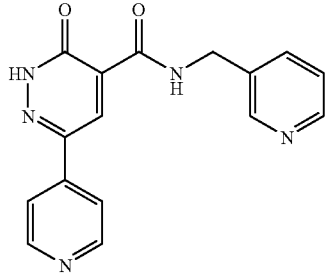

Working as in example 13 for the preparation of ethyl 3-[(3-oxo-6-pyridin-4-yl-2,3-dihydropyridazine-4-carbonyl)amino]propionate, but starting with 0.3 g of 3-oxo-6-pyridin-4-yl-2,3-dihydropyridazine-4-carboxylic acid, 30 cm³ of N,N-dimethylformamide, 0.233 g of 1-hydroxybenzotriazole, 0.18 cm³ of 3-(aminomethyl)pyridine, 0.31 cm³ of N,N-diisopropylethylamine and 0.65 g of O-(7-azabenzotriazol-1-yl)-N,N,N',N'-tetramethyluronium hexafluorophosphate, 0.046 g of 3-oxo-6-pyridin-4-yl-N-(pyridin-3-ylmethyl)-2,3-dihydropyridazine-4-carboxamide was obtained in the form of a yellow solid melting at 262° C.

¹H NMR spectrum (300 MHz, (CD₃)₂SO d6, δ in ppm): 4.62 (d, J=6 Hz: 2H); 7.38 (broad dd, J=8 and 5 Hz: 1H); 7.79 (very broad d, J=8 Hz: 1H); 7.91 (broad d, J=6 Hz: 2H); 8.48 (broad d, J=5 Hz: 1H); 8.60 (broad s: 1H); 8.62 (s: 1H); 8.72 (broad d, J=6 Hz: 2H); 9.94 (broad t, J=6 Hz: 1H); 14.15 (unresolved peak: 1H).

[M+1]-peak: 308

EXAMPLE 15

3-oxo-6-pyridin-4-yl-N-(pyridin-2-ylmethyl)-2,3-dihydropyridazine-4-carboxamide

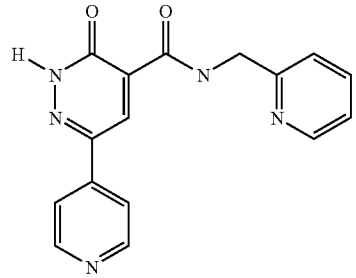

Working as in example 13 for the preparation of ethyl 3-[(3-oxo-6-pyridin-4-yl-2,3-dihydropyridazine-4-carbonyl)amino]propionate, but starting with 0.3 g of 3-oxo-6-pyridin-4-yl-2,3-dihydropyridazine-4-carboxylic acid, 30 cm³ of N,N-dimethylformamide, 0.233 g of 1-hydroxybenzotriazole, 0.18 cm³ of 2-(aminomethyl)pyridine, 0.31 cm³ of N,N-diisopropylethylamine and 0.65 g of O-(7-azabenzotriazol-1-yl)-N,N,N',N'-tetramethyluronium hexafluorophosphate, 0.125 g of 3-oxo-6-pyridin-4-yl-N-(pyridin-2-ylmethyl)-2,3-dihydropyridazine-4-carboxamide was obtained in the form of a white solid melting at 242° C.

¹H NMR spectrum (300 MHz, (CD₃)₂SO d6, δ in ppm): 4.71 (d, J=6 Hz: 2H); 7.33 (broad dd, J=8 and 5.5 Hz: 1H); 7.42 (broad d, J=8 Hz: 1H); 7.81 (resolved t, J=8 and 2 Hz: 1H); 7.93 (broad d, J=6 Hz: 2H); 8.57 (broad d, J=5.5 Hz: 1H); 8.63 (s: 1H); 8.73 (broad d, J=6 Hz: 2H); 10.24 (broad t, J=6 Hz: 1H); from 14.00 to 14.50 (very broad unresolved peak: 1H).

[M+1]-peak: 308

EXAMPLE 16

N-(3,4-dichlorobenzyl)-3-oxo-6-pyridin-4-yl-2,3-dihydropyridazine-4-carboxamide

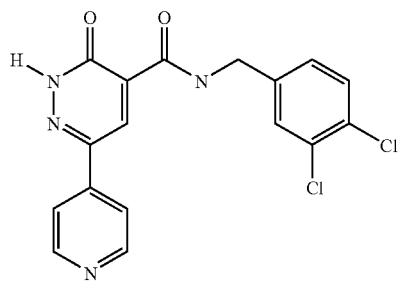

Working as in example 13 for the preparation of ethyl 3-[(3-oxo-6-pyridin-4-yl-2,3-dihydropyridazine-4-carbonyl)amino]propionate, but starting with 0.3 g of 3-oxo-6-pyridin-4-yl-2,3-dihydropyridazine-4-carboxylic acid, 30 cm³ of N,N-dimethylformamide, 0.233 g of 1-hydroxybenzotriazole, 0.19 cm³ of 3,4-dichlorobenzylamine, 0.31 cm³ of N,N-diisopropylethylamine and 0.65 g of O-(7-azabenzotriazol-1-yl)-N,N,N',N'-tetramethyluronium hexafluorophosphate, 0.28 g of N-(3,4-dichlorobenzyl)-3-oxo-6-pyridin-4-yl-2,3-dihydropyridazine-4-carboxamide was obtained in the form of a cream-colored solid melting at 265° C.

¹H NMR spectrum (300 MHz, (CD₃)₂SO d6, δ in ppm): 4.58 (d, J=6 Hz: 2H); 7.37 (dd, J=8 and 1.5 Hz: 1H); 7.62 (d, J=8 Hz: 1H); 7.64 (mt: 1H); 7.91 (broad d, J=6 Hz: 2H); 8.62 (s: 1H); 8.72 (broad d, J=6 Hz: 2H); 9.92 (broad t, J=6 Hz: 1H); from 14.00 to 14.40 (very broad unresolved peak: 1H).

[M+1]-peak: 375

EXAMPLE 17

N-(4-morpholin-4-ylbenzyl)-3-oxo-6-pyridin-4-yl-2,3-dihydropyridazine-4-carboxamide

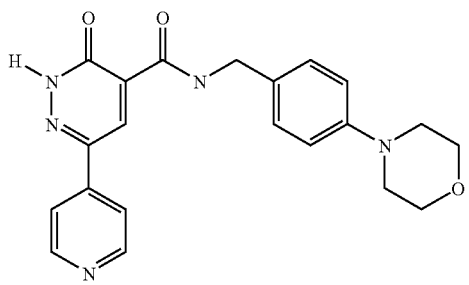

Working as in example 13 for the preparation of ethyl 3-[(3-oxo-6-pyridin-4-yl-2,3-dihydropyridazine-4-carbonyl)amino]propionate, but starting with 0.3 g of 3-oxo-6-pyridin-4-yl-2,3-dihydropyridazine-4-carboxylic acid, 30 cm³ of N,N-dimethylformamide, 0.233 g of 1-hydroxybenzotriazole, 0.265 g of 4-morpholinobenzylamine, 0.31 cm³ of N,N-diisopropylethylamine and 0.65 g of O-(7-azabenzotriazol-1-yl)-N,N,N',N'-tetramethyluronium hexafluorophosphate, and after purification by chromatography on silica gel (particle size 40-63 µm, under an argon pressure of 150 kPa), eluting with dichloromethane, 0.13 g of N-(4-morpholin-4-ylbenzyl)-3-oxo-6-pyridin-4-yl-2,3-dihydropyridazine-4-carboxamide was obtained in the form of a yellow solid melting at 252° C.

¹H NMR spectrum (300 MHz, (CD₃)₂SO d6, δ in ppm) 3.09 (t, J=5 Hz: 4H); 3.74 (t, J=5 Hz: 4H); 4.48 (d., J=6 Hz: 2H); 6.93 (d, J=8 Hz: 2H); 7.24 (d,J=8 Hz: 2H); 7.91 (broad d, J=6 Hz: 2H); 8.62 (s: 1H); 8.72 (broad d, J=6 Hz: 2H); 9.85 (very broad t, J=6 Hz: 1H); 14.22 (unresolved peak: 1H).

[M+1]-peak: 392,16

EXAMPLE 18

(Trimethylsilyl)-2-ethoxymethoxy-4-benzonitrile

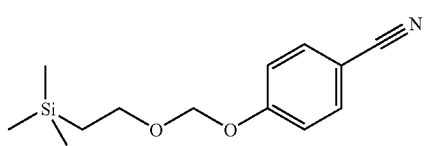

0.085 g of 4-dimethylaminopyridine and 4.9 cm³ of chloromethylethoxy(trimethylsilyl) were added successively to 3 g of 4-hydroxybenzonitrile dissolved in 60 cm³ of dichloromethane, followed by addition of 5.62 cm³ of triethylamine. The reaction medium was stirred for 12 hours at 19° C. and then washed with three times 10 cm³ of aqueous normal hydrochloric acid solution, then with 10 cm³ of water, then with 10 cm³ of normal sodium hydroxide and finally with 10 cm³ of saturated sodium chloride solution. The organic phase was dried over magnesium sulfate, filtered through a sinter funnel and then evaporated under reduced pressure (2 kPa; 45° C.). After purification by chromatography on silica gel (particle size 40-63 µm, under an argon pressure of 150 kPa), eluting with dichloromethane, 3.5 g of (trimethylsilyl)-2-ethoxymethoxy-4-benzonitrile were obtained in the form of a colorless oil.

Mass spectrum: El, m/z=206 (M–SiCH₃)⁺, m/z=191 (M–Si(CH₃)₂)⁺, m/z=176 (M–Si(CH₃)₃)+base peak, m/z=103 (PhCN)⁺, m/z=73 (Si(CH₃)₃)⁺.

¹H NMR spectrum (300 MHz, (CD₃)₂SO d6, δ in ppm): –0.03 (s: 9H); 0.89 (t, J=8 Hz: 2H); 3.72 (t, J=8 Hz: 2H); 5.35 (s: 2H); 7.18 (d, J=9 Hz: 2H); 7.79 (d, J=9 Hz: 2H).

(Trimethylsilyl)-2-ethoxymethoxy-4-benzylamine

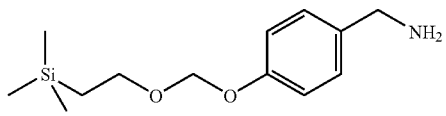

15.5 cm³ of molar lithium aluminum hydride solution were added, at a temperature in the region of 19° C., to 3.5 g of (trimethylsilyl)-2-ethoxymethoxy-4-benzonitrile dissolved in 70 cm³ of tetrahydrofuran. The reaction medium was heated and maintained at the reflux point of the tetrahydrofuran for 4 hours. After cooling to a temperature in the region of 19° C., 0.6 cm³ of water was added to the reaction medium, followed by 0.6 cm³ of aqueous 0.5 N sodium hydroxide solution and 1.8 cm³ of water. The suspension obtained was filtered through a sinter funnel and the residue was washed with 5 times 1.8 cm³ of tetrahydrofuran. The organic phase was dried over magnesium sulfate, filtered through a sinter funnel and then evaporated under reduced pressure (2 kPa; 45° C.). 3.3 g of (trimethylsilyl)-2-ethoxymethoxy-4-benzylamine were obtained in the form of a yellow oil.

Mass spectrum: El, m/z=253 M+, m/z=194 (M–CH₃CH₂OCH₂)+base peak, m/z=180 (M–Si(CH₃)₃+, m/z=73 (Si(CH₃)₃)⁺.

¹H NMR spectrum (400 MHz, (CD₃)₂SO d6, δ in ppm): 0.00 (s: 9H); 0.90 (t, J=8 Hz: 2H); 3.66 (s: 2H); 3.71 (t, J=8 Hz: 2H); 5.20 (s: 2H); 6.95 (broad d, J=8.5 Hz: 2H); 7.24 (broad d, J=8.5 Hz: 2H).

N-(4-hydroxybenzyl)-3-oxo-6-pyridin-4-yl-2,3-dihydropyridazine-4-carboxamide

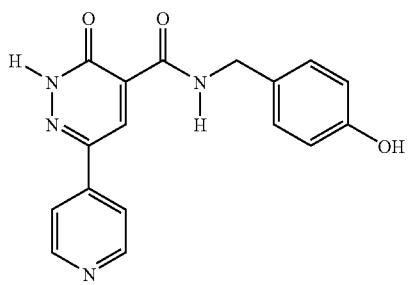

Working as in example 13 for the preparation of ethyl 3-[(3-oxo-6-pyridin-4-yl-2,3-dihydropyridazine-4-carbonyl)amino]propionate, but starting with 0.6 g of 3-oxo-6-pyridin-4-yl-2,3-dihydropyridazine-4-carboxylic acid, 60 cm³ of N,N-dimethylformamide, 0.466 g of 1-hydroxybenzotriazole, 0.91 g of (trimethylsilyl)-2-ethoxymethoxy-4-benzylamine, 0.6 cm³ of N,N-diisopropylethylamine and 1.31 g of O-(7-azabenzotriazol-1-yl)-N,N,N',N'-tetramethyluronium hexafluorophosphate, and after purification by high performance liquid chromatography on a 100×30 mm HyPURITY® 5 µm column, eluting with a mixture increasing from 25% to 95% of acetonitrile/water (containing 0.05% trifluoroacetic acid), 0.16 g of N-(4-hydroxybenzyl)-3-oxo-6-pyridin-4-yl-2,3-dihydropyridazine-4-carboxamide was obtained in the form of a cream-colored solid melting at a temperature above 260° C.

¹H NMR spectrum (300 MHz, (CD₃)₂SO d6, δ in ppm): 4.48 (d, J=6 Hz: 2H); 6.75 (d, J=8 Hz: 2H); 7.19 (d, J=8 Hz: 2H); 8.05 (broad d, J=6 Hz: 2H); 8.69 (s: 1H); 8.79 (broad d, J=6 Hz: 2H); from 9.00 to 9.60 (broad unresolved peak: 1H); 9.74 (t, J=6 Hz: 1H); 14.28 (broad s: 1H).

[M+1]-peak: 323.11

EXAMPLE 19

4-benzyloxyacetophenone

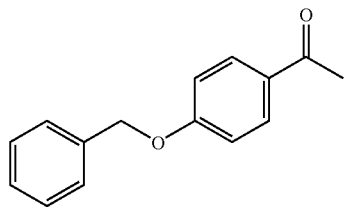

14.5 cm³ of benzyl bromide and 16.75 g of potassium carbonate were added, at a temperature in the region of 19° C., to 15 g of 4-hydroxyacetophenone dissolved in 180 cm³ of acetone. The reaction medium was heated and maintained at the reflux temperature of the acetone for 4 hours. After cooling to a temperature in the region of 19° C., the reaction medium was suction-filtered through a sinter funnel and the insoluble material was rinsed again with 10 cm³ of acetone. The organic phase was evaporated under reduced pressure (2 kPa; 45° C.) and the solid obtained was dissolved in 300 cm³ of ethyl acetate. The organic solution was washed with twice 100 cm³ of water and then with 100 cm³ of saturated sodium chloride solution. The organic phase was dried over magnesium sulfate, filtered through a sinter funnel and then evaporated under reduced pressure (2 kPa; 45° C.). The solid residue was triturated in 20 cm³ of pentane, suction-filtered through a sinter funnel and oven-dried under reduced pressure (10 kPa; 20° C.). 23.1 g of 4-benzyloxyacetophenone were obtained in the form of a white solid melting at 99° C.

¹H NMR spectrum (300 MHz, (CD₃)₂SO d6, δ in ppm): 2.52 (s: 3H); 5.21 (s: 2H); 7.13 (d, J=9 Hz: 2H); from 7.30 to 7.55 (mt: 5H); 7.95 (d, J=9 Hz: 2H).

Diethyl hydroxy[2-(4-benzyloxyphenyl)-2-oxoethyl]malonate

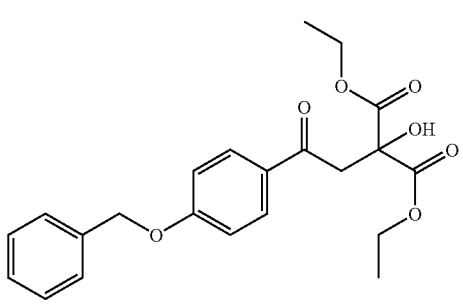

19 cm³ of ethyl ketomalonate and 2.5 cm³ of pyridine were added to 23.1 g of 4-benzyloxyacetophenone. The reaction medium was heated and maintained at reflux for 12 hours. After cooling, the reaction medium was purified by chromatography on silica gel (particle size 40-63 µm, under an argon pressure of 150 kPa), eluting with a mixture of dichloromethane and methanol (99/1 by volume). The fractions containing the product were combined and then concentrated under reduced pressure (45° C.; 5 kPa). The product obtained was triturated in 150 cm³ of ethanol, filtered through a sinter funnel, washed with twice 50 cm³ of ethanol and 50 cm³ of isopropyl ether to give, after drying under reduced pressure (2 kPa; 55° C.), 5.6 g of diethyl hydroxy[2-(4-benzyloxyphenyl)-2-oxoethyl]malonate melting at 80° C.

¹H NMR spectrum (300 MHz, (CD₃)₂SO d6, δ in ppm): 1.21 (t, J=7 Hz: 6H); 3.65 (s: 2H); 4.18 (q, J=7 Hz: 4H); 5.22 (s: 2H); 6.25 (s: 1H); 7.14 (d, J=9 Hz: 2H); from 7.30 to 7.55 (mt: 5H); 7.94 (d, J=9 Hz: 2H).

Ethyl 6-[4-(benzyloxy)phenyl]-3-oxo-2,3-dihydropyridazine-4-carboxylate

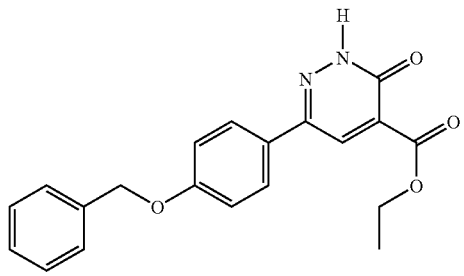

1.69 g of hydrazine dihydrochloride were added, at a temperature in the region of 19° C., to 5.6 g of diethyl hydroxy[2-(4-benzyloxyphenyl)-2-oxoethyl]malonate dissolved in 180 cm³ of ethanol. The reaction medium was heated and maintained at reflux for 12 hours. After cooling, the solvent was removed under reduced pressure (2 kPa; 55° C.). The solid residue was triturated in 20 cm³ of ethanol, suction-filtered through a sinter funnel and oven-dried under reduced pressure (10 kPa; 50° C.). 3.85 g of ethyl 6-[4-(benzyloxy)phenyl]-3-oxo-2,3-dihydropyridazine-4-carboxylate were obtained in the form of a green solid melting at 239° C.

¹H NMR spectrum (300 MHz, (CD₃)₂SO d6, δ in ppm): 1.32 (t, J=7 Hz: 3H); 4.32 (q, J=7 Hz: 2H); 5.19 (s: 2H); 7.14 (d, J=9 Hz: 2H); from 7.30 to 7.55 (mt: 5H); 7.84 (d, J=9 Hz: 2H); 8.30 (s: 1H); 13.51 (broad s: 1H).

6-[4-(benzyloxy)phenyl]-3-oxo-2,3,4,5-tetrahydropyridazine-4-carboxylic acid

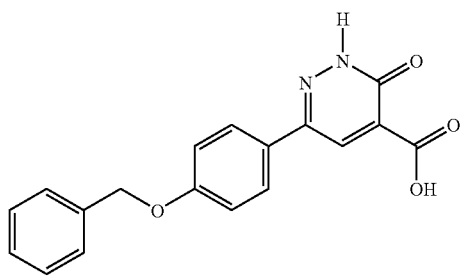

33 cm³ of one molar sodium hydroxide solution were added to 3.85 g of ethyl 6-[4-(benzyloxy)phenyl]-3-oxo-2,3-dihydropyridazine-4-carboxylate. The reaction medium was heated and maintained at reflux for 30 minutes. After cooling, 33 cm³ of one molar hydrochloric acid solution were added.

The suspension obtained was filtered through a sinter funnel and the residue was washed with twice 25 cm³ of water and oven-dried under reduced pressure (10 kPa; 50° C.). 3.05 g of 6-[4-(benzyloxy)phenyl]-3-oxo-2,3,4,5-tetrahydropyridazine-4-carboxylic acid were obtained in the form of a yellow solid melting above 260° C.

$^1$H NMR spectrum (300 MHz, (CD$_3$)$_2$SO d6, δ in ppm): 5.20 (s: 2H); 7.15 (d, J=9 Hz: 2H); from 7.30 to 7.55 (mt: 5H); 7.92 (d, J=9 Hz: 2H); 8.42 (s: 1H).

N-(2,4-dichlorobenzyl)-3-oxo-6-[4-(benzyloxy)phenyl]-2,3-dihydropyridazine-4-carboxamide

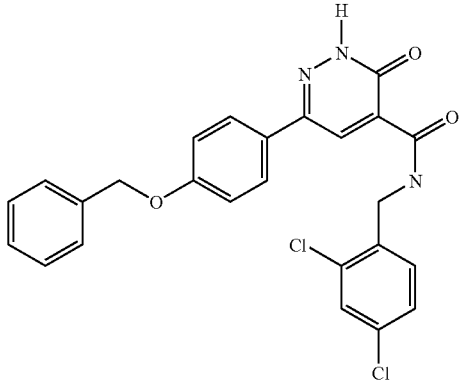

Working as in example 13 for the preparation of ethyl 3-[(3-oxo-6-pyridin-4-yl-2,3-dihydropyridazine-4-carbonyl)amino]propionate, but starting with 1 g of 6-[4-(benzyloxy)phenyl]-3-oxo-2,3,4,5-tetrahydropyridazine-4-carboxylic acid, 100 cm$^3$ of N,N-dimethylformamide, 0.523 g of 1-hydroxybenzotriazole, 0.56 cm$^3$ of 2,4-dichlorobenzylamine, 1.1 cm$^3$ of N,N-diisopropylethylamine and 1.47 g of O-(7-azabenzotriazol-1-yl)-N,N,N',N'-tetramethyluronium hexafluorophosphate, 1.02 g of N-(2,4-dichlorobenzyl)-3-oxo-6-[4-(benzyloxy)phenyl]-2,3-dihydropyridazine-4-carboxamide were obtained in the form of a yellow solid melting at 225° C.

$^1$H NMR spectrum (300 MHz, (CD$_3$)$_2$SO d6, δ in ppm): 4.53 (d, J=6 Hz: 2H); 5.19 (s: 2H); 7.15 (d, J=9 Hz: 2H); from 7.30 to 7.55 (mt: 7H); 7.66 (broad s: 1H); 7.86 (d, J=9 Hz: 2H); 8.47 (s: 1H); 10.24 (unresolved peak: 1H); from 13.75 to 13.95 (broad unresolved peak: 1H).

N-benzyl-3-oxo-6-[4-(hydroxy)phenyl]-2,3-dihydropyridazine-4-carboxamide

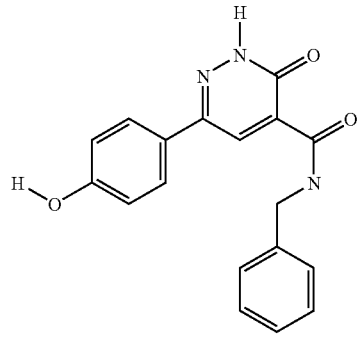

0.525 g of ammonium formate and 0.022 g of palladium hydroxide were added to 0.4 g of N-(2,4-dichlorobenzyl)-3-oxo-6-[4-(benzyloxy)phenyl]-2,3-dihydropyridazine-4-carboxamide dissolved in 10 cm$^3$ of methanol. The reaction medium was heated and maintained at reflux for 2 hours. After cooling, the reaction medium was suction-filtered through a sinter funnel and the insoluble material was rinsed again with three times 10 cm$^3$ of hot methanol. The organic phase was evaporated under reduced pressure (2 kPa; 45° C.). The residue was recrystallized from methanol. After filtration through a sinter funnel, washing with twice 10 cm$^3$ of methanol and oven-drying under reduced pressure (10 kPa; 50° C.), 0.022 g of N-benzyl-3-oxo-6-[4-(hydroxy)phenyl]-2,3-dihydropyridazine-4-carboxamide was obtained in the form of a yellow solid melting at a temperature above 260° C.

$^1$H NMR spectrum (300 MHz, (CD$_3$)$_2$SO d6, δ in ppm): 4.53 (d, J=6 Hz: 2H); 6.89 (broad d, J=9 Hz: 2H); from 7.20 to 7.45 (mt: 5H); 7.75 (broad d, J=9 Hz: 2H); 8.50 (s: 1H); 10.02 (t, J=6 Hz: 1H).

[M+1]-peak: 322

N-(2,4-dichlorobenzyl)-3-oxo-6-[4-(hydroxy)phenyl]-2,3-dihydropyridazine-4-carboxamide and N-(2,4-dichlorobenzyl)-3-oxo-6-[3-benzyl-4-hydroxyphenyl]-2,3-dihydropyridazine-4-carboxamide

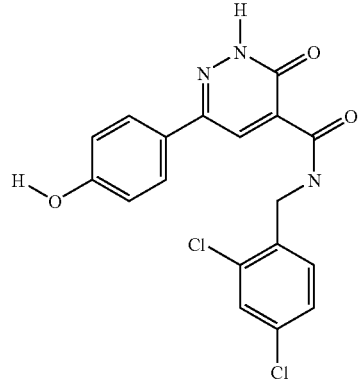

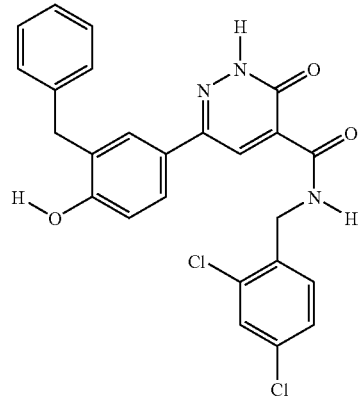

5 cm$^3$ of trifluoroacetic acid were added to 0.4 g of N-(2,4-dichlorobenzyl)-3-oxo-6-[4-(benzyloxy)phenyl]-2,3-dihydropyridazine-4-carboxamide. The reaction medium was heated and maintained at reflux for 2 hours. After cooling, the solvent was removed under reduced pressure (2 kPa; 55° C.). The residue was purified by high performance liquid chromatography on a 100×30 mm HyPURITY® 5 μm column, eluting with a mixture increasing from 5% to 95% of acetonitrile/water (containing 0.05% trifluoroacetic acid).

0.021 g of N-(2,4-dichlorobenzyl)-3-oxo-6-[4-(hydroxy)phenyl]-2,3-dihydropyridazine-4-carboxamide was obtained in the form of a yellow solid melting at a temperature above 260° C.

$^1$H NMR spectrum (300 MHz, (CD$_3$)$_2$SO d6, δ in ppm): 4.63 (d, J=6 Hz: 2H); 6.88 (d, J=8 Hz: 2H); 7.45 (s: 2H); 7.65 (s: 1H); 7.75 (d, J=8 Hz: 2H); 8.47 (s: 1H); 9.90 (unresolved peak: 1H); 10.11 (broad t, J=6 Hz: 1H); 13.78 (broad unresolved peak: 1H).

0.040 g of N-(2,4-dichlorobenzyl)-3-oxo-6-[3-benzyl-4-hydroxyphenyl]-2,3-dihydropyridazine-4-carboxamide was also obtained, in the form of a yellow solid melting at a temperature in the region of 270° C.

$^1$H NMR spectrum (300 MHz, (CD$_3$)$_2$SO d6, δ in ppm): 3.95 (s: 2H); 4.62 (d, J=6 Hz: 2H); 6.94 (d, J=8.5 Hz: 1H); from 7.10 to 7.35 (mt: 5H); 7.44 (mt: 2H); 7.60 (dd, J=8.5 and 2 Hz: 1H); 7.65 (mt: 2H); 8.45 (s: 1H); 9.95 (broad s: 1H); 10.07 (broad t, J=6 Hz: 1H); 13.81 (unresolved peak: 1H).

EXAMPLE 20

Diethyl hydroxy(pyridin-2-oxoethyl)malonate

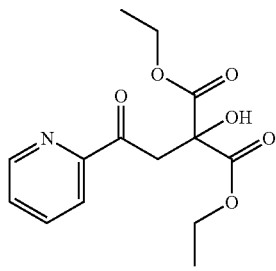

Working as in example 19 for the preparation of diethyl hydroxy[2-(4-benzyloxyphenyl)-2-oxoethyl]malonate, but starting with 13 cm$^3$ of 2-acetylpyridine, 21 cm$^3$ of ethyl ketomalonate and 2.5 cm$^3$ of pyridine, and after purification by chromatography on silica gel (particle size 40-63 μm, under an argon pressure of 150 kPa), eluting with dichloromethane, 31.1 g of diethyl hydroxy(pyridin-2-oxoethyl)malonate were obtained in the form of a brown oil.

$^1$H NMR spectrum (300 MHz, (CD$_3$)$_2$SO d6, δ in ppm): 1.20 (t, J=7 Hz: 6H); 3.90 (s: 2H); 4.19 (q, J=7 Hz: 4H); 6.38 (s: 1H); 7.71 (ddd, J 7.5-5 and 1.5 Hz: 1H); 7.97 (broad d, J=7.5 Hz: 1H); 8.04 (resolved t, J=7.5 and 1.5 Hz: 1H); 8.76 (broad d, J=5 Hz: 1H).

Ethyl 6-pyridin-2-yl-3-oxo-2,3-dihydropyridazine-4-carboxylate

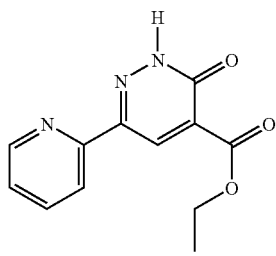

Working as in example 19 for the preparation of ethyl 6-[4-(benzyloxy)phenyl]-3-oxo-2,3-dihydropyridazine-4-carboxylate, but starting with 31.1 g of diethyl hydroxy (pyridin-2-oxoethyl)malonate, 11.55 g of hydrazine dihydrochloride and 700 cm$^3$ of ethanol, and after purification by chromatography on silica gel (particle size 40-63 μm, under an argon pressure of 150 kPa), eluting with dichloromethane, followed by recrystallization from ethanol, 6.9 g of ethyl 6-pyridin-2-yl-3-oxo-2,3-dihydropyridazine-4-carboxylate were obtained in the form of a yellow solid melting at 182° C.

$^1$H NMR spectrum (300 MHz, (CD$_3$)$_2$SO d6, δ in ppm): 1.33 (t, J=7 Hz: 3H); 4.33 (q, J=7 Hz: 2H); 7.50 (ddd, J=8-5 and 1.5 Hz: 1H); 7.97 (resolved t, J=8 and 2 Hz: 1H); 8.08 (broad d, J=8 Hz: 1H); 8.67 (s: 1H); 8.70 (ddd, J=5-2 and 1.5 Hz: 1H); 13.72 (broad s: 1H).

6-pyridin-2-yl-3-oxo-2,3,4,5-tetrahydropyridazine-4-carboxylic acid

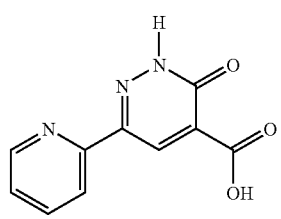

Working as in example 19 for the preparation of 6-[4-(benzyloxy)phenyl]-3-oxo-2,3,4,5-tetrahydropyridazine-4-carboxylic acid, but starting with 4 g of ethyl 6-pyridin-2-yl-3-oxo-2,3-dihydropyridazine-4-carboxylate, 49 cm$^3$ of one molar sodium hydroxide solution and 50 cm$^3$ of one molar hydrochloric acid solution, 3.44 g of 6-pyridin-2-yl-3-oxo-2,3,4,5-tetrahydropyridazine-4-carboxylic acid were obtained in the form of a beige-colored solid melting at a temperature above 260° C.

$^1$H NMR spectrum (300 MHz, (CD$_3$)$_2$SO d6, δ in ppm): 7.53 (broad dd, J=7.5 and 5 Hz: 1H); 7.99 (resolved t, J=7.5 and 1.5 Hz: 1H); 8.13 (broad d, J=7.5 Hz: 1H); 8.72 (broad d, J=5 Hz: 1H); 8.83 (s: 1H); from 13.55 to 14.30 (unresolved peak: 2H).

N-(2,4-dichlorobenzyl)-3-oxo-6-pyridin-2-yl-2,3-dihydropyridazine-4-carboxamide

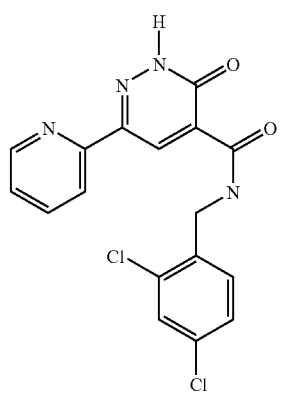

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-2-yl-2,3-dihydropyridazine-4-carboxylic acid, 10 cm$^3$ of dichloromethane, 1 cm$^3$ of dimethylformamide, 0.12 cm$^3$ of oxalyl chloride, 0.21 cm$^3$ of 2,4-dichlorobenzylamine and 0.22 cm³ of triethylamine, 0.22 g of N-(2,4-dichlorobenzyl)-3-oxo-6-pyridin-2-yl-2,3-dihydropyridazine-4-carboxamide was obtained in the form of a cream-colored solid melting at a temperature above 260° C.

¹H NMR spectrum (300 MHz, (CD₃)₂SO d6, δ in ppm): 4.65 (d, J=6 Hz: 2H); 7.46 (s: 2H); 7.55 (broad dd, J=8 and 5 Hz: 1H); 7.67 (broad s: 1H); 8.31 (ddd, J=8-2.5 and 2 Hz: 1H); 8.59 (s: 1H); 8.68 (dd, J=S and 2 Hz: 1H); 9.10 (board d, J=2.5 Hz: 1H); 10.09 (t, J=6 Hz: 1H).

[M+1]-peak: 375

EXAMPLE 21

Diethyl hydroxy(pyridin-3-oxoethyl)malonate

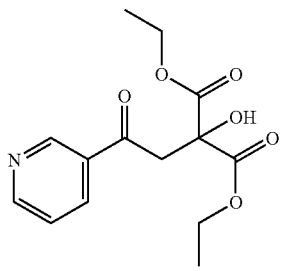

Working as in example 19 for the preparation of diethyl hydroxy[2-(4-benzyloxyphenyl)-2-oxoethyl]malonate, but starting with 8 cm³ of 3-acetylpyridine, 14 cm³ of ethyl ketomalonate and 2 cm³ of pyridine, and after purification by chromatography on silica gel (particle size 40-63 μm, under an argon pressure of 150 kPa), eluting with dichloromethane, 8.85 g of diethyl hydroxy(pyridin-3-oxoethyl)malonate were obtained in the form of a brown oil.

¹H NMR spectrum (300 MHz, (CD₃)₂SO d6, δ in ppm): 1.21 (t, J=7 Hz: 6H); 3.76 (s: 2H); 4.20 (q, J=7 Hz: 4H); 6.44 (s: 1H); 7.59 (broad dd, J=8 and 5 Hz: 1H); 8.31 (ddd, J=8-2.5 and 2 Hz: 1H); 8.83 (dd, J=S and 2 Hz: 1H); 9.12 (broad d, J=2.5 Hz: 1H).

Ethyl 6-pyridin-3-yl-3-oxo-2,3-dihydropyridazine-4-carboxylate

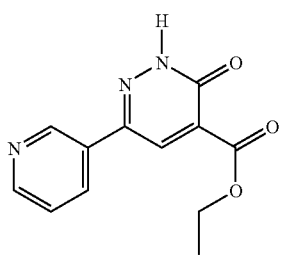

Working as in example 19 for the preparation of ethyl 6-[4-(benzyloxy)phenyl]-3-oxo-2,3-dihydropyridazine-4-carboxylate, but starting with 8.85 g of diethyl hydroxy(pyridin-3-oxoethyl)malonate, 3.67 g of hydrazine dihydrochloride and 250 cm³ of ethanol, and after recrystallization from ethanol, 3.6 g of ethyl 6-pyridin-3-yl-3-oxo-2,3-dihydropyridazine-4-carboxylate were obtained in the form of a green solid melting at a temperature in the region of 150° C.

¹H NMR spectrum (300 MHz, (CD₃)₂SO d6, δ in ppm): 1.33 (t, J=7 Hz: 3H); 4.34 (q, J=7 Hz: 2H); 7.54 (broad dd, J=8 and 5 Hz: 1H); 8.28 (ddd, J=8-2.5 and 2 Hz: 1H); 8.41 (s: 1H); 8.67 (dd, J=5 and 2 Hz: 1H); 9.09 (broad d, J=2.5 Hz: 1H); 13.75 (unresolved peak: 1H).

6-pyridin-3-yl-3-oxo-2,3,4,5-tetrahydropyridazine-4-carboxylic acid

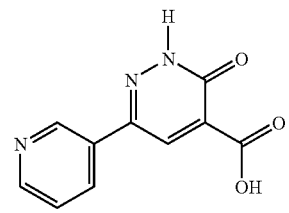

Working as in example 19 for the preparation of 6-[4-(benzyloxy)phenyl]-3-oxo-2,3,4,5-tetrahydropyridazine-4-carboxylic acid, but starting with 2 g of ethyl 6-pyridin-3-yl-3-oxo-2,3-dihydropyridazine-4-carboxylate, 24.5 cm³ of one molar sodium hydroxide solution and 25 cm³ of one molar hydrochloric acid solution, 1.65 g of 6-pyridin-3-yl-3-oxo-2,3,4,5-tetrahydropyridazine-4-carboxylic acid were obtained in the form of a cream-colored solid melting at a temperature above 260° C.

¹H NMR spectrum (300 MHz, (CD₃)₂SO d6, δ in ppm): 7.55 (broad dd, J=8 and 5 Hz: 1H); 8.33 (ddd, J=8-2.5 and 2 Hz: 1H); 8.56 (s: 1H); 8.68 (dd, J=5 and 2 Hz: 1H); 9.12 (broad d, J=2.5 Hz: 1H); from 13.50 to 14.80 (very broad unresolved peak: 2H).

N-(2,4-dichlorobenzyl)-3-oxo-6-pyridin-3-yl-2,3-dihydropyridazine-4-carboxamide

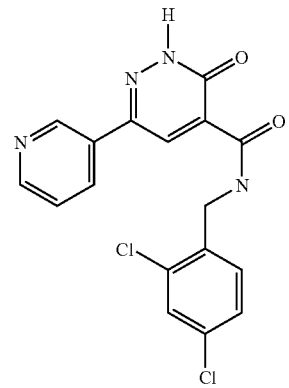

Working as in example 2 for the preparation of N-(2,4-dichlorobenzyl)-3-oxo-6-pyridin-4-yl-2,3-dihydropyridazine-4-carboxamide, but starting with 0.3 g of 3-oxo-6-pyridin-3-yl-2,3-dihydropyridazine-4-carboxylic acid, 10 cm³ of dichloromethane, 1 cm³ of dimethylformamide, 0.12 cm³ of oxalyl chloride, 0.21 cm³ of 2,4-dichlorobenzylamine and 0.22 cm³ of triethylamine, and after purification by chromatography on silica gel (particle size 40-63 μm, under an argon pressure of 150 kPa), eluting with a mixture of dichloromethane and methanol (90/10 by volume), 0.204 g of N-(2,4-dichlorobenzyl)-3-oxo-6-pyridin-3-yl-2,3-dihydropyridazine-4-carboxamide was obtained in the form of a cream-colored solid melting at a temperature in the region of 260° C.

¹H NMR spectrum (300 MHz, (CD₃)₂SO d6, δ in ppm): 4.65 (d, J=6 Hz: 2H); 7.46 (s: 2H); 7.55 (broad dd, J=8 and 5 Hz: 1H); 7.67 (broad s: 1H); 8.31 (ddd, J=8-2.5 and 2 Hz: 1H); 8.59 (s: 1H); 8.68 (dd, J=Sand 2 Hz: 1H); 9.10 (broad d, J=2.5 Hz: 1H); 10.09 (t, J=6 Hz: 1H).

[M+1]-peak: 375

If not stated otherwise, the examples listed in the following table are synthesized according to the above-mentioned methods.

| Example | structural formula | name | M + 1 peak | synthesis according to example |
|---|---|---|---|---|
| 22 | | N-(2,4-Dichlorbenzyl)-3-oxo-6-[4-(hydroxy)phenyl]-2,3-dihydropyridazine-4-carboxylic acid | 390 | 13 |
| 23 | CHIRAL | R-3-Oxo-6-pyridin-4-yl-2,3-dihydro-pyridazine-4-carboxylic acid [1-(4-chloro-phenyl)-ethyl]-amide | 355.09 | 13 |
| 24 | | 3-Oxo-6-pyridin-4-yl-2,3-dihydro-pyridazine-4-carboxylic acid (5-methyl-3-phenyl-isoxazol-4-ylmethyl)-amide | 388.13 | 13 |
| 25 | CHIRAL | S-3-Oxo-6-pyridin-4-yl-2,3-dihydro-pyridazine-4-carboxylic acid [1-(4-chloro-phenyl)-ethyl]-amide | 355.09 | 13 |

-continued

| Example | structural formula | name | M + 1 peak | synthesis according to example |
|---------|-------------------|------|------------|-------------------------------|
| 26 | | 3-Oxo-6-pyridin-4-yl-2,3-dihydro-pyridazine-4-carboxylic acid [1-(2,4-dichloro-phenyl)-ethyl]-amide | 389.05 | 13 |
| 27 | | 3-Oxo-6-pyridin-4-yl-2,3-dihydro-pyridazine-4-carboxylic acid (1-benzyl-piperidin-4-yl)-amide | 390.19 | 13 |
| 28 | | 3-Oxo-6-pyridin-4-yl-2,3-dihydro-pyridazine-4-carboxylic acid (4-hydroxy-cyclohexyl)-amide | 315.14 | 13 |
| 29 | | 6-(4-Methoxy-phenyl)-3-oxo-2,3-dihydro-pyridazine-4-carboxylic acid (3-pyridin-3-yl-propyl)-amide | 365.15 | 13 |
| 30 | | 3-Oxo-6-pyridin-4-yl-2,3-dihydro-pyridazine-4-carboxylic acid (2-diisopropylamino-ethyl)-amide | 344.2 | 13 |

-continued

| Example | structural formula | name | M + 1 peak | synthesis according to example |
|---|---|---|---|---|
| 31 | | 3-Oxo-6-pyridin-4-yl-2,3-dihydro-pyridazine-4-carboxylic acid (4-hydroxy-butyl)-amide | 289.12 | 13 |
| 32 | | 4-({[6-(4-Hydroxy-3,5-dimethyl-phenyl)-3-oxo-2,3-dihydro-pyridazine-4-carbonyl]-amino}-methyl)-benzoic acid | 394.13 | 13 |
| 33 | | 3-Oxo-6-pyridin-4-yl-2,3-dihydro-pyridazine-4-carboxylic acid 4-(4-methyl-piperazine-1-carbonyl)-benzylamide; compound with trifluoro-acetic acid | 433.19 | 13 |
| 34 | | 6-(2-Methylamino-pyrimidin-4-yl)-3-oxo-2,3-dihydro-pyridazine-4-carboxylic acid 4-chloro-benzylamide | 371.1 | 13 |

-continued

| Example | structural formula | name | M + 1 peak | synthesis according to example |
|---|---|---|---|---|
| 35 | | 4-[(3-Oxo-6-pyridin-4-yl-2,3-dihydro-pyridazine-4-carbonyl)-amino]-carboxylic acid tert-butyl ester | 400.19 | 13 |
| 36 | | 3-Oxo-6-pyridin-4-yl-2,3-dihydro-pyridazine-4-carboxylic acid cyclohexylamide | 299.14 | 13 |
| 37 | CHIRAL | S,S-3-Oxo-6-pyridin-4-yl-2,3-dihydro-pyridazine-4-carboxylic acid (2-benzyloxy-cyclohexyl)-amide | 405.19 | 13 |
| 38 | CHIRAL | R,R-3-Oxo-6-pyridin-4-yl-2,3-dihydro-pyridazine-4-carboxylic acid (2-benzyloxy-cyclohexyl)-amide | 405.19 | 13 |

-continued

| Example | structural formula | name | M + 1 peak | synthesis according to example |
|---|---|---|---|---|
| 39 | | 3-Oxo-6-(1H-pyrazol-4-yl)-2,3-dihydro-pyridazine-4-carboxylic acid 4-chloro-benzylamide | 330.07 | 41 |
| 40 | | 6-(4-Hydroxy-phenyl)-3-oxo-2,3-dihydro-pyridazine-4-carboxylic acid 4-chloro-benzylamide | 356.07 | 41 |
| 41 | | 6-(4-Hydroxy-3-methoxy-phenyl)-3-oxo-2,3-dihydro-pyridazine-4-carboxylic acid 4-chloro-benzylamide | 386.08 | description of synthesis at the end of this table |
| 42 | | 6-(3-Chloro-pyridin-4-yl)-3-oxo-2,3-dihydro-pyridazine-4-carboxylic acid 4-chloro-benzylamide | 375.03 | 41 |

-continued

| Example | structural formula | name | M + 1 peak | synthesis according to example |
|---------|-------------------|------|------------|-------------------------------|
| 43 | | 6-Chloro-3-oxo-2,3-dihydro-pyridazine-4-carboxylic acid 4-chloro-benzylamide | 298.01 | 13 |
| 44 | | 3-Oxo-6-pyridin-4-yl-2,3-dihydro-pyridazine-4-carboxylic acid tert-butylamide | 273.13 | 13 |
| 45 | | 3-Oxo-6-pyridin-4-yl-2,3-dihydro-pyridazine-4-carboxylic acid (1-methyl-piperidin-4-yl)-amide | 314.15 | 13 |
| 46 | CHIRAL | 3-Oxo-6-pyridin-4-yl-2,3-dihydro-pyridazine-4-carboxylic acid (2-oxo-azepan-3-yl)-amide | 328.13 | 13 |

-continued

| Example | structural formula | name | M + 1 peak | synthesis according to example |
|---|---|---|---|---|
| 47 | | 4-[(3-Oxo-6-pyridin-4-yl-2,3-dihydro-pyridazine-4-carbonyl)-amino]-piperidine-1-carboxylic acid ethyl ester | 372.16 | 13 |
| 48 | | 6-(4-Hydroxy-3,5-dimethyl-phenyl)-3-oxo-2,3-dihydro-pyridazine-4-carboxylic acid (3-pyridin-3-yl-propyl)-amide | 379.17 | 13 |
| 49 | | 6-(4-Hydroxy-3-methoxy-phenyl)-3-oxo-2,3-dihydro-pyridazine-4-carboxylic acid (3-pyridin-3-yl-propyl)-amide | 381.15 | 13 |
| 50 | | 3-Oxo-6-pyridin-4-yl-2,3-dihydro-pyridazine-4-carboxylic acid [2-(3-bromo-4-methoxy-phenyl)-ethyl]-amide; compound with trifluoro-acetic acid | 429.05 | 13 |

-continued

| Example | structural formula | name | M + 1 peak | synthesis according to example |
|---|---|---|---|---|
| 51 | | 6-(4-METHOXY-PHENYL)-3-OXO-2,3-DIHYDRO-PYRIDAZINE-4-CARBOXYLIC ACID 4-CHLORO-BENZYLAMIDE | 370.09 | 41 |
| 52 | | 6-(4-Hydroxy-3,5-dimethyl-phenyl)-3-oxo-2,3-dihydro-pyridazine-4-carboxylic acid 4-chloro-benzylamide | 384.1 | 41 |
| 53 | | 6-(3-Hydroxy-phenyl-3-oxo-2,3-dihydro-pyridazine-4-carboxylic acid 4-chloro-benzylamide | 356.07 | 41 |
| 54 | | 3-Oxo-6-pyridin-4-yl-2,3-dihydro-pyridazine-4-carboxylic acid propylamide; compound with trifluoro-acetic acid | 259.11 | 13 |
| 55 | | 3-Oxo-6-pyridin-4-yl-2,3-dihydro-pyridazine-4-carboxylic acid (2-pyridin-3-yl-ethyl)-amide; compound with trifluoro-acetic acid | 322.12 | 13 |

-continued

| Example | structural formula | name | M + 1 peak | synthesis according to example |
|---|---|---|---|---|
| 56 | | 3-Oxo-6-pyridin-4-yl-2,3-dihydro-pyridazine-4-carboxylic acid (2-pyridin-2-yl-ethyl)-amide; compound with trifluoro-acetic acid | 322.12 | 13 |
| 57 | | 3-Oxo-6-pyridin-4-yl-2,3-dihydro-pyridazine-4-carboxylic acid (2-ethoxy-ethyl)-amide; compound with trifluoro-acetic acid | 289.12 | 13 |
| 58 | | 3-Oxo-6-pyridin-4-yl-2,3-dihydro-pyridazine-4-carboxylic acid (2-methoxy-ethyl)-amide; compound with trifluoro-acetic acid | 275.11 | 13 |
| 59 | | 3-Oxo-6-pyridin-4-yl-2,3-dihydro-pyridazine-4-carboxylic acid (5-methyl-pyrazin-2-ylmethyl)-amide; compound with trifluoro-acetic acid | 323.12 | 13 |
| 60 | | 3-Oxo-6-pyridin-4-yl-2,3-dihydro-pyridazine-4-carboxylic acid cyclopropylmethyl-amide; compound with trifluoro-acetic acid | 271.11 | 13 |

-continued

| Example | structural formula | name | M + 1 peak | synthesis according to example |
|---|---|---|---|---|
| 61 | CHIRAL | 3-Oxo-6-pyridin-4-yl-2,3-dihydro-pyridazine-4-carboxylic acid [(R)-1-(tetrahydro-furan-2-yl)methyl]-amide; compound with trifluoro-acetic acid | 301.12 | 13 |
| 62 | | 3-Oxo-6-pyridin-4-yl-2,3-dihydro-pyridazine-4-carboxylic acid cyclopropylamide; compound with trifluoro-acetic acid | 257.1 | 13 |
| 63 | | 3-Oxo-6-pyridin-4-yl-2,3-dihydro-pyridazine-4-carboxylic acid cyclobutylamide; compound with trifluoro-acetic acid | 271.11 | 13 |
| 64 | | 3-Oxo-6-pyridin-4-yl-2,3-dihydro-pyridazine-4-carboxylic acid (1H-benzoimidazol-2-ylmethyl)-amide; compound with trifluoro-acetic acid | 347.12 | 13 |

-continued

| Example | structural formula | name | M + 1 peak | synthesis according to example |
|---|---|---|---|---|
| 65 | | 3-Oxo-6-pyridin-4-yl-2,3-dihydro-pyridazine-4-carboxylic acid (3-methyl-butyl)-amide; compound with trifluoro-acetic acid | 287.14 | 13 |
| 66 | | 3-Oxo-6-pyridin-4-yl-2,3-dihydro-pyridazine-4-carboxylic acid (3-phenyl-propyl)-amide; compound with trifluoro-acetic acid | 335.14 | 13 |
| 67 | CHIRAL | 3-Oxo-6-pyridin-4-yl-2,3-dihydro-pyridazine-4-carboxylic acid [(R)-1-(4-bromo-phenyl)-ethyl]-amide; compound with trifluoro-acetic acid | 399.04 | 13 |
| 68 | | 3-Oxo-6-pyridin-4-yl-2,3-dihydro-pyridazine-4-carboxylic acid (2-o-tolyl-ethyl)-amide; compound with trifluoro-acetic acid | 335.14 | 13 |
| 69 | | 3-Oxo-6-pyridin-4-yl-2,3-dihydro-pyridazine-4-carboxylic acid [2-(2-methoxy-phenyl)-ethyl]-amide; compound with trifluoro-acetic acid | 351.14 | 13 |

| Example | structural formula | name | M + 1 peak | synthesis according to example |
|---|---|---|---|---|
| 70 | | 3-Oxo-6-pyridin-4-yl-2,3-dihydro-pyridazine-4-carboxylic acid [2-(3-methoxy-phenyl)-ethyl]-amide; compound with trifluoro-acetic acid | 351.14 | 13 |
| 71 | | 3-Oxo-6-pyridin-4-yl-2,3-dihydro-pyridazine-4-carboxylic acid [2-(3-hydroxy-phenyl)-ethyl]-amide; compound with trifluoro-acetic acid | 337.12 | 13 |
| 72 | | 3-Oxo-6-pyridin-4-yl-2,3-dihydro-pyridazine-4-carboxylic acid [2-(4-bromo-phenyl)-ethyl]-amide; compound with trifluoro-acetic acid | 399.04 | 13 |
| 73 | | 3-Oxo-6-pyridin-4-yl-2,3-dihydro-carboxylic acid [2-(4-methoxy-phenyl)-ethyl]-amide; compound with trifluoro-acetic acid | 351.14 | 13 |
| 74 | | 3-Oxo-6-pyridin-4-yl-2,3-dihydro-pyridazine-4-carboxylic acid [2-(4-hydroxy-phenyl)-ethyl]-amide; compound with trifluoro-acetic acid | 337.12 | 13 |

-continued

| Example | structural formula | name | M + 1 peak | synthesis according to example |
|---|---|---|---|---|
| 75 | | 3-Oxo-6-pyridin-4-yl-2,3-dihydro-pyridazine-4-carboxylic acid 4-bromo-benzylamide; compound with trifluoro-acetic acid | 385.02 | 13 |
| 76 | | 3-Oxo-6-pyridin-4-yl-2,3-dihydro-pyridazine-4-carboxylic acid (2-phenoxy-ethyl)-amide; compound with trifluoro-acetic acid | 337.12 | 13 |
| 77 | | 3-Oxo-6-pyridin-4-yl-2,3-dihydro-pyridazine-4-carboxylic acid 2,4-dimethyl-benzylamide; compound with trifluoro-acetic acid | 335.14 | 13 |
| 78 | | 3-Oxo-6-pyridin-4-yl-2,3-dihydro-pyridazine-4-carboxylic acid 2-methyl-benzylamide; compound with trifluoro-acetic acid | 321.13 | 13 |

-continued

| Example | structural formula | name | M + 1 peak | synthesis according to example |
|---------|-------------------|------|------------|-------------------------------|
| 79 | | 3-Oxo-6-pyridin-4-yl-2,3-dihydro-pyridazine-4-carboxylic acid 2-methoxy-benzylamide; compound with trifluoro-acetic acid | 337.12 | 13 |
| 80 | | 3-Oxo-6-pyridin-4-yl-2,3-dihydro-pyridazine-4-carboxylic acid 3,4-dimethyl-benzylamide; compound with trifluoro-acetic acid | 335.14 | 13 |
| 81 | | 3-Oxo-6-pyridin-4-yl-2,3-dihydro-pyridazine-4-carboxylic acid 3,5-dimethyl-benzylamide; compound with trifluoro-acetic acid | 335.14 | 13 |

-continued

| Example | structural formula | name | M + 1 peak | synthesis according to example |
|---|---|---|---|---|
| 82 | 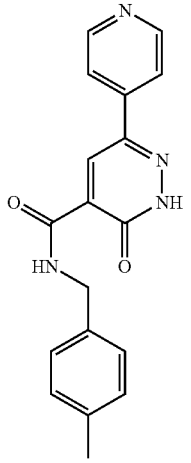 | 3-Oxo-6-pyridin-4-yl-2,3-dihydro-pyridazine-4-carboxylic acid 4-methyl-benzylamide; compound with trifluoro-acetic acid | 321.13 | 13 |
| 83 | 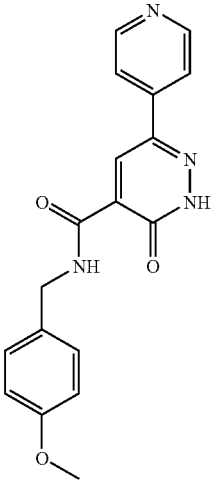 | 3-Oxo-6-pyridin-4-yl-2,3-dihydro-pyridazine-4-carboxylic acid 4-methoxy-benzylamide; compound with trifluoro-acetic acid | 337.12 | 13 |
| 84 | 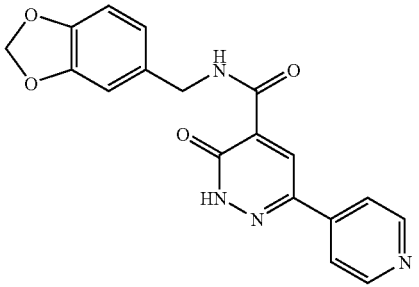 | 3-Oxo-6-pyridin-4-yl-2,3-dihydro-pyridazine-4-carboxylic acid (benzo[1,3]dioxol-5-ylmethyl)-amide; compound with trifluoro-acetic acid | 351.1 | 13 |
| 85 | 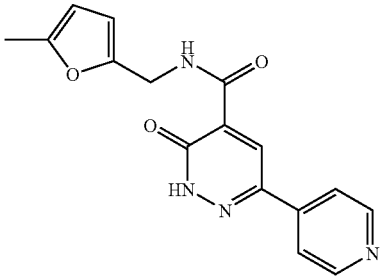 | 3-Oxo-6-pyridin-4-yl-2,3-dihydro-pyridazine-4-carboxylic acid (5-methyl-furan-2-ylmethyl)-amide; compound with trifluoro-acetic acid | 311.11 | 13 |

-continued

| Example | structural formula | name | M + 1 peak | synthesis according to example |
|---------|-------------------|------|------------|-------------------------------|
| 86 | | 3-Oxo-6-pyridin-4-yl-2,3-dihydro-pyridazine-4-carboxylic acid (furan-2-ylmethyl)-amide; compound with trifluoro-acetic acid | 297.09 | 13 |
| 87 | | 3-Oxo-6-pyridin-4-yl-2,3-dihydro-pyridazine-4-carboxylic acid cyclohexylmethyl-amide; compound with trifluoro-acetic acid | 313.16 | 13 |
| 88 | | 3-Oxo-6-pyridin-4-yl-2,3-dihydro-pyridazine-4-carboxylic acid ((1S,2R)-2-phenyl-cyclopropyl)-amide; compound with trifluoro-acetic acid | 333.13 | 13 |
| 89 | | 3-Oxo-6-pyridin-4-yl-2,3-dihydro-pyridazine-4-carboxylic acid (4-methyl-cyclohexyl)-amide; compound with trifluoro-acetic acid | 313.16 | 13 |

-continued

| Example | structural formula | name | M + 1 peak | synthesis according to example |
|---------|-------------------|------|------------|-------------------------------|
| 90 | | 3-Oxo-6-pyridin-4-yl-2,3-dihydro-pyridazine-4-carboxylic acid cyclopentylamide; compound with trifluoro-acetic acid | 285.13 | 13 |
| 91 | | 3-Oxo-6-pyridin-4-yl-2,3-dihydro-pyridazine-4-carboxylic acid indan-2-ylamide; compound with trifluoro-acetic acid | 333.13 | 13 |
| 92 | | 3-Oxo-6-pyridin-4-yl-2,3-dihydro-pyridazine-4-carboxylic acid [2-(5-methyl-1H-indol-3-yl)-ethyl]-amide; compound with trifluoro-acetic acid | 374.15 | 13 |
| 93 | | 3-Oxo-6-pyridin-4-yl-2,3-dihydro-pyridazine-4-carboxylic acid 3-bromo-4-fluoro-benzylamide; compound with trifluoro-acetic acid | 403.01 | 13 |

-continued

| Example | structural formula | name | M + 1 peak | synthesis according to example |
|---------|-------------------|------|------------|-------------------------------|
| 94 | | 3-Oxo-6-pyridin-4-yl-2,3-dihydro-pyridazine-4-carboxylic acid [2-(3,4-dichloro-phenyl)-ethyl]-amide; compound with trifluoro-acetic acid | 389.05 | 13 |
| 95 | | 3-Oxo-6-pyridin-4-yl-2,3-dihydro-pyridazine-4-carboxylic acid [2-(1H-benzoimidazol-2-yl)-ethyl]-amide | 361.13 | 13 |
| 96 | | 3-Oxo-6-pyridin-4-yl-2,3-dihydro-pyridazine-4-carboxylic acid [2-(6-methoxy-1H-indol-3-yl)-ethyl]-amide; compound with trifluoro-acetic acid | 390.15 | 13 |
| 97 | | 3-Oxo-6-pyridin-4-yl-2,3-dihydro-pyridazine-4-carboxylic acid [2-(1H-indol-3-yl)-ethyl]-amide; compound with trifluoro-acetic acid | 360.14 | 13 |

-continued

| Example | structural formula | name | M + 1 peak | synthesis according to example |
|---|---|---|---|---|
| 98 | | 3-Oxo-6-pyridin-4-yl-2,3-dihydro-pyridazine-4-carboxylic acid 4-methanesulfonyl-benzylamide; compound with trifluoro-acetic acid | 385.09 | 13 |
| 99 | | 3-Oxo-6-pyridin-4-yl-2,3-dihydro-pyridazine-4-carboxylic acid (2-methylsulfanyl-ethyl)-amide; compound with trifluoro-acetic acid | 291.08 | 13 |
| 100 | | 3-Oxo-6-pyridin-4-yl-2,3-dihydro-pyridazine-4-carboxylic acid (2-thiophen-2-yl-ethyl)-amide; compound with trifluoro-acetic acid | 327.08 | 13 |
| 101 | | 3-Oxo-6-pyridin-4-yl-2,3-dihydro-pyridazine-4-carboxylic acid [2-(2,4-dichloro-phenyl)-ethyl]-amide; compound with trifluoro-acetic acid | 389.05 | 13 |

| Example | structural formula | name | M + 1 peak | synthesis according to example |
|---|---|---|---|---|
| 102 | 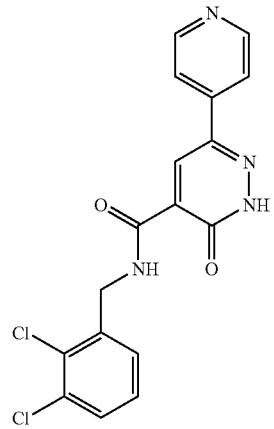 | 3-Oxo-6-pyridin-4-yl-2,3-dihydro-pyridazine-4-carboxylic acid 2,3-dichloro-benzylamide; compound with trifluoro-acetic acid | 375.03 | 13 |
| 103 | 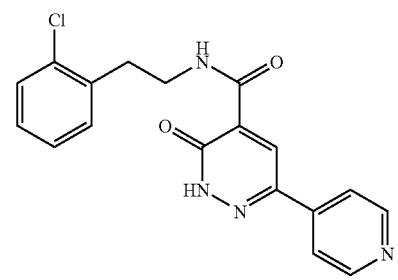 | 3-Oxo-6-pyridin-4-yl-2,3-dihydro-pyridazine-4-carboxylic acid [2-(2-chloro-phenyl)-ethyl]-amide; compound with trifluoro-acetic acid | 355.09 | 13 |
| 104 | 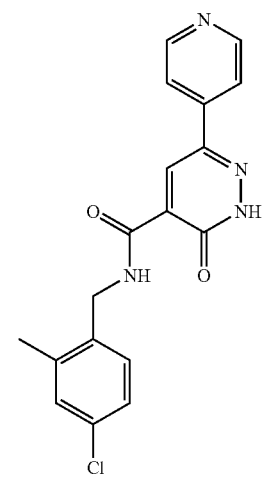 | 3-Oxo-6-pyridin-4-yl-2,3-dihydro-pyridazine-4-carboxylic acid 4-chloro-2-methyl-benzylamide; compound with trifluoro-acetic acid | 355.09 | 13 |
| 105 | 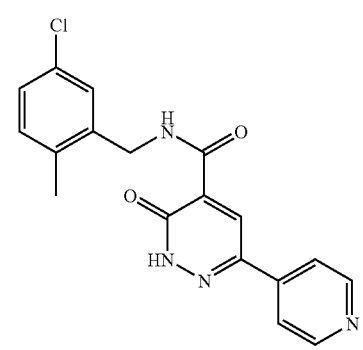 | 3-Oxo-6-pyridin-4-yl-2,3-dihydro-pyridazine-4-carboxylic acid 5-chloro-2-methyl-benzylamide; compound with trifluoro-acetic acid | 355.09 | 13 |

-continued

| Example | structural formula | name | M + 1 peak | synthesis according to example |
|---|---|---|---|---|
| 106 | 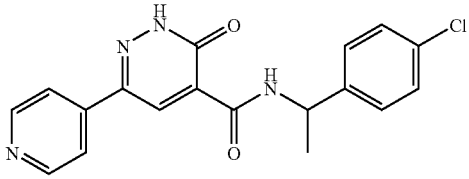 | 3-Oxo-6-pyridin-4-yl-2,3-dihydro-pyridazine-4-carboxylic acid [1-(4-chloro-phenyl)-ethyl]-amide; compound with trifluoro-acetic acid | 355.09 | 13 |
| 107 | 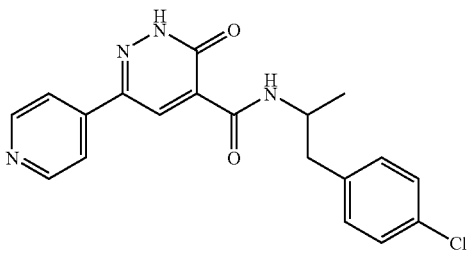 | 3-Oxo-6-pyridin-4-yl-2,3-dihydro-pyridazine-4-carboxylic acid [2-(4-chloro-phenyl)-1-methyl-ethyl]-amide; compound with trifluoro-acetic acid | 369.1 | 13 |
| 108 | 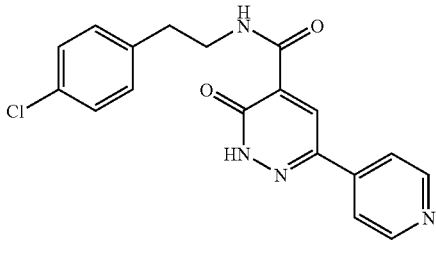 | 3-Oxo-6-pyridin-4-yl-2,3-dihydro-pyridazine-4-carboxylic acid [2-(4-chloro-phenyl)-ethyl]-amide; compound with trifluoro-acetic acid | 355.09 | 13 |
| 109 | 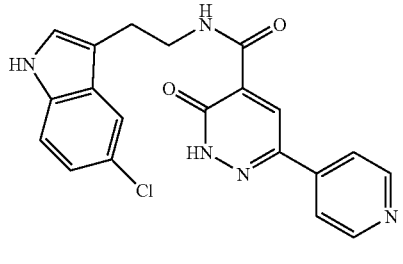 | 3-Oxo-6-pyridin-4-yl-2,3-dihydro-pyridazine-4-carboxylic acid [2-(5-chloro-1H-indol-3-yl)-ethyl]-amide; compound with trifluoro-acetic acid | 394.1 | 13 |
| 110 | 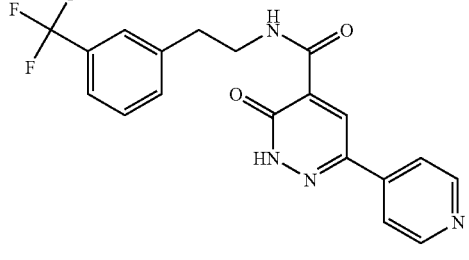 | 3-Oxo-6-pyridin-4-yl-2,3-dihydro-pyridazine-4-carboxylic acid [2-(3-trifluoromethyl-phenyl)-ethyl]-amide; compound with trifluoro-acetic acid | 389.12 | 13 |

-continued

| Example | structural formula | name | M + 1 peak | synthesis according to example |
|---|---|---|---|---|
| 111 | 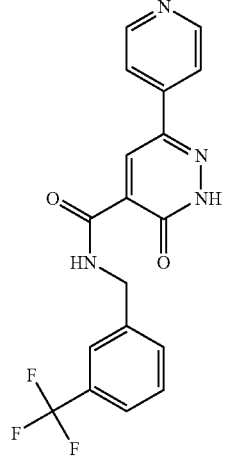 | 3-Oxo-6-pyridin-4-yl-2,3-dihydro-pyridazine-4-carboxylic acid 3-trifluoromethyl-benzylamide; compound with trifluoro-acetic acid | 375.1 | 13 |
| 112 | 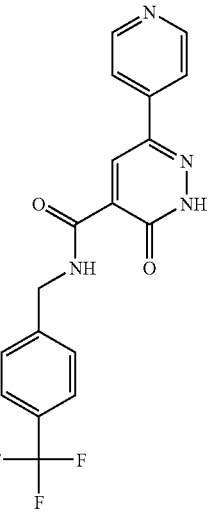 | 3-Oxo-6-pyridin-4-yl-2,3-dihydro-pyridazine-4-carboxylic acid 4-trifluoromethyl-benzylamide; compound with trifluoro-acetic acid | 375.1 | 13 |
| 113 | 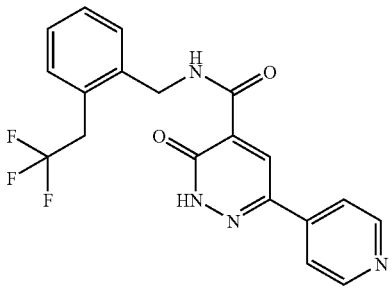 | 3-Oxo-6-pyridin-4-yl-2,3-dihydro-pyridazine-4-carboxylic acid 2-trifluoromethoxy-benzylamide; compound with trifluoro-acetic acid | 391.09 | 13 |

| Example | structural formula | name | M + 1 peak | synthesis according to example |
|---|---|---|---|---|
| 114 | | 3-Oxo-6-pyridin-4-yl-2,3-dihydro-pyridazine-4-carboxylic acid 3-trifluoromethoxy-benzylamide; compound with trifluoro-acetic acid | 391.09 | 13 |
| 115 | | 3-Oxo-6-pyridin-4-yl-2,3-dihydro-pyridazine-4-carboxylic acid 3,4-difluoro-benzylamide; compound with trifluoro-acetic acid | 343.09 | 13 |
| 116 | | 3-Oxo-6-pyridin-4-yl-2,3-dihydro-pyridazine-4-carboxylic acid 4-chloro-2-fluoro-benzylamide; compound with trifluoro-acetic acid | 359.06 | 13 |
| 117 | | 3-Oxo-6-pyridin-4-yl-2,3-dihydro-pyridazine-4-carboxylic acid 2,4-difluoro-benzylamide; compound with trifluoro-acetic acid | 343.09 | 13 |

-continued

| Example | structural formula | name | M + 1 peak | synthesis according to example |
|---|---|---|---|---|
| 118 | | 3-Oxo-6-pyridin-4-yl-2,3-dihydro-pyridazine-4-carboxylic acid [2-(2-fluoro-phenyl)-ethyl]-amide; compound with trifluoro-acetic acid | 339.12 | 13 |
| 119 | | 3-Oxo-6-pyridin-4-yl-2,3-dihydro-pyridazine-4-carboxylic acid 2-chloro-4-fluoro-benzylamide; compound with trifluoro-acetic acid | 359.06 | 13 |
| 120 | | 3-Oxo-6-pyridin-4-yl-2,3-dihydro-pyridazine-4-carboxylic acid 3,5-difluoro-benzylamide; compound with trifluoro-acetic acid | 343.09 | 13 |
| 121 | | 3-Oxo-6-pyridin-4-yl-2,3-dihydro-pyridazine-4-carboxylic acid [2-(3-fluoro-phenyl)-ethyl]-amide; compound with trifluoro-acetic acid | 339.12 | 13 |

-continued

| Example | structural formula | name | M + 1 peak | synthesis according to example |
|---|---|---|---|---|
| 122 | | 3-Oxo-6-pyridin-4-yl-2,3-dihydro-pyridazine-4-carboxylic acid 3-fluoro-benzylamide; compound with trifluoro-acetic acid | 325.1 | 13 |
| 123 | | 3-Oxo-6-pyridin-4-yl-2,3-dihydro-pyridazine-4-carboxylic acid [1-(4-fluoro-phenyl)-ethyl]-amide; compound with trifluoro-acetic acid | 339.12 | 13 |
| 124 | | 3-Oxo-6-pyridin-4-yl-2,3-dihydro-pyridazine-4-carboxylic acid [2-(4-fluoro-phenyl)-ethyl]-amide; compound with trifluoro-acetic acid | 339.12 | 13 |
| 125 | | 3-Oxo-6-pyridin-4-yl-2,3-dihydro-pyridazine-4-carboxylic acid 4-fluoro-benzylamide; compound with trifluoro-acetic acid | 325.1 | 13 |

-continued

| Example | structural formula | name | M + 1 peak | synthesis according to example |
|---|---|---|---|---|
| 126 | | 3-Oxo-6-pyridin-4-yl-2,3-dihydro-pyridazine-4-carboxylic acid (2-hydroxy-1,1-dimethyl-ethyl)-amide; compound with trifluoro-acetic acid | 289.12 | 13 |
| 127 | | 3-Oxo-6-pyridin-4-yl-2,3-dihydro-pyridazine-4-carboxylic acid [2-(5-bromo-2-methoxy-phenyl)-ethyl]-amide; compound with trifluoro-acetic acid | 429.05 | 13 |
| 128 | CHIRAL | 3-Oxo-6-pyridin-4-yl-2,3-dihydro-pyridazine-4-carboxylic acid ((R)-1-phenyl-propyl)-amide; compound with trifluoro-acetic acid | 335.14 | 13 |
| 129 | CHIRAL | 3-Oxo-6-pyridin-4-yl-2,3-dihydro-pyridazine-4-carboxylic acid ((S)-2-methoxy-1-methyl-ethyl)-amide; compound with trifluoro-acetic acid | 289.12 | 13 |

-continued

| Example | structural formula | name | M + 1 peak | synthesis according to example |
|---|---|---|---|---|
| 130 | CHIRAL | 3-Oxo-6-pyridin-4-yl-2,3-dihydro-pyridazine-4-carboxylic acid [(R)-1-(3-methoxy-phenyl)-ethyl]-amide; compound with trifluoro-acetic acid | 351.14 | 13 |
| 131 | CHIRAL | 3-Oxo-6-pyridin-4-yl-2,3-dihydro-pyridazine-4-carboxylic acid ((R)-1-p-tolyl-ethyl)-amide; compound with trifluoro-acetic acid | 335.14 | 13 |
| 132 | | 3-Oxo-6-pyridin-4-yl-2,3-dihydro-pyridazine-4-carboxylic acid (2-fluoro-ethyl)-amide; compound with trifluoro-acetic acid | 263.09 | 13 |
| 133 | CHIRAL | 3-Oxo-6-pyridin-4-yl-2,3-dihydro-pyridazine-4-carboxylic acid ((R)-1-phenyl-ethyl)-amide; compound with trifluoro-acetic acid | 321.13 | 13 |

-continued

| Example | structural formula | name | M + 1 peak | synthesis according to example |
|---|---|---|---|---|
| 134 | CHIRAL | 3-Oxo-6-pyridin-4-yl-2,3-dihydro-pyridazine-4-carboxylic acid ((R)-1-naphthalen-2-yl-ethyl)-amide; compound with trifluoro-acetic acid | 371.14 | 13 |
| 135 | | 3-Oxo-6-pyridin-4-yl-2,3-dihydro-pyridazine-4-carboxylic acid cyclohexylamide; compound with trifluoro-acetic acid | 299.14 | 13 |
| 136 | CHIRAL | 3-Oxo-6-pyridin-4-yl-2,3-dihydro-pyridazine-4-carboxylic acid ((S)-2-hydroxy-1-phenyl-ethyl)-amide; compound with trifluoro-acetic acid | 337.12 | 13 |

-continued

| Example | structural formula | name | M + 1 peak | synthesis according to example |
|---|---|---|---|---|
| 137 | | 3-Oxo-6-pyridin-4-yl-2,3-dihydro-pyridazine-4-carboxylic acid [2-(3,4-difluoro-phenoxy)-ethyl]-amide; compound with trifluoro-acetic acid | 373.1 | 13 |
| 138 | | 3-Oxo-6-pyridin-4-yl-2,3-dihydro-pyridazine-4-carboxylic acid 4-butoxy-benzylamide; compound with trifluoro-acetic acid | 379.17 | 13 |
| 139 | | 3-Oxo-6-pyridin-4-yl-2,3-dihydro-pyridazine-4-carboxylic acid (5-methyl-thiophen-2-ylmethyl)-amide; compound with trifluoro-acetic acid | 327.08 | 13 |

| Example | structural formula | name | M + 1 peak | synthesis according to example |
|---|---|---|---|---|
| 140 | | 3-Oxo-6-pyridin-4-yl-2,3-dihydro-pyridazine-4-carboxylic acid (1-thiophen-2-yl-ethyl)-amide; compound with trifluoro-acetic acid | 327.08 | 13 |
| 141 | | 3-Oxo-6-pyridin-4-yl-2,3-dihydro-pyridazine-4-carboxylic acid (3-methyl-thiophen-2-ylmethyl)-amide; compound with trifluoro-acetic acid | 327.08 | 13 |
| 142 | | 3-Oxo-6-pyridin-4-yl-2,3-dihydro-pyridazine-4-carboxylic acid (5-chloro-thiophen-2-ylmethyl)-amide; compound with trifluoro-acetic acid | 347.03 | 13 |
| 143 | | 3-Oxo-6-pyridin-4-yl-2,3-dihydro-pyridazine-4-carboxylic acid (5-ethyl-thiophen-2-ylmethyl)-amide; compound with trifluoro-acetic acid | 341.1 | 13 |

-continued

| Example | name | M + 1 peak | synthesis according to example |
|---------|------|------------|-------------------------------|
| 144 | 1-[(3-Oxo-6-pyridin-4-yl-2,3-dihydro-pyridazine-4-carbonyl)-amino]-indan-5-carboxylic acid butyl ester; compound with trifluoro-acetic acid | 433.18 | 13 |
| 145 | 3-Oxo-6-pyridin-4-yl-2,3-dihydro-pyridazine-4-carboxylic acid [2-(3-bromo-phenyl)-ethyl]-amide; compound with trifluoro-acetic acid | 399.04 | 13 |
| 146 | 3-Oxo-6-pyridin-4-yl-2,3-dihydro-pyridazine-4-carboxylic acid (1,2,3,4-tetrahydro-quinolin-4-yl)-amide; compound with trifluoro-acetic acid | 348.14 | 13 |

-continued

| Example | structural formula | name | M + 1 peak | synthesis according to example |
|---|---|---|---|---|
| 147 | | 3-Oxo-6-pyridin-4-yl-2,3-dihydro-pyrizadine-4-carboxylic acid [2-ethyl-2-(3-methoxy-phenyl)-butyl]-amide; compound with trifluoro-acetic acid | 407.2 | 13 |
| 148 | | 3-Oxo-6-pyridin-4-yl-2,3-dihydro-pyridazine-4-carboxylic acid (3-morpholin-4-yl-butyl)-amide; compound with trifluoro-acetic acid | 358.18 | 13 |
| 149 | | 3-Oxo-6-pyridin-4-yl-2,3-dihydro-pyridazine-4-carboxylic acid [2-(1H-indol-3-yl)-1,1-dimethyl-ethyl]-amide; compound with trifluoro-acetic acid | 388.17 | 13 |
| 150 | | 3-Oxo-6-pyridin-4-yl-2,3-dihydro-pyridazine-4-carboxylic acid [2-(5-methoxy-1H-indol-3-yl)-ethyl]-amide; compound with trifluoro-acetic acid | 390.15 | 13 |

| Example | structural formula | name | M + 1 peak | synthesis according to example |
|---|---|---|---|---|
| 151 | | 3-Oxo-6-pyridin-4-yl-2,3-dihydro-pyridazine-4-carboxylic acid 3-chloro-4-fluoro-benzylamide; compound with trifluoro-acetic acid | 359.06 | 13 |
| 152 | CHIRAL | 3-Oxo-6-pyridin-4-yl-2,3-dihydro-pyridazine-4-carboxylic acid [(R)-1-(4-methoxy-phenyl)-ethyl]-amide; compound with trifluoro-acetic acid | 351.14 | 13 |
| 153 | | 3-Oxo-6-pyridin-4-yl-2,3-dihydro-pyridazine-4-carboxylic acid [2-(3-isopropyl-phenoxy)-ethyl]-amide; compound with trifluoro-acetic acid | 379.17 | 13 |

-continued

| Example | structural formula | name | M + 1 peak | synthesis according to example |
|---------|-------------------|------|-----------|-------------------------------|
| 154 | | 3-Oxo-6-pyridin-4-yl-2,3-dihydro-pyridazine-4-carboxylic acid [2-(2-tert-butyl-phenoxy)-ethyl]-amide; compound with trifluoro-acetic acid | 393.19 | 13 |
| 155 | | 6-(4-Hydroxy-3-methy-phenyl-3-oxo-2,3-dihydro-pyridazine-4-carboxylic acid 4-chloro-benzylamide | 370.09 | 41 |
| 156 | | 3-Oxo-6-pyridin-4-yl-2,3-dihydro-pyridazine-4-carboxylic acid 4-(pyridin-4-ylcarbamoyl)-benzylamide; compound with trifluoro-acetic acid | 427.14 | 13 |
| 157 | | 3-Oxo-6-thiophen-3-yl-2,3-dihydro-pyridazine-4-carboxylic acid 4-chloro-benzylamide | 346.03 | 41 |

-continued

| Example | structural formula | name | M + 1 peak | synthesis according to example |
|---|---|---|---|---|
| 158 | | 6-(3,5-Dimethyl-isoxazol-4-yl)-3-oxo-2,3-dihydro-pyridazine-4-carboxylic acid 4-chloro-benzylamide | 359.08 | 41 |
| 159 | | 6-1,3-Benzodioxol-5-yl-3-oxo-2,3-dihydro-pyridazine-4-carboxylic acid 4-chloro-benzylamide | 384.07 | 41 |
| 160 | | 6-(3,4-Difluoro-phenyl)-3-oxo-2,3-dihydro-pyridazine-4-carboxylic acid 4-chloro-benzylamide | 376.06 | 41 |
| 161 | | 6-(4-Amino-phenyl)-3-oxo-2-dihydro-pyridazine-4-carboxylic acid 4-chloro-benzylamide | 355.09 | 13 |
| 162 | | 3-Oxo-6-pyrimidin-5-yl-2,3-dihydro-pyridazine-4-carboxylic acid 4-chloro-benzylamide | 342.07 | 13 |

-continued

| Example | structural formula | name | M + 1 peak | synthesis according to example |
|---------|-------------------|------|------------|-------------------------------|
| 163 | | 3-Oxo-6-pyridin-4-yl-2,3-dihydro-pyridazine-4-carboxylic acid 2-trifluoromethyl-benzylamide; compound with trifluoro-acetic acid | 375.1 | 13 |
| 164 | | 6-(4-Hydroxy-phenyl)-3-oxo-2,3-dihydro-pyridazine-4-carboxylic acid (3-pyridin-3-yl-propyl)-amide | 351.14 | 13 |
| 165 | | 6-(2-Methyl-pyrimidin-4-yl)-3-oxo-2,3-dihydro-pyridazine-4-carboxylic acid 4-chloro-benzylamide | 356.08 | 13 |
| 166 | | 3-Oxo-6-pyridin-4-yl-2,3-dihydro-pyridazine-4-carboxylic acid (2-[1,3]dioxolan-2-yl-ethyl)-amide | 317.12 | 13 |

-continued

| Example | structural formula | name | M + 1 peak | synthesis according to example |
|---------|--------------------|------|------------|-------------------------------|
| 167 | CHIRAL | R-3-Oxo-6-[2-(1-phenyl-ethylamino)-pyrimidin-4-yl]-2,3-dihydro-pyridazine-4-carboxylic acid (3-pyridin-3-yl-propyl)-amide | 456.21 | 13 |
| 168 | | 6-(6-Methyl-thiazolo[3,2-b][1,2,4]triazol-5-yl)-3-oxo-2,3-dihydro-pyridazine-4-carboxylic acid 4-chloro-benzylamide | 401.05 | 13 |
| 169 | | 6-(2-Methyl-pyrimidin-4-yl)-3-oxo-2,3-dihydro-pyridazine-4-carboxylic acid [2-(4-fluoro-phenyl)-ethyl]-amide | 354.13 | 13 |
| 170 | | 6-(2-Methyl-pyrimidin-4-yl)-3-oxo-2,3-dihydro-pyridazine-4-carboxylic acid indan-2-ylamide | 348.14 | 13 |

-continued

| Example | structural formula | name | M + 1 peak | synthesis according to example |
|---|---|---|---|---|
| 171 | | 3-Oxo-6-pyridin-4-yl-2,3-dihydro-pyridazine-4-carboxylic acid 4-trifluoromethoxy-benzylamide | 391.09 | 13 |
| 172 | | 3-Oxo-6-pyridin-4-yl-2,3-dihydro-pyridazine-4-carboxylic acid (2-amino-4-chloro-phenyl)-amide | 342.07 | 13 |
| 173 | | 3-Oxo-6-pyridin-4-yl-2,3-dihydro-pyridazine-4-carboxylic acid [2-(4-sulfamoyl-phenyl)-ethyl]-amide | 400.1 | 13 |
| 174 | | 3-Oxo-6-pyridin-4-yl-2,3-dihydro-pyridazine-4-carboxylic acid (2-carbamoyl-4-chloro-phenyl)-amide | 370.06 | 13 |

-continued

| Example | structural formula | name | M + 1 peak | synthesis according to example |
|---|---|---|---|---|
| 175 | | 6-[2-(2-Morpholin-4-yl-ethylamino)-pyrimidin-4-yl]-3-oxo-2,3-dihydro-pyridazine-4-carboxylic acid 4-chloro-benzylamide; compound with trifluoro-acetic acid | 470.16 | 13 |
| 176 | | 6-Benzo[b]thiophen-3-yl-3-oxo-2,3-dihydro-pyridazine-4-carboxylic acid 4-chloro-benzylamide | 396.05 | 41 |
| 177 | | 6-(3-Fluoro-pyridin-4-yl)-3-oxo-2,3-dihydro-pyridazine-4-carboxylic acid 4-chloro-benzylamide | 359.06 | 41 |
| 178 | | 4-[5-(4-Chloro-benzylcarbamoyl)-6-oxo-1,6-dihydro-pyridazin-3-yl]-benzoic acid | 384.07 | 41 |

| Example | structural formula | name | M + 1 peak | synthesis according to example |
|---|---|---|---|---|
| 179 | | 3-[5-(4-Chloro-benzylcarbamoyl)-6-oxo-1,6-dihydro-pyridazine-3-yl]-benzoic acid | 384.07 | 41 |
| 180 | | 6-(3-Chloro-4-hydroxy-phenyl)-3-oxo-2,3-dihydro-pyridazine-4-carboxylic acid 4-chloro-benzylamide | 390.03 | 41 |
| 181 | | 6-(2-Chloro-4-hydroxy-phenyl)-3-oxo-2,3-dihydro-pyridazine-4-carboxylic acid 4-chloro-benzylamide | 390.03 | 41 |
| 182 | | 6-(3,5-Difluoro-4-hydroxy-phenyl)-3-oxo-2,3-dihydro-pyridazine-4-carboxylic acid 4-chloro-benzylamide | 392.05 | 41 |

-continued

| Example | structural formula | name | M + 1 peak | synthesis according to example |
|---|---|---|---|---|
| 183 | | 6-(3-Fluoro-4-hydroxy-phenyl)-3-oxo-2,3-dihydro-pyridazine-4-carboxylic acid 4-chloro-benzylamide | 374.06 | 41 |
| 184 | | 6-(2-Butylamino-pyrimidin-4-yl)-3-oxo-2,3-dihydro-pyridazine-4-carboxylic acid [3-(4-methyl-piperazin-1-yl)-propyl]-amide | 429.07 | 13 |
| 185 | | 3-Oxo-6-pyridin-4-yl-2,3-dihydro-pyridazine-4-carboxylic acid (2-cyclohexylamino-ethyl)-amide | 342.19 | 13 |
| 186 | | 6-(3-Methyl-pyridin-4-yl)-3-oxo-2,3-dihydro-pyridazine-4-carboxylic acid 4-chloro-benzylamide; compound with trifluoro-acetic acid | 355.09 | 13 |
| 187 | | 3-Oxo-6-pyridin-4-yl-2,3-dihydro-pyridazine-4-carboxylic acid (4-amino-pyridin-3-yl)-amide | 309.1 | 13 |

| Example | structural formula | name | M + 1 peak | synthesis according to example |
|---|---|---|---|---|
| 188 | | 3-Oxo-6-pyridin-4-yl-2,3-dihydro-pyridazine-4-carboxylic acid 2-amino-benzylamide | 322.12 | 13 |
| 189 | | 3-Oxo-6-pyridin-4-yl-2,3-dihydro-pyridazine-4-carboxylic acid (2-amino-cyclohexyl)-amide | 314.15 | 13 |
| 190 | | 6-(2-Ethylamino-pyrimidin-4-yl)-3-oxo-2,3-dihydro-pyridazine-4-carboxylic acid 4-chloro-benzylamide | 385.11 | 13 |
| 191 | | 5-[5-(4-Chloro-benzylcarbamoyl)-6-oxo-1,6-dihydro-pyridazin-3-yl]-thiophene-2-carboxylic acid | 390.02 | 41 |

-continued

| Example | name | M + 1 peak | synthesis according to example |
|---|---|---|---|
| 192 | 4-[5-(4-Chloro-benzylcarbamoyl)-6-oxo-1,6-dihydro-pyridazin-3-yl]-thiophene-2-carboxylic acid | 390.02 | 41 |
| 193 | 6-(4-Methyl-2-pyridin-3-yl-thiazol-5-yl)-3-oxo-2,3-dihydro-pyridazine-4-carboxylic acid 4-chloro-benzylamide | 438.07 | 13 |
| 194 | 6-[2-(4-Chloro-phenyl)-pyrimidin-4-yl]-3-oxo-2,3-dihydro-pyridazine-4-carboxylic acid 4-chloro-benzylamide | 452.06 | 13 |
| 195 | 6-(2,6-Dimethyl-pyrimidin-4-yl)-3-oxo-2,3-dihydro-pyridazine-4-carboxylic acid 4-chloro-benzylamide-hydrochloride | 370.1 | 13 |

-continued

| Example | structural formula | name | M + 1 peak | synthesis according to example |
|---|---|---|---|---|
| 196 | 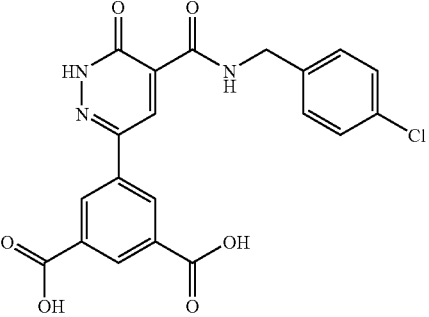 | 5-[5-(4-Chloro-benzylcarbamoyl)-6-oxo-1,6-dihydro-pyridazin-3-yl]-isophthalic acid | 428.06 | 13 |
| 197 | 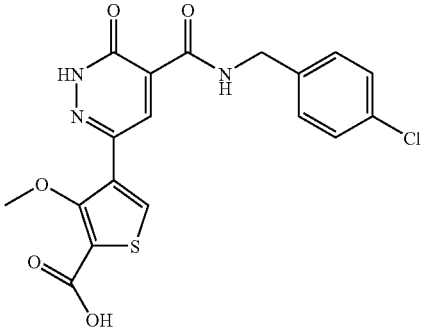 | 4-[5-(4-Chloro-benzylcarbamoyl)-6-oxo-1,6-dihydro-pyridazin-3-yl]-3-methoxy-thiophene-2-carboxylic acid | 420.03 | 41 |
| 198 | 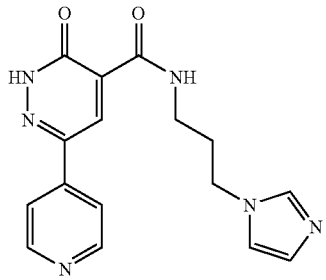 | 3-Oxo-6-pyridin-4-yl-2,3-dihydro-pyridazine-4-carboxylic acid (3-imidazol-1-yl-propyl)-amide | 325.13 | 13 |
| 199 | 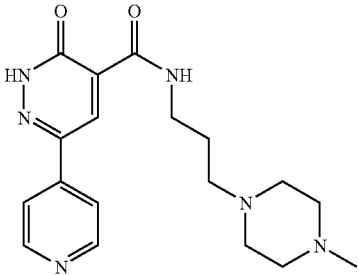 | 3-Oxo-6-pyridin-4-yl-2,3-dihydro-pyridazine-4-carboxylic acid [3-(4-methyl-piperazin-1-yl)-propyl]-amide | 357.2 | 13 |
| 200 | 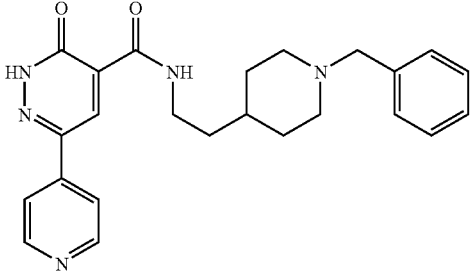 | 3-Oxo-6-pyridin-4-yl-2,3-dihydro-pyridazine-4-carboxylic acid [2-(1-benzyl-piperidin-4-yl)-ethyl]-amide | 418.22 | 13 |

-continued

| Example | structural formula | name | M + 1 peak | synthesis according to example |
|---|---|---|---|---|
| 201 | | 3-Oxo-6-pyridin-4-yl-2,3-dihydro-pyridazine-4-carboxylic acid 4-(2-dimethylamino-ethoxy)-benzylamide | 394.18 | 13 |
| 202 | | 3-Oxo-6-pyridin-4-yl-2,3-dihydro-pyridazine-4-carboxylic acid (1-carbamimidoyl-piperidin-4-ylmethyl)-amide | 356.18 | 13 |
| 203 | | 3-Oxo-6-pyridin-4-yl-2,3-dihydro-pyridazine-4-carboxylic acid (3-cyclohexylamino-propyl)-amide | 356.2 | 13 |
| 204 | | 4-{[(3-Oxo-6-pyridin-4-yl-2,3-dihydro-pyridazine-4-carbonyl)-amino]-methyl}-benzoic acid | 351.1 | 13 |

-continued

| Example | structural formula | name | M + 1 peak | synthesis according to example |
|---|---|---|---|---|
| 205 | | 6-(2-Benzylamino-pyridin-4-yl)-3-oxo-2,3-dihydro-pyridazine-4-carboxylic acid 4-chloro-benzylamide | 446.13 | 41 |
| 206 | | 6-(2-Methylamino-pyridin-4-yl)-3-oxo-2,3-dihydro-pyridazine-4-carboxylic acid 4-chloro-benzylamide | 370.1 | 41 |
| 207 | | 6-(5-Carbamoyl-4-methoxy-thiophen-3-yl)-3-oxo-2,3-dihydro-pyridazine 4-carboxylic acid 4-chloro-benzylamide | 419.05 | 41 |
| 208 | | 6-(2-Methyl-pyridin-4-yl)-3-oxo-2,3-dihydro-pyridazine-4-carboxylic acid 4-chloro-benzylamide; compound with trifluoro-acetic acid | 355.09 | 41 |

| Example | structural formula | name | M + 1 peak | synthesis according to example |
|---|---|---|---|---|
| 209 | | 6-(4-Methylcarbamoyl-phenyl)-3-oxo-2,3-dihydro-pyridazine-4-carboxylic acid 4-chloro-benzylamide | 397.1 | 41 |
| 210 | | 6-(3-Methylcarbamoyl-phenyl)-3-oxo-2,3-dihydro-pyridazine-4-carboxylic acid 4-chloro-benzylamide | 397.1 | 41 |
| 211 | | 6-(4-Carbamoyl-phenyl)-3-oxo-2,3-dihydro-pyridazine-4-carboxylic acid 4-chloro-benzylamide | 383.08 | 41 |
| 212 | | 6-(3-Carbamoyl-phenyl)-3-oxo-2,3-dihydro-pyridazine-4-carboxylic acid 4-chloro-benzylamide | 383.08 | 41 |

-continued

| Example | structural formula | name | M + 1 peak | synthesis according to example |
|---------|-------------------|------|-----------|-------------------------------|
| 213 | CHIRAL | R-3-Oxo-6-[2-(1-phenyl-ethylamino)-pyrimidin-4-yl]-2,3-dihydro-pyridazine-4-carboxylic acid 4-chloro-benzylamide | 461.14 | 13 |
| 214 | CHIRAL | R-3-Oxo-6-[2-(1-phenyl-ethylamino)-pyrimidin-4-yl]-2,3-dihydro-pyridazine-4-carboxylic acid butylamide | 461.14 | 13 |
| 215 | CHIRAL | R-3-Oxo-6-[2-(1-phenyl-ethylamino)-pyrimidin-4-yl]-2,3-dihydro-pyridazine-4-carboxylic acid (3-phenyl-propyl)-amide | 455.21 | 13 |
| 216 | | 6-(2-Butylamino-pyrimidin-4-yl)-3-oxo-2,3-dihydro-pyridazine-4-carboxylic acid 4-chloro-benzylamide | 413.14 | 13 |

|Example|structural formula|name|M + 1 peak|synthesis according to example|
|---|---|---|---|---|
|217||4-{[(3-Oxo-6-pyridin-4-yl-2,3-dihydro-pyridazine-4-carbonyl)-amino]-methyl}-benzoic acid methyl ester; compound with trifluoro-acetic acid|365.12|13|
|218||6-(2-Butylamino-pyrimidin-4-yl)-3-oxo-2,3-dihydro-pyridazine-4-carboxylic acid [3-(4-methyl-piperazin-1-yl)-propyl]-amide; compound with trifluoro-acetic acid|429.27|13|
|219||6-(2-Butylamino-pyrimidin-4-yl)-3-oxo-2,3-dihydro-pyridazine-4-carboxylic acid (pyridin-3-ylmethyl)-amide|380.18|13|
|220||6-(2-Butylamino-pyrimidin-4-yl)-3-oxo-2,3-dihydro-pyridazine-4-carboxylic acid (3-pyridin-3-yl-propyl)-amide|408.21|13|
|221||6-(2-Ethylamino-pyrimidin-4-yl)-3-oxo-2,3-dihydro-pyridazine-4-carboxylic acid (3-cyclohexylamino-propyl)-amide|400.24|13|

-continued

| Example | structural formula | name | M + 1 peak | synthesis according to example |
|---|---|---|---|---|
| 222 | | 3-Oxo-6-(2-phenethylamino-pyridin-4-yl)-2,3-dihydro-pyridazine-4-carboxylic acid 4-chloro-benzylamide | 460.15 | 41 |
| 223 | | 6-[2-(2-Morpholin-4-yl-ethylamino)-pyridin-4-yl]-3-oxo-2,3-dihydro-pyridazine-4-carboxylic acid 4-chloro-benzylamide | 469.17 | 41 |
| 224 | | 6-(2-Ethylamino-pyridin-4-yl)-3-oxo-2,3-dihydro-pyridazine-4-carboxylic acid 4-chloro-benzylamide | 384.12 | 41 |
| 225 | | 4-({[6-(4-Hydroxy-3-methoxy-phenyl)-3-oxo-2,3-dihydro-pyridazine-4-carbonyl]-amino}-methyl)-benzoic acid | 396.11 | 41 |

EXAMPLE 41

6-(4-Hydroxy-3-methoxy-phenyl)-3-oxo-2,3-dihydro-pyridazine-4-carboxylic acid 4-chloro-benzyl amide a) 3,6-Dichloro-pyridazine-4-carboxylic acid A solution of 24.9 g 3,6-dichloro-4-methylpyridazine and 56.7 g potassium dichromate in 250 ml of concentrated sulphuric acid were stirred at 40° C. for 2 h, the reaction mixture was poured onto 1.5 l ice-water and extracted with ethyl acetate. The organic layer was extracted with water and a saturated solution of NaCl, dried over MgSO4 and evaporated. The raw product was used without any further purification.

Yield: 27.1 g
MS:M+1=193.1 b) 6-Chloro-3-oxo-2,3-dihydro-pyridazine-4-carboxylic acid 27 g of 3,6-dichloro-pyridazine-4-carboxylic acid were stirred at 50° C. for 6 h in a 1:1 mixture of concentrated sulphuric acid and water. The pure product crystallized after cooling off the reaction mixture and was filtered.

Yield: 12.48 g
MS:M+1=175.1 c) 6-Chloro-3-oxo-2,3-dihydro-pyridazine-4-carboxylic acid 4-chloro-benzyl amide Oxalyl chloride was added to a solution a 8.73 g of 6-chloro-3-oxo-2,3-dihydro-pyridazine-4-carboxylic acid and 1 ml DMF in 250 ml THF at 5-10° C. and the mixture was stirred at room temperature for 2 h. Afterwards, it was evaporated to dryness, the residue dissolved in 450 ml THF and 13.8 g potassium carbonate and a solution of 7.2 g 4-chloro-benzyl amide in THF were added. The solvent was distilled off after 2 h of stirring at room temperature, the residue suspended in 100 ml water and a pH of 6.4 was adjusted. The obtained precipitate was sucked off, suspended again in 50 ml water and the pH is adjusted to 3. Afterwards, the precipitate was sucked off and dried over phosphorous pentoxide in an desiccator.

Yield: 9.3 g
MS:M+1=298.

d) 6-Chloro-3-oxo-2-(2-trimethylsilyl-ethoxymethyl)-2,3-dihydro-pyradizine-4-carboxylic acid 4-chloro-benzyl amide 8.6 g of 6-chloro-3-oxo-2,3-dihydro-pyridazine-4-carboxylic acid 4 chloro-benzyl amide were dissolved in 100 ml of absolute DMF and 4.8 g N,N-diisopropylethyl amine were added, then it was stirred at room temperature for 30 min. Afterwards, 5.9 g of trimethylsilylethoxymethyl chloride was added dropwise and it was stirred at room temperature for 5 h. The mixture was added to 1000 ml water for working up, extracted with ethyl acetate, the organic layer was washed with a saturated solution of NaCl and dried over MgSO4. After distilling off the solvent the residue was chromatographically purified (silica gel, n-heptane/ethylacetate).

Yield: 7.6 g
MS:M+1=428.18.

e) 6-(4-Hydroxy-3-methoxy-phenyl)-3-oxo-2-(2-trimethylsilanyl-ethoxymethyl)-2,3-dihydro-pyradizine-4-carboxylic acid 4-chloro-benzyl amide A solution of 128.5 mg 6-chloro-3-oxo-2-(2-trimethylsilyl-ethoxymethyl)-2,3-dihydropyridazine-4-carboxylic acid 4-chloro-benzyl amide, 91.8 mg 2-methoxy-4-(4,4,5,5-tetramethyl-1,3,2-dioxaborolan-2-yl)-phenol, 82.9 mg K2CO3 and 32.1 mg triphenylphosphine in 3.2 ml DME/H2O (2/1) were degassed by conducting of argon. Afterwards, the mixture was diluted with ethyl acetate and washed with 0.5 N of HCl. After drying over MgSO4 the solvent was distilled off and the raw product was purified by HPLC (column 125×25, PurospherStar RP18 endcapped, 5 μm; solvent: A: water (0.05% HCOOH), B: acetonitrile (0.05% HCOOH)).

Yield: 70.7 mg
MS:M+1=516.31 f) 6-(4-Hydroxy-3-methoxy-phenyl)-3-oxo-2,3-dihydro-pyridazine-4-carboxylic acid 4-chloro-benzyl amide 70.7 mg of 6-(4-hydroxy-3-methoxy-phenyl)-3-oxo-2-(2-trimethylsilanyl-ethoxymethyl)-2,3-dihydro-pyridazine-4-carboxylic acid 4-chloro-benzyl amide and 60 μl ethandithiol and 60 μl water were dissolved in 750 μl TFA and stirred at room temperature for 3 h. Afterwards, the solvent was distilled off and the raw product purified by HPLC (column 125×25, PurospherStar RP18 endcapped, 5 μm; solvent: A: water (0.05% HCOOH), B: acetonitrile (0.05% HCOOH)).

Yield: 19.7 mg
MS:M+1=386.14

Functional Measurements for Determination of $IC_{50}$-Values

Tau-phosphorylation

The compounds' activities were determined by measuring the inhibition of phosphorylation of the Tau protein in adult rat cortex sections.

The cortex sections having a thickness of 300 μm were prepared from 8-10-week old male OFA rats (Iffa-Credo), sacrificed by decapitation. They were incubated in 5 ml of DMEM medium containing pyruvate and glucose 4.5 g/l at 37° C. for 40 min. The sections were then washed twice with the medium, distributed into microtubes (50 μl in 500 μl of medium with or without test compounds), and incubated at 37° C., with stirring. Two hours later, the experiment was stopped by centrifugation. The sections were washed, sonicated and centrifuged at 18300 g, for 15 min at 4° C. The concentration of proteins in supernatant was determined by a commercial assay (BCA Protein Assay, Pierce) based on the Lowry method.

The samples, denatured beforehand for 10 min at 70° C., were separated on a 4-12% Bis-Tris vertical gel in the presence of MOPS-SDS buffer and electrotransferred onto nitrocellulose membrane. Immunolabeling was performed with their monoclonal antibody AD2 which specifically recognizes the phosphorylated epitopes Ser396/404 of the Tau protein. The immunoactive proteins were visualized by adding a second antibody directed against the mouse IgG's and coupled to peroxidase and a chemiluminescent substrate. The autoradiograms obtained were finally quantified using the 'GeneTools' software from Syngene (GeneGnome, Ozyme) in order to determine an $IC_{50}$.

The compounds of formula (I) have a very advantageous activity and in particular some compounds have an $IC_{50}$ of less than 100 μM.

| Example | $IC_{50}[\mu M]$ |
| --- | --- |
| 2 | 22 |
| 4 | 13 |
| 8 | 9.0 |
| 10 | 9.5 |
| 16 | 3.5 |
| 19 | 4.1 |
| 22 | 22 |
| 34 | 0.24 |

-continued

| Example | IC$_{50}$[μM] |
|---|---|
| 40 | 0.3 |
| 43 | 2.2 |
| 52 | 19 |
| 53 | 19 |
| 66 | 1.1 |

GSK-3β

GSK-β activity was measured using human recombinant GSK-3β and a primed (pre-phosphorylated) substrate peptide (derived from glycogen synthase and containing the phosphorylation sites 3a, b, and c) on basis of the AlphaScreen technology in 384-well plate format (small volume plate, white, GREINER). In a final volume of 11 μl, 2 μl of compound (1 nM-100 mM in kinase buffer, DMSO kept constant at 0.9%), 2 μl of GSK-31 solution (0.18 nM) and 2 μl of biot. phospho-glycogen synthase peptide (34 nM) in kinase buffer (20 mM Hepes, pH 7.4, 10 mM MgCl, 200 mM EDTA, 1 mM DTT, 0.1 mg/ml BSA, 10 μM ATP) were incubated at room temperature for 60 min. After adding 2.5 ml Donor beads (20 μg/ml) and 2.5 ml antibody (anti-phospho-glycogen synthase 1:2000)-coated Acceptor beads (40 μg/ml) in AlphaScreen detection buffer (20 mM Hepes, pH 7.4, 10 mM MgCl, 40 mM EDTA, 1 mM DTT, 0.1 mg/ml BSA, plates were incubated at room temperature (in the dark!) over night and then placed in a reader (Alphaquest or Fusion) to measure final fluorescence. IC$_{50}$-values were calculated form the fitted curved corrected for blank values (absence of GSK-3β) and preformed in triplicate.

| Example | IC$_{50}$[μM] |
|---|---|
| 2 | 0.72 |
| 4 | 0.18 |
| 14 | 0.097 |
| 17 | 0.251 |
| 32 | 0.005 |
| 40 | 2.8 |
| 41 | 2.3 |
| 48 | 0.036 |
| 49 | 0.001 |
| 52 | >10 |
| 53 | 4.4 |
| 66 | 0.095 |
| 75 | 0.38 |
| 112 | 0.123 |
| 116 | 0.25 |
| 117 | 0.065 |
| 155 | 10.3 |
| 156 | 0.086 |
| 164 | 0.007 |
| 175 | 0.017 |
| 180 | 0.227 |
| 182 | 0.17 |
| 183 | 0.039 |
| 190 | >1 |
| 206 | 0.03 |
| 215 | 0.024 |
| 218 | 0.022 |
| 219 | 0.029 |
| 220 | 0.036 |
| 225 | 0.009 |

What is claimed is:

1. A compound, chosen from
   6-(2-butylamino-pyrimidin-4-yl)-3-oxo-2,3-dihydro-pyridazine-4-carboxylic acid (3-pyridin-3-yl-propyl)-amide,
   6-(4-hydroxy-3-methoxy-phenyl)-3-oxo-2,3-dihydro-pyridazine-4-carboxylic acid (3-pyridin-3-yl-propyl)-amide,
   6-(4-hydroxy-3,5-dimethyl-phenyl)-3-oxo-2,3-dihydro-pyridazine-4-carboxylic acid (3-pyridin-3-yl-propyl)-amide,
   6-(4-hydroxy-phenyl)-3-oxo-2,3-dihydro-pyridazine-4-carboxylic acid (3-pyridin-3-yl-propyl)-amide,
   6-(2-ethylamino-pyrimidin-4-yl)-3-oxo-2,3-dihydro-pyridazine-4-carboxylic acid 4-chloro-benzylamide,
   6-(3-chloro-4-hydroxy-phenyl)-3-oxo-2,3-dihydro-pyridazine-4-carboxylic acid 4-chloro-benzylamide,
   6-(4-hydroxy-3,5-dimethyl-phenyl)-3-oxo-2,3-dihydro-pyridazine-4-carboxylic acid 4-chloro-benzylamide,
   4-({[6-(4-hydroxy-3,5-dimethyl-phenyl)-3-oxo-2,3-dihydro-pyridazine-4-carbonyl) ]-amino}-methyl)-benzoic acid,
   4-({[6-(4-hydroxy-3-methoxy-phenyl)-3-oxo-2,3-dihydro-pyridazine-4-carbonyl) ]-amino}-methyl)-benzoic acid,
   6-(2-butylamino-pyrimidin-4-yl)-3-oxo-2,3-dihydro-pyridazine-4-carboxylic acid (pyridin-3-yl-methyl)-amide,
   6-(3-fluoro-4-hydroxy-phenyl)-3-oxo-2,3-dihydro-pyridazine-4-carboxylic acid 4-chloro-benzyl amide,
   6-(4-hydroxy-3-methyl-phenyl)-3-oxo-2,3-dihydro-pyridazine-4-carboxylic acid 4-chloro-benzylamide,
   6-[2-(2-morpholin-4-yl-ethylamino)-pyrimidin-4-yl]-3-oxo-2,3-dihydro-pyridazine-4-carboxylic acid 4-chloro-benzylamide,
   6-(4-hydroxy-3-methoxy-phenyl)-3-oxo-2,3-dihydro-pyridazine-4-carboxylic acid 4-chloro-benzylamide,
   6-(2-methylamino-pyrimidin-4-yl)-3-oxo-2,3-dihydro-pyridazine-4-carboxylic acid 4-chloro-benzylamide,
   R-3-oxo-6-[2-(1-phenyl-ethylamino)-pyrimidin-4-yl]-2,3-dihydro-pyridazine-4-carboxylic acid (3-phenyl-propyl)-amide,
   6-(4-hydroxy-phenyl)-3-oxo-2,3-dihydro-pyridazine-4-carboxylic acid 4-chloro-benzylamide,
   3-oxo-6-pyridin-4-yl-N-[4-(trifluoromethyl)benzyl]-2,3-dihydropyridazine-4-carboxamide,
   3-oxo-6-pyridin-4-yl-2,3-dihydro-pyridazine-4-carboxylic acid 4-bromo-benzylamide,
   3-oxo-6-pyridin-4-yl-N-(pyridin-3-ylmethyl)-2,3-dihydropyridazine-4-carboxamide,
   N-(2,4-dichlorobenzyl)-3-oxo-6-pyridin-4-yl-2,3-dihydropyridazine-4-carboxamide,
   3-oxo-6-pyridin-4-yl-2,3-dihydro-pyridazi ne-4-carboxylic acid 4-chloro-2-fluoro-benzylamide, and
   N-(4-chlorobenzyl)-3-oxo-6-pyridin-4-yl-2,3-dihydropyridazine-4-carboxamide;
   the racemates, enantiomers, diastereoisomers and mixtures thereof, and the tautomers or the physiologically acceptable salts thereof.

2. A method for treating a patient suffering from a disease chosen from cranial and spinal traumas and peripheral neuropathies, obesity, type II diabetes, essential hypertension, atherosclerotic cardiovascular diseases, and polycystic ovary syndrome, which method comprises administering a physiologically active amount of a compound according to claim 1.

3. The method according to claim 2, wherein the disease is type-II-diabetes.

4. A method for treating a patient suffering from a disease chosen from cranial and spinal traumas and peripheral neuropathies, obesity, type II diabetes, essential hypertension, atherosclerotic cardiovascular diseases, and polycystic ovary syndrome, which method comprises administering a physiologically active amount of a compound chosen from the following compounds:

- 6-(4-methoxy-phenyl)-3-oxo-2,3-dihydro-pyridazine-4-carboxylic acid (3-pyridin-3-yl-propyl)-amide;
- 6-(4-hydroxy-3-methoxy-phenyl)-3-oxo-2,3-dihydro-pyridazine-4-carboxylic acid 4-chloro-benzylamide;
- 6-(4-hydroxy-3-methoxy-phenyl)-3-oxo-2,3-dihydro-pyridazine-4-carboxylic acid (3-pyridin-3-yl-propyl)-amide;
- 6-(4-methoxy-phenyl)-3-oxo-2,3-dihydro-pyridazine-4-carboxylic acid 4-chloro-benzyl amide;
- 4-[5-(4-chloro-benzylcarbamoyl)-6-oxo-1,6-dihydro-pyridazin-3-yl]-3-methoxy-thiophene-2-carboxylic acid;
- 6-(5-carbamoyl-4-methoxy-thiophen-3-yl)-3-oxo-2,3-dihydro-pyridazine-4-carboxylic acid 4-chloro-benzylamide; and
- 4-({[6-(4-hydroxy-3-methoxy-phenyl)-3-oxo-2,3-dihydro-pyridazine-4-carbonyl]-amino) }-methyl)-benzoic acid.

\* \* \* \* \*

UNITED STATES PATENT AND TRADEMARK OFFICE
CERTIFICATE OF CORRECTION

PATENT NO. : 7,309,701 B2
APPLICATION NO. : 10/715358
DATED : December 18, 2007
INVENTOR(S) : Swen Hölder et al.

Page 1 of 1

It is certified that error appears in the above-identified patent and that said Letters Patent is hereby corrected as shown below:

In claim 1, column 144, line 21, delete closed parenthesis after "-4-carbonyl".

In claim 1, column 144, line 24, delete closed parenthesis after "-4-carbonyl".

In claim 1, column 144, line 30, "benzyl amide" should read -- benzylamide --.

In claim 1, column 144, line 54, "pyridazi ne" should read -- pyridazine --.

In claim 4, column 146, line 2, "benzyl amide" should read -- benzylamide --.

In claim 4, column 146, line 10, delete closed parenthesis after "amino".

Signed and Sealed this

Third Day of June, 2008

JON W. DUDAS
*Director of the United States Patent and Trademark Office*